(12) United States Patent
Andres et al.

(10) Patent No.: US 12,281,113 B2
(45) Date of Patent: Apr. 22, 2025

(54) CRYSTALLINE FORMS OF A KRas G12C INHIBITOR

(71) Applicant: MIRATI THERAPEUTICS, INC., San Diego, CA (US)

(72) Inventors: Patricia Andres, San Diego, CA (US); Samuel Andrew, Cambridge (GB); Cheng Yi Chen, San Diego, CA (US); Susana Del Rio Gancedo, Cambridge (GB); Tawfik Gharbaoui, Escondido, CA (US); Jennifer Nelson, West Lafayette, IN (US)

(73) Assignee: MIRATI THERAPEUTICS, INC., Princeton, NJ (US)

( * ) Notice: Subject to any disclaimer, the term of this patent is extended or adjusted under 35 U.S.C. 154(b) by 0 days.

(21) Appl. No.: 18/782,879

(22) Filed: Jul. 24, 2024

(65) Prior Publication Data

US 2024/0376107 A1    Nov. 14, 2024

Related U.S. Application Data

(63) Continuation of application No. 18/025,817, filed as application No. PCT/US2021/049940 on Sep. 10, 2021.

(60) Provisional application No. 63/093,673, filed on Oct. 19, 2020, provisional application No. 63/077,553, filed on Sep. 11, 2020.

(51) Int. Cl.
  *C07D 471/04*    (2006.01)
  *A61P 35/00*    (2006.01)

(52) U.S. Cl.
  CPC ............ *C07D 471/04* (2013.01); *A61P 35/00* (2018.01); *C07B 2200/13* (2013.01)

(58) Field of Classification Search
  CPC .... C07D 471/04; A61P 35/00; C07B 2200/13
  See application file for complete search history.

(56) References Cited

U.S. PATENT DOCUMENTS 6,924,284 B2    8/2005   Beaton et al.
8,163,763 B2    4/2012   Bergeron et al.
(Continued)

FOREIGN PATENT DOCUMENTS

CN    110256421 A    9/2019
CN    113999226 A    2/2022
(Continued)

OTHER PUBLICATIONS

Kyriakis, John M., (Dec. 17, 2008) "Thinking Outside the Box About Ras", Journal of Biological Chemistry, 284(17):10993-10994.
(Continued)

*Primary Examiner* — Clinton A Brooks
*Assistant Examiner* — Izabela Schmidt
(74) *Attorney, Agent, or Firm* — Mintz, Levin, Cohn, Ferris, Glovsky and Popeo, P.C.

(57) ABSTRACT

The present invention relates to crystalline forms of a KRas G12C inhibitor and salt thereof. In particular, the present invention relates to crystalline forms of the KRas G12C inhibitor 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, pharmaceutical compositions comprising the crystalline forms, processes for preparing the crystalline forms and methods of use thereof.

30 Claims, 30 Drawing Sheets

(56) References Cited

U.S. PATENT DOCUMENTS

| | | |
|---|---|---|
| 8,426,401 B2 | 4/2013 | Bian et al. |
| 9,562,019 B2 | 2/2017 | Djaballah et al. |
| 9,840,516 B2 | 12/2017 | Li et al. |
| 10,125,134 B2 | 11/2018 | Blake et al. |
| 2003/0191143 A1 | 10/2003 | Pitts et al. |
| 2006/0229307 A1 | 10/2006 | Blurton et al. |
| 2007/0021445 A1 | 1/2007 | Berthel et al. |
| 2009/0312342 A1 | 12/2009 | Wilson et al. |
| 2010/0081654 A1 | 4/2010 | Stockwell et al. |
| 2011/0269244 A1 | 11/2011 | Petter et al. |
| 2013/0029978 A1 | 1/2013 | Kamino et al. |
| 2014/0288045 A1 | 9/2014 | Ren et al. |
| 2015/0175558 A1 | 6/2015 | Stockwell et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0166571 A1 | 6/2016 | Janes et al. |
| 2016/0229836 A1 | 8/2016 | Stockwell et al. |
| 2016/0264627 A1 | 9/2016 | Henning et al. |
| 2016/0297774 A1 | 10/2016 | Li et al. |
| 2017/0022184 A1 | 1/2017 | Li et al. |
| 2017/0115303 A1 | 4/2017 | Cravatt et al. |
| 2017/0190672 A1 | 7/2017 | Mani et al. |
| 2017/0197945 A1 | 7/2017 | Li et al. |
| 2017/0275289 A1 | 9/2017 | Albrecht et al. |
| 2018/0015087 A1 | 1/2018 | Liu et al. |
| 2018/0072723 A1 | 3/2018 | Blake et al. |
| 2018/0118757 A1 | 5/2018 | Li et al. |
| 2018/0118761 A1 | 5/2018 | Sebti et al. |
| 2018/0127396 A1 | 5/2018 | Li et al. |
| 2018/0141927 A1 | 5/2018 | Li et al. |
| 2018/0155348 A1 | 6/2018 | Li et al. |
| 2018/0162812 A1 | 6/2018 | Ren et al. |
| 2018/0177767 A1 | 6/2018 | Lanman et al. |
| 2018/0194748 A1 | 7/2018 | Li et al. |
| 2018/0201610 A1 | 7/2018 | Tao et al. |
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | Mccormick et al. |
| 2019/0144444 A1* | 5/2019 | Blake ............... A61P 35/00 514/210.21 |
| 2019/0270743 A1 | 9/2019 | Marx et al. |
| 2019/0374542 A1 | 12/2019 | Allen et al. |
| 2020/0069657 A1 | 3/2020 | Lanman et al. |
| 2020/0262837 A1 | 8/2020 | Marx et al. |
| 2020/0331911 A1 | 10/2020 | Marx et al. |
| 2020/0399297 A1 | 12/2020 | Mcinnes et al. |
| 2021/0024501 A1 | 1/2021 | Li et al. |
| 2021/0139517 A1 | 5/2021 | Gill et al. |

FOREIGN PATENT DOCUMENTS

| | | |
|---|---|---|
| JP | 2015124211 A | 7/2015 |
| WO | 02053558 A1 | 7/2002 |
| WO | 02087513 A2 | 11/2002 |
| WO | 2007146122 A2 | 12/2007 |
| WO | 2008009078 A2 | 1/2008 |
| WO | 2009047255 A1 | 4/2009 |
| WO | 2010014939 A1 | 2/2010 |
| WO | 2010120996 A1 | 10/2010 |
| WO | 2013155223 A1 | 10/2013 |
| WO | 2014143659 A1 | 9/2014 |
| WO | 2014152588 A1 | 9/2014 |
| WO | 2015054572 A1 | 4/2015 |
| WO | 2016025650 A1 | 2/2016 |
| WO | 2016044772 A1 | 3/2016 |
| WO | 2016049565 A1 | 3/2016 |
| WO | 2016049568 A1 | 3/2016 |
| WO | 2016130460 A2 | 8/2016 |
| WO | 2016164675 A1 | 10/2016 |
| WO | 2016168540 A1 | 10/2016 |
| WO | 2017058728 A1 | 4/2017 |
| WO | 2017058768 A1 | 4/2017 |
| WO | 2017058792 A1 | 4/2017 |
| WO | 2017058805 A1 | 4/2017 |
| WO | 2017058807 A1 | 4/2017 |
| WO | 2017058902 A1 | 4/2017 |
| WO | 2017058915 A1 | 4/2017 |
| WO | 2017070256 A2 | 4/2017 |
| WO | 2017079864 A1 | 5/2017 |
| WO | 2017080980 A1 | 5/2017 |
| WO | 2017087528 A1 | 5/2017 |
| WO | 2017100546 A1 | 6/2017 |
| WO | 2018064510 A1 | 4/2018 |
| WO | 2018068017 A1 | 4/2018 |
| WO | 2018102452 A2 | 6/2018 |
| WO | 2018102453 A1 | 6/2018 |
| WO | 2018112420 A1 | 6/2018 |
| WO | 2018115380 A1 | 6/2018 |
| WO | 2018119183 A2 | 6/2018 |
| WO | 2018140512 A1 | 8/2018 |
| WO | 2018140513 A1 | 8/2018 |
| WO | 2018140514 A1 | 8/2018 |
| WO | 2018140598 A1 | 8/2018 |
| WO | 2018140599 A1 | 8/2018 |
| WO | 2018140600 A1 | 8/2018 |
| WO | 2018143315 A1 | 8/2018 |
| WO | 2018195439 A2 | 10/2018 |
| WO | 2018218070 A2 | 11/2018 |
| WO | 2019051291 A1 | 3/2019 |
| WO | 2019099524 A1 | 5/2019 |
| WO | 2020027202 A1 | 2/2020 |
| WO | 2020063594 A1 | 4/2020 |
| WO | 2020097537 A2 | 5/2020 |
| WO | 2020098488 A1 | 5/2020 |
| WO | 2020118066 A1 | 6/2020 |
| WO | 2020123395 A1 | 6/2020 |
| WO | 2020146613 A1 | 7/2020 |
| WO | 2020163598 A1 | 8/2020 |
| WO | 2020165670 A1 | 8/2020 |
| WO | 2020169838 A1 | 8/2020 |
| WO | 2020171499 A1 | 8/2020 |
| WO | 2020172332 A1 | 8/2020 |
| WO | 2020176693 A2 | 9/2020 |
| WO | 2020176963 A1 | 9/2020 |
| WO | 2020177629 A1 | 9/2020 |
| WO | 2020178282 A1 | 9/2020 |
| WO | 2020181142 A1 | 9/2020 |
| WO | 2020198125 A1 | 10/2020 |
| WO | 2020204359 A1 | 10/2020 |
| WO | 2020205473 A1 | 10/2020 |
| WO | 2020205486 A1 | 10/2020 |
| WO | 2020212895 A1 | 10/2020 |
| WO | 2020214537 A1 | 10/2020 |
| WO | 2020221239 A1 | 11/2020 |
| WO | 2020230028 A1 | 11/2020 |
| WO | 2020230091 A1 | 11/2020 |
| WO | 2020231806 A1 | 11/2020 |
| WO | 2020231808 A1 | 11/2020 |
| WO | 2020232130 A1 | 11/2020 |
| WO | 2020233592 A1 | 11/2020 |
| WO | 2020234103 A1 | 11/2020 |
| WO | 2020236940 A1 | 11/2020 |
| WO | 2020236947 A1 | 11/2020 |
| WO | 2020236948 A1 | 11/2020 |
| WO | 2020247914 A1 | 12/2020 |
| WO | 2020252336 A1 | 12/2020 |
| WO | 2020252353 A1 | 12/2020 |
| WO | 2021000885 A1 | 1/2021 |
| WO | 2021023154 A1 | 2/2021 |
| WO | 2021023247 A1 | 2/2021 |
| WO | 2021027911 A1 | 2/2021 |
| WO | 2021027943 A1 | 2/2021 |
| WO | 2021031952 A1 | 2/2021 |
| WO | 2021034992 A1 | 2/2021 |
| WO | 2021037018 A1 | 3/2021 |
| WO | 2021041671 A1 | 3/2021 |
| WO | 2021043322 A1 | 3/2021 |
| WO | 2021045279 A1 | 3/2021 |
| WO | 2021050732 A1 | 3/2021 |

(56) References Cited

FOREIGN PATENT DOCUMENTS

| | | |
|---|---|---|
| WO | 2021051034 A1 | 3/2021 |
| WO | 2021052499 A1 | 3/2021 |
| WO | 2021055728 A1 | 3/2021 |
| WO | 2021057832 A1 | 4/2021 |
| WO | 2021058018 A1 | 4/2021 |
| WO | 2021061515 A1 | 4/2021 |
| WO | 2021061749 A1 | 4/2021 |
| WO | 2021063346 A1 | 4/2021 |
| WO | 2021068898 A1 | 4/2021 |
| WO | 2021075147 A1 | 4/2021 |
| WO | 2021076655 A1 | 4/2021 |
| WO | 2021078285 A1 | 4/2021 |
| WO | 2021078312 A1 | 4/2021 |
| WO | 2021080359 A1 | 4/2021 |
| WO | 2021081212 A1 | 4/2021 |
| WO | 2021083167 A1 | 5/2021 |
| WO | 2021084765 A1 | 5/2021 |
| WO | 2021085653 A1 | 5/2021 |
| WO | 2021086833 A1 | 5/2021 |
| WO | 2021088458 A1 | 5/2021 |
| WO | 2021088938 A1 | 5/2021 |
| WO | 2021090855 A1 | 5/2021 |
| WO | 2021091956 A1 | 5/2021 |
| WO | 2021091967 A1 | 5/2021 |
| WO | 2021091982 A1 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A1 | 9/2021 |
| WO | 2021178741 A1 | 9/2021 |
| WO | 2021180181 A1 | 9/2021 |
| WO | 2021185233 A1 | 9/2021 |
| WO | 2021190467 A1 | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021218110 A1 | 11/2021 |
| WO | 2021219072 A1 | 11/2021 |
| WO | 2021219090 A1 | 11/2021 |
| WO | 2021219091 A2 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A2 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |
| WO | 2021248083 A1 | 12/2021 |
| WO | 2021248090 A1 | 12/2021 |
| WO | 2021248095 A1 | 12/2021 |
| WO | 2021249563 A1 | 12/2021 |
| WO | 2021252339 A1 | 12/2021 |
| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |
| WO | 2022258974 A1 | 12/2022 |
| WO | 2023039240 A1 | 3/2023 |

OTHER PUBLICATIONS

Lanman et al., (2019) "Discovery of a Covalent Inhibitor of KRASG12C (AMG 510) for the Treatment of Solid Tumors", Journal of Medicinal Chemistry, 63(1):52-65.
Lech-Gustav et al., (2014) "The Renaissance of Ras", ACS Chemical Biology, 9(11):2447-2458.
Ledford, Heidi, (2015) "Cancer: The Ras Renaissance: Thirty years of pursuit have failed to yield a drug to take on one of the deadliest families of cancer-causing proteins. Now some researchers are taking another shot.", Nature, 520 (7547):278-280.
Lim et al., (2014) "Therapeutic Targeting of Oncogenic K-Ras by a Covalent Catalytic Site Inhibitor", Angewandte Chemie, 53(1):199-204.
Loncle et al., (2016) "The Pancreatitis-Associated Protein VMP1, a Key Regulator of Inducible Autophagy, Promotes Kras(G12D)-Mediated Pancreatic Cancer Initiation", Cell Death and Disease, 7(7):e2295 (7 pages).
Maegley et al., (Aug. 1996) "Ras-catalyzed Hydrolysis of GTP: a New Perspective From Model Studies", Proceedings of the National Academy of Sciences of the United States of America, 93(16):8160-8166.
Manchado et al., (2016) "A Combinatorial Strategy for Treating KRAS-mutant Lung Cancer", Nature, 534(7609):647-651.
Martin et al., (2019) "Characterising Covalent Warhead Reactivity", Bioorganic & Medicinal Chemistry, 27(10):2066-2074.
Matikas et al., (2017) "Targeting KRAS Mutated Non-small Cell Lung Cancer: A History of Failures and a Future of Hope for a Diverse Entity", Critical Reviews in Oncology/Hematology, 110:1-12.
Maurer et al., (Apr. 3, 2012) "Small-molecule Ligands Bind to a Distinct Pocket in Ras and Inhibit SOS-mediated Nucleotide Exchange Activity", Proceedings of the National Academy of Sciences of the United States of America, 109(14):5299-5304.
Ahmadian et al., (Jun. 1999) "Guanosine Triphosphatase Stimulation of Oncogenic Ras Mutants", 96(12):7065-7070.
McCormick, Frank, (2018) "Targeting KRAS Directly", Annual Review of Cancer Biology, 2:81-90.
Misale et al., (2019) "KRAS G12C Nsclc Models Are Sensitive to Direct Targeting of KRAS in Combination with PI3K Inhibition", Clinical Cancer Research, 25(2):796-807.
Muller et al., (2017) "Nucleotide Based Covalent Inhibitors of KRas Can Only Be Efficient in Vivo if They Bind Reversibly With GTP-like Affinity", Scientific Reports, 7(1):3687 (11 pages).

(56) References Cited

OTHER PUBLICATIONS

Nadal et al., (2013) "Abstract C141: KRAS G12C Mutation is Prognostic of Poor Outcome in Resected Lung Adenocarcinomas and Predictive of Poor Response to Mek Inhibition in Vitro", Molecular Cancer Therapeutics, 12(11_Supplement):C141.

Nassar et al., (Aug. 1996) "Ras/Rap Effector Specificity Determined by Charge Reversal", Nature Structural Biology, 3(8):723-729.

Niabet et al., (2018) "It Takes Two to Target: A Study in KRAS Dimerization", Biochemistry, 57(16):2289-2290.

Nussinov et al., (2016) "Independent and Core Pathways in Oncogenic KRAS Signaling", Expert Review of Proteomics, 13(8):711-716.

O'Bryan, John P., (2018) "Pharmacological Targeting of RAS: Recent Success With Direct Inhibitors", Pharmacological Research, 139:503-511.

Orlov et al., (2020) "Rapid Improvement of the Performance Status and Reduction of the Tumor Size in KRAS-Mutated Colorectal Cancer Patient Receiving Binimetinib, Hydroxychloroquine, and Bevacizumab", Case Reports in Oncology, 13(2):985-989.

Ostrem et al., (2016) "Direct Small-molecule Inhibitors of KRAS: From Structural Insights to Mechanism-based Design", Nature Reviews Drug Discovery, 15(11):771-785.

Ostrem et al., (Nov. 2013) "K-Ras(G12C) Inhibitors Allosterically Control GTP Affinity and Effector Interactions", Nature, 503(7477):548-551.

Pacold et al., (Dec. 8, 2000) "Crystal Structure and Functional Analysis of Ras Binding to Its Effector Phosphoinositide 3-Kinase Gamma", Cell, 103(6):931-943.

Palkowitz et al., (Mar. 16, 2017) "Synthesis of Diverse N-Acryloyl Azetidines and Evaluation of Their Enhanced Thiol Reactivities", Organic Letters, 19(9):2270-2273.

Pantsar et al., (Sep. 10, 2018) "Assessment of Mutation Probabilities of KRAS G12 Missense Mutants and Their Long-timescale Dynamics by Atomistic Molecular Simulations and Markov State Modeling", PLOS Computational Biology, 14(9):e1006458 (23 pages).

Papke et al., (2017) "Drugging RAS: Know the Enemy", Science, 355(6330):1158-1163.

Park et al., (2016) "The HSP90 Inhibitor, NVP-AUY922, Sensitizes KRAS-mutant Non-small Cell Lung Cancer With Intrinsic Resistance to MEK Inhibitor, Trametinib", Cancer Letters, 372(1):75-81.

Patricelli et al., (2016) "Selective Inhibition of Oncogenic KRAS Output with Small Molecules Targeting the Inactive State", Cancer Discovery, 6(3):316-329.

Perera et al., (Jul. 2016) "Oncogenic KRAS Triggers MAPK-dependent Errors in Mitosis and MYC-dependent Sensitivity to Anti-mitotic Agents", Scientific Reports, 6:29741 (15 pgaes).

Renaud, S et al., (2016) "KRAS in Non-Small-Cell Lung Cancer: Oncogenic Addiction and Epidermal Growth Factor Receptor Tyrosine Kinase Inhibitors", JAMA Oncology, 2(10):1373.

Riquelme et al., (2016) "Modulation of EZH2 Expression by MEK-ERK or PI3K-AKT Signaling in Lung Cancer Is Dictated by Different KRAS Oncogene Mutations", Cancer Research, 76(3):675-685.

Rooij et al., (1997) "Minimal Ras-binding Domain of Raf1 Can Be Used as an Activation-specific Probe for Ras", Oncogene, 14(5):623-625.

Ross et al., (2017) "Targeting KRAS-dependent Tumors With AZD4785, a High-affinity Therapeutic Antisense Oligonucleotide Inhibitor of KRAS", Science Translational Medicine, 9(394):eaal5253.

Rudoni et al., (2001) "Role of Guanine Nucleotides in the Regulation of the Ras/cAMP Pathway in *Saccharomyces cerevisiae*", Biochimica et Biophysica Acta, 1538(2-3):181-189.

Ruess et al., (2018) "Mutant KRAS-Driven Cancers Depend on PTPN11/SHP2 Phosphatase", Nature Medicine, 24(7):954-960.

Samatar et al., (2014) "Targeting RAS-ERK Signalling in Cancer: Promises and Challenges", Nature Reviews Drug Discovery, 13(12):928-942.

Ambrogio et al., (Mar. 2016) "Combined Inhibition of DDR1 and Notch Signaling is a Therapeutic Strategy for KRAS-driven Lung Adenocarcinoma", Nature Medicine, 22(3):270-277.

Sautier et al., (2016) "Latest Advances Towards Ras Inhibition: A Medicinal Chemistry Perspective", Angewandte Chemie International Edition, 55(52):15982-15988.

Scheffzek et al., (Jul. 1997) "The Ras-RasGAP Complex: Structural Basis for GTPAse Activation and Its Loss in Oncogenic Ras Mutants", Science, 277(5324):333-338.

Schwartz et al., (Jan. 7, 2014) "Covalent EGFR Inhibitor Analysis Reveals Importance of Reversible Interactions to Potency and Mechanisms of Drug Resistance", Proceedings of the National Academy of Sciences of the United States of America, 111(1):173-178.

Serafimova et al., (2012) "Reversible Targeting of Noncatalytic Cysteines With Chemically Tuned Electrophiles", Nature Chemical Biology, 8(5):471-476.

Serresi et al., (2016) "Polycomb Repressive Complex 2 Is a Barrier to KRAS-Driven Inflammation and Epithelial-Mesenchymal Transition in Non-Small-Cell Lung Cancer", Cancer Cell, 29(1):17-31.

Shaw et al., (May 24, 2011) "Selective Killing of K-ras Mutant Cancer Cells by Small Molecule Inducers of Oxidative Stress", PNAS, 108(21):8773-8778.

Shima et al., (May 14, 2013) "In Silico Discovery of Small-molecule Ras Inhibitors That Display Antitumor Activity by Blocking the Ras-effector Interaction", PNAS, 110(20):8182-8187.

Shima et al., (Jul. 16, 2010) "Structural Basis for Conformational Dynamics of GTP-bound Ras Protein", The Journal of Biological Chemistry, 285(29):22696-22705.

Shipman, Lydia, (2016) "Signalling: Putting the Brakes on KRAS-G12C Nucleotide Cycling", Nature Reviews Cancer, 16(3):127.

Simanshu et al., (2017) "RAS Proteins and Their Regulators in Human Disease", Cell, 170(1):17-33.

Singh et al., (Jun. 2, 2009) "A Gene Expression Signature Associated With "K-Ras Addiction" Reveals Regulators of EMT and Tumor Cell Survival", Cancer Cell, 15(6):489-500.

Skoulidis et al., (May 21, 2018) "STK11/LKB1 Mutations and PD-1 Inhibitor Resistance in KRAS-Mutant Lung Adenocarcinoma", Cancer Discovery, 8(7):822-835.

Eurasian Office Action issued in Eurasian Application No. 202390861, mailed on Jul. 16, 2024, 12 pages.

European Search Report issued in European Application No. 21867707.8, mailed on Aug. 14, 2024, 7 pages.

International Search Report and Written Opinion issued in International Application No. PCT/US2021/049940, mailed on Dec. 27, 2021, 9 pages.

"P01116 ■ Rask_Human, UniProtKB/Swiss-Prot", Retrieved on Sep. 23, 2024, 2024, 14 pages.

Alamgeer et al., (2013) "Novel Therapeutic Targets in Non-small Cell Lung Cancer", Current Opinion in Pharmacology, 13(3):394-401.

Caira, Minor., (1998) "Crystalline Polymorphism of Organic Compounds", Topics in Current Chemistry, 198:163-208.

Dogan et al., (2012) "Molecular Epidemiology of EGFR and KRAS Mutations in 3,026 Lung Adenocarcinomas: Higher Susceptibility of Women to Smoking-related Kras-mutant Cancers", Clinical Cancer Research, 18(22):6169-6177.

Fell et al., (2020) "Identification of the Clinical Development Candidate MRTX849, a Covalent KRASG12C Inhibitor for the Treatment of Cancer", Journal of Medicinal Chemistry, 63(13):6679-6693.

McCormick, Frank, (2015) "KRAS as a Therapeutic Target", Clinical Cancer Research, 21(8):1797-1801.

Santos et al., (1984) "Malignant Activation of a K-Ras Oncogene in Lung Carcinoma but Not in Normal Tissue of the Same Patient", Science, 223(4637):661-664.

Yu, Lian, (2001) "Amorphous Pharmaceutical Solids: Preparation, Characterization and Stabilization", Advanced Drug Delivery Reviews, 48(1):27-42.

Araki et al., (Nov. 11, 2011) "Solution Structure of the State 1 Conformer of GTP-bound H-Ras Protein and Distinct Dynamic Properties Between the State 1 and State 2 Conformers", Journal of Biological Chemistry, 286(45):39644-39653.

(56) References Cited

OTHER PUBLICATIONS

Bakalova et al., (2004) "Electronic Absorption and Emission Spectra and Computational Studies of Some 2-aryl, 2-styryl, and 2-(40-aryl)butadienyl Quinazolin-4-ones", Journal of Molecular Structure, 710: 229-234.
Barbie et al., (Nov. 5, 2009) "Systematic RNA Interference Reveals That Oncogenic KRAS-driven Cancers Require TBK1", Nature, 462(7269):108-112.
Blake et al., (Jun. 2014) "Discovery of 5,6,7,8-tetrahydropyrido[3,4-d]pyrimidine inhibitors of Erk2", Bioorganic & Medicinal Chemistry Letters, 24(12):2635-2639.
Broutin et al., (2016) "Insights Into Significance of Combined Inhibition of MEK and m-TOR Signalling Output in KRAS Mutant Non-small-cell Lung Cancer", British Journal of Cancer, 115(5):549-552.
Burgess et al., (Feb. 23, 2017) "KRAS Allelic Imbalance Enhances Fitness and Modulates MAP Kinase Dependence in Cancer", Cell, 168(5):817-829.
Burns et al., (Mar. 4, 2014) "Approach for Targeting Ras With Small Molecules That Activate SOS-mediated Nucleotide Exchange", PNAS, 111(9):3401-3406.
"International Search Report and Written Opinion for International Application No. PCT/US2018/061060", mailed on Feb. 7, 2019, 8 pages.
Cammarata, M. et al., (2016) "Impact of G12 Mutations on the Structure of K-Ras Probed by Ultraviolet Photodissociation Mass Spectrometry", Journal of the American Chemical Society, 138(40):13187-13196.
Canon et al., (Nov. 2019) "The Clinical KRAS(G12C) Inhibitor AMG 510 Drives Anti-Tumour Immunity", Nature, 575(7781):217-223 (26 pages).
Costa-Cabral et al., (Feb. 16, 2016) "CDK1 Is a Synthetic Lethal Target for KRAS Mutant Tumours", PLoS One, 11(2):e0149099 (22 pages).
Cox et al., (2003) "The Dark Side of Ras: Regulation of Apoptosis", Oncogene, 22(56):8999-9006.
Cully, Megan, (2016) "Closing the Door on KRAS-mutant Lung Cancer", Nature Reviews Drug Discovery, 15(11):747.
Dharmaiah et al., (Oct. 17, 2016) "Structural Basis of Recognition of Farnesylated and Methylated KRAS4b by PDEδ", Proceedings of the National Academy of Sciences of the United States of America, 113(44):E6766-E6775.
"PubChem-SID-132593111", Modify Date: May 31, 2019.
Fell et al., (Nov. 2018) "Discovery of Tetrahydropyridopyrimidines as Irreversible Covalent Inhibitors of Kras-G12C with In Vivo Activity", ACS Medicinal Chemistry Letters, 9(12):1230-1234.
Abe et al., (Feb. 2011) "Discovery of a Highly Potent and Selective MEK Inhibitor: GSK1120212 (JTP-74057 DMSO Solvate)", ACS Medicinal Chemistry Letters, 2(4):320-324.
Fiala, O. et al., (2013) "The Dominant Role of G12C Over Other KRAS Mutation Types in the Negative Prediction of Efficacy of Epidermal Growth Factor Receptor Tyrosine Kinase Inhibitors in Non-small Cell Lung Cancer", Cancer Genetics, 206(1-2):26-31.
Figueras et al., (2013) "The Impact of KRAS Mutations on VEGF-A Production and Tumour Vascular Network", BMC Cancer, 13:125 (11 pages).
Ford et al., (Jul. 8, 2005) "Structure of the G60A Mutant of Ras: Implications for the Dominant Negative Effect", Journal of Biological Chemistry, 280(27):25697-25705.
Grant et al., (Oct. 2011) "Novel Allosteric Sites on Ras for Lead Generation", PLoS One, 6(10):e25711 (10 pages).
Hall et al., (Sep. 17, 2002) "The Structural Basis for the Transition From Ras-GTP to Ras-GDP", Proceedings of the National Academy of Sciences of the United States of America, 99(19):12138-12142.
Hansen et al., (2018) "An Internally Controlled Quantitative Target Occupancy Assay for Covalent Inhibitors", Scientific Reports, 8(1):14312 (7 pages).
Hunter et al., (Jun. 17, 2014) "In Situ Selectivity Profiling and Crystal Structure of SML-8-73-1, an Active Site Inhibitor of Oncogenic K-Ras G12C", Proceedings of the National Academy of Sciences of the United States of America, 111(24):8895-8900.
Ihle et al., (Feb. 8, 2012) "Effect of KRAS Oncogene Substitutions on Protein Behavior: Implications for Signaling and Clinical Outcome", Journal of the National Cancer Institute, 104(3):228-239.
Ischenko et al., (2013) "Direct Reprogramming by Oncogenic Ras and Myc", PNAS, early edition 1, 110(10):3937-42.
Janes et al., (Jan. 25, 2018) "Targeting KRAS Mutant Cancers with a Covalent G12C-Specific Inhibitor", Cell, 172(3):578-589 (30 pages).
Jarvis, Lisa M., (Jun. 6, 2016) "Have Drug Hunters Finally Cracked KRas?", Chemical & Engineering News, 94(23):28-33.
Kamerkar, S. et al., (2017) "Exosomes Facilitate Therapeutic Targeting of Oncogenic KRAS in Pancreatic Cancer", Nature, 546(7659):498-503.
Karachaliou et al., (2013) "KRAS Mutations in Lung Cancer", Clinical Lung Cancer, 14(3):205-214.
Karnoub et al., (Jul. 2008) "Ras Oncogenes: Split Personalities", Nature Reviews Molecular Cell Biology, 9(7):517-531.
Kaufman, J. et al., (May 9, 2017) "Treatment of KRAS-Mutant Non-Small Cell Lung Cancer: The End of the Beginning for Targeted Therapies", JAMA, 317(18):1835-1837.
Kerr E. et al., (2016) "Mutant Kras Copy Number Defines Metabolic Reprogramming and Therapeutic Susceptibilities", Nature, 531(7592):110-113.
Kiel et al., (Jun. 22, 2004) "Electrostatically Optimized Ras-binding Ral Guanine Dissociation Stimulator Mutants Increase the Rate of Association by Stabilizing the Encounter Complex", PNAS, 101(25):9223-9228.
Kim, J. et al., (2017) "CPS1 Maintains Pyrimidine Pools and DNA Synthesis in KRAS/LKB1-Mutant Lung Cancer Cells", Nature, 546(7656):168-172.
Kim et al., (2016) "XPO1-dependent Nuclear Export is a Druggable Vulnerability in KRAS-mutant Lung Cancer", Nature, 538(7623):114-117.
Kitai et al., (2017) "Key Roles of EMT for Adaptive Resistance to MEK Inhibitor in KRAS Mutant Lung Cancer", Small GTPases, 8(3):172-176.
Kosloff, M. et al., (2003) "GTPase Catalysis by Ras and Other G-proteins: Insights From Substrate Directed Superimposition", Journal of Molecular Biology, 331(5):1157-1170.
Kotting et al., (Apr. 29, 2008) "The GAP Arginine Finger Movement Into the Catalytic Site of Ras Increases the Activation Entropy", PNAS, 105(17):6260-6265.
Smith et al., (Mar. 19, 2013) "NMR-based Functional Profiling of RASopathies and Oncogenic RAS Mutations", PNAS, 110(12):4574-4579.
Spoerner et al., (Apr. 24, 2001) "Dynamic Properties of the Ras Switch I Region and its Importance for Binding to Effectors", Proceedings of the National Academy of Sciences of the United States of Americ, 98(9):4944-4949.
Stephen et al., (Mar. 17, 2014) "Dragging Ras Back in the Ring", Cancer Cell, 25(3):272-281.
Sun et al., (2014) "A Method for the Second-Site Screening of K-Ras in the Presence of a Covalently Attached First-site Ligand", Journal of Biomolecular NMR, 60(1):11-14.
Sun et al., (2012) "Discovery of Small Molecules That Bind to K-Ras and Inhibit Sos-mediated Activation", Angewandte Chemie International Edition, 51(25):6140-6143.
Sunaga et al., (2011) "Knockdown of Oncogenic KRAS in Non-small Cell Lung Cancers Suppresses Tumor Growth and Sensitizes Tumor Cells to Targeted Therapy", Molecular Cancer Therapeutics, 10(2):336-346.
Sunaga et al., (2013) "Oncogenic KRAS-induced Epiregulin Overexpression Contributes to Aggressive Phenotype and is a Promising Therapeutic Target in Non-small-cell Lung Cancer", Oncogene, 32(34):4034-4042.
Sung et al., (1995) "Mutagenesis of the H-ras p21 at Glycine-60 Residue Disrupts GTP-Induced Conformational Change", Biochemistry, 34(10):3470-3477.
Suzawa et al., (Oct. 23, 2018) "Activation of KRAS mediates resistance to targeted therapy in MET exon 14 mutant non-small ell lung cancer", Clinical Cancer Research, 25(4):1248-1260.

(56) References Cited

OTHER PUBLICATIONS

Tanaka et al., (2010) "Interfering With RAS-effector Protein Interactions Prevent RAS-dependent Tumour Initiation and Causes Stop-start Control of Cancer Growth", Oncogene, 29(45):6064-6070.
Tape et al., (2016) "Oncogenic KRAS Regulates Tumor Cell Signaling via Stromal Reciprocation", Cell, 165(4):910-920 (12 pages).
Taylor et al., (2011) "Protein Kinases: Evolution of Synamic Regulatory Proteins", Trends in Biochemical Sciences, 36(2):65-77.
Thierry et al., (Apr. 2014) "Clinical Validation of the Detection of KRAS and BRAF Mutations From Circulating Tumor DNA", Nature Medicine, 20(4):430-435.
Tran et al., (Dec. 8, 2016) "T-Cell Transfer Therapy Targeting Mutant KRAS in Cancer", The New England Journal of Medicine, 375(23):2255-2262.
Walker et al., (Nov. 1999) "Structural Insights Into Phosphoinositide 3-Kinase Catalysis and Signalling", Nature, 402(6759):313-320.
Wang et al., (2017) "Ezh2 Acts as a Tumor Suppressor in Kras-driven Lung Adenocarcinoma", International Journal of Biological Sciences, 13(5):652-659.
Wang et al., (2013) "Targeting Mutant KRAS for Anticancer Therapeutics: A Review of Novel Small Molecule Modulators", Journal of Medicinal Chemistry, 56(13):5219-5230.
Welsch, et al., (2017) "Multivalent Small-Molecule Pan-RAS Inhibitors", Cell, 168(5):878-889.
Wijeratne et al., (2018) "Chemical Proteomic Characterization of a Covalent KRASG12C Inhibitor", ACS Medicinal Chemistry Letters, 9(6):557-562.
Winter, et al., (2015) "Small Molecule Binding Sites on the Ras:SOS Complex Can Be Exploited for Inhibition of Ras Activation", Journal of Medicinal Chemistry, 58(5):2265-2274.
Wood et al., (Jul. 21, 2016) "Reply", Comments & Response, Letters JAMA Oncology, American Medical Association.
Wood et al., (Apr. 21, 2016) "Prognostic and Predictive Value in KRAS in Non-Small-Cell Lung Cancer: A Review", JAMA Oncology, 2(6):805-812.
Xiong et al., (2016) "Development of Covalent Guanosine Mimetic Inhibitors of G12C KRAS", ACS Medicinal Chemistry Letters, 8(1):61-66.
Yen et al., (Oct. 8, 2018) "Pharmacological Induction of RAS-GTP Confers RAF Inhibitor Sensitivity in KRAS Mutant Tumors", Cancer Cell, 34(4):611-625.
Ambrogio et al., (Feb. 8, 2018) "KRAS Dimerization Impacts MEK Inhibitor Sensitivity and Oncogenic Activity of Mutant KRAS", Cell, 172(4):857-868.
Yuan et al., (Feb. 13, 2018) "Differential Effector Engagement by Oncogenic KRAS", Cell Reports, 22(7):1889-1902.
Zeng et al., (2001) "Design of Inhibitors of Ras-Raf Interaction Using a Computational Combinatorial Algorithm", Protein Engineering, 14(1):39-45.
Zhu et al., (Apr. 2014) "Inhibition of KRAS-driven Tumorigenicity by Interruption of an Autocrine Cytokine Circuit", Cancer Discovery, 4(4):452-465 (22 pages).
Ziemke et al., (Jan. 15, 2016) "Sensitivity of KRAS-Mutant Colorectal Cancers to Combination Therapy That Cotargets MEK and CDK4/6", Clinical Cancer Research, 22(2):405-414.
Zimmermann et al., (May 2013) "Small Molecule Inhibition of the KRAS-PDEdelta Interaction Impairs Oncogenic KRAS Signalling", Nature, 497(7451):638-642.

* cited by examiner

CRYSTALLINE FORMS OF A KRas G12C INHIBITOR

FIELD OF THE INVENTION

The present invention relates to crystalline forms of a KRas G12C inhibitor. In particular, the present invention relates to crystalline forms of the KRas G12C inhibitor 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, pharmaceutical compositions comprising the crystalline forms, processes for preparing the crystalline forms and methods of use thereof.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors regulating a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

The well-known role of KRas in malignancy and the discovery of these frequent mutations in KRas in various tumor types made KRas a highly attractable target of the pharmaceutical industry for cancer therapy. Notwithstanding thirty years of large scale discovery efforts to develop inhibitors of KRas for treating cancer, no KRas inhibitor has demonstrated sufficient safety and/or efficacy to obtain regulatory approval (e.g., see McCormick (2015) Clin Cancer Res. 21 (8):1797-1801).

Recently, irreversible, covalent inhibitors that target KRas G12C have been described (e.g., see Ostrem et al., (2013) Nature 503:548-551). For instance, commonly-owned and assigned U.S. Provisional Application Ser. No. 62/586,775 discloses potent, orally bioavailable compounds that irreversibly bind to KRas G12C for treating KRas G12C-mediated cancers.

A covalent, irreversible inhibitor of KRas G12C is 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, also known as MRTX849. An amorphous form of this compounds was described in International Patent Application PCT/US2018/061060 filed Nov. 14, 2018, published as WO2019/099524A1 on May 23, 2019 at Example 478, and in Fell et al., (2020) J. Med. Chem. 63, 6679-6693.

Process development for pharmaceutical compositions plays an important role for solid pharmaceutical compounds in balancing the desired pharmacological properties of the therapeutic agent. For example, identifying an appropriate crystalline forms and salt forms of the solid therapeutic agent can beneficially influence the dissolution rate, solubility, bioavailability, manufacturing, packaging and/or storage shelf life of the pharmaceutical composition. In addition, crystalline forms may be pressed into tablets for oral delivery as opposed to the need to use a capsule or spray-dry form for amorphous compounds.

For all the foregoing reasons, there is a need to produce a solid, crystalline salt form or salt forms of KRas G12C inhibitor, in particular the compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, that provides enhanced dissolution rate, solubility, bioavailability, manufacturing improvements and/or storage shelf life of the pharmaceutical composition. The present invention advantageously addresses one or more of those needs.

SUMMARY OF THE INVENTION

In one aspect of the invention, provided herein are crystalline forms of the KRas G12C inhibitor 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile.

In one embodiment, the crystalline form is designated crystalline Form A. In one embodiment, crystalline Form A has an X-ray powder diffraction pattern ("XRPD") comprising at least one characteristic peak at °2θ values selected from 8.6±0.2, 14.6±0.2, 16.9±0.2 and 18.3±0.2. In some embodiments only a single characteristic peak is present. In some embodiments two characteristic peaks are present. In some embodiments three characteristic peaks are present. In some embodiments four characteristic peaks are present.

In one embodiment, crystalline Form A has an X-ray powder diffraction pattern comprising peaks at °2θ values of 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

In another embodiment, crystalline Form A has an X-ray powder diffraction pattern comprising peaks at °2θ values of 5.8±0.2, 7.1±0.2, 8.6±0.2, 11.7±0.2, 12.3±0.2, 13.0±0.2, 14.2±0.2, 14.6±0.2, 16.0±0.2, 16.9±0.2, 17.2±0.2, 17.6±0.2, 17.9±0.2, 18.1±0.2, 18.3±0.2, 19.4±0.2, 19.9±0.2, 20.4±0.2, 20.7±0.2, 21.2±0.2, 21.4±0.2, 21.8±0.2, 22.7±0.2, 23.0±0.2, 23.5±0.2, 23.9±0.2, 24.9±0.2, 25.5±0.2, 26.2±0.2, 26.4±0.2, 27.2±0.2, 28.0±0.2, 28.2±0.2 and 29.6±0.2.

In another embodiment, crystalline Form A has an X-ray powder diffraction pattern comprising two or more peaks at °2θ at 8.6±0.2, 14.6±0.2, 16.9±0.2 and 18.3±0.2.

In other embodiments, crystalline Form A has an XRPD pattern substantially as shown in FIG. 1A or FIG. 1B.

In one embodiment, crystalline Form A is characterized by having an endothermic peak onset at about 107° C. with a heat of fusion of 46 J/g as measured by differential scanning calorimetry ("DSC"). In another embodiment, crystalline Form A has a DSC thermogram substantially as shown in FIG. 2.

In one embodiment, crystalline Form A is characterized by having an endothermic peak onset at about 119° C. with a heat of fusion of 58 J/g as measured by differential scanning calorimetry ("DSC"). In another embodiment, crystalline Form A has a DSC thermogram substantially as shown in FIG. 11.

In another embodiment, Form A has both: 1) one or more DSC characteristics described above; and 2) an X-ray powder diffraction pattern comprising at least one peak at °2θ selected from 8.6±0.2, 14.6±0.2, 16.9±0.2 and 18.3±0.2.

In another embodiment, Form A has both: 1) one or more DSC characteristics described above; and 2) an X-ray powder diffraction pattern comprising at least one peak at °2θ selected from 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

In one embodiment, crystalline Form A is characterized by having negligible weight loss until the onset of degradation at about 200° C. as measured by thermogravimetric analysis ("TGA"). In another embodiment, crystalline Form A has a TGA profile substantially as shown in FIG. 3.

In another embodiment, Form A has both: 1) one or more TGA characteristics described above; and 2) an X-ray powder diffraction pattern comprising at least one peak at °2θ selected from 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2. In another embodiment, Form A has both: 1) one or more TGA characteristics described above; and 2) an X-ray powder diffraction pattern comprising at least one peak at °2θ selected from 8.6±0.2, 14.6±0.2, 16.9±0.2 and 18.3±0.2.

In one embodiment, crystalline Form A is characterized by having an observed weight gain from about 0.1% at 40% RH to 0.6% at 90% RH, fully lost upon desorption to 0% RH. Cycles repeat show little to no hysteresis, as measured by dynamic vapor sorption ("DVS").

In another embodiment, crystalline Form A has a DVS isotherm substantially as shown in FIG. 4.

In another embodiment, Form A has both: 1) one or more DVS characteristics described above; and 2) an X-ray powder diffraction pattern comprising at least one peak at °2θ selected from 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

In another embodiment, Form A has both: 1) one or more DVS characteristics described above; and 2) an X-ray powder diffraction pattern comprising at least one peak at °2θ selected from 8.6±0.2, 14.6±0.2, 16.9±0.2 and 18.3±0.2.

In one embodiment, crystalline Form A is substantially free of residual organic solvents.

In one embodiment, the crystalline form is designated crystalline Form B.

In one embodiment, crystalline Form B has an X-ray powder diffraction pattern comprising at least one characteristic peak at °2θ values selected from 16.7±0.2, 17.5±0.2 and 18.8±0.2. In some embodiments only a single characteristic peak is present. In some embodiments two characteristic peaks are present. In some embodiments three characteristic peaks are present.

In one embodiment, crystalline Form B has an X-ray powder diffraction pattern comprising peaks at °2θ values of 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In another embodiment, crystalline Form B has an X-ray powder diffraction pattern comprising peaks at °2θ values of 5.8±0.2, 9.1±0.2, 11.2±0.2, 11.6±0.2, 12.3±0.2, 13.0±0.2, 13.3±0.2, 13.6±0.2, 13.9±0.2, 14.2±0.2, 14.5±0.2, 15.3±0.2, 15.6±0.2, 15.9±0.2, 16.7±0.2, 17.5±0.2, 17.9±0.2, 18.1±0.2, 18.4±0.2, 18.8±0.2, 19.5±0.2, 19.9±0.2, 20.4±0.2, 21.4±0.2, 21.8±0.2, 22.6±0.2, 23.1±0.2, 23.4±0.2, 23.7±0.2, 24.0±0.2, 24.3±0.2, 24.7±0.2, 25.1±0.2, 25.6±0.2, 25.8±0.2, 26.3±0.2, 26.7±0.2, 27.3±0.2, 27.6±0.2, 28.6±0.2, 29.4±0.2, 29.7±0.2 and 30.0±0.2.

In another embodiment, crystalline Form B has an X-ray powder diffraction pattern comprising two or more peaks at °2θ at 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In another embodiment, crystalline Form B has XRPD pattern substantially as shown in FIG. 5A or in FIG. 5B.

In another embodiment, crystalline Form B as measured by DSC as shown in FIG. 12 is characterized by having an endothermic peak onset at about 122° C. and a heat of fusion of 61 J/g.

In one embodiment, crystalline Form B as measured by DSC is characterized by having an endothermic peak onset at about 109° C. with a heat of fusion of 49 J/g. In one embodiment, crystalline Form B has a DSC thermogram substantially as shown in FIG. 6.

In another embodiment, Form B has both: 1) one or more DSC characteristics described above; and 2) an X-ray powder diffraction pattern comprising at least one peak at °2θ selected from 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In one embodiment, crystalline Form B as measured by TGA is characterized by having a 0.6% weight loss from 25 to 150° C. with no further events until degradation onset at ~200° C. In another embodiment, crystalline Form B has a TGA profile substantially as shown in FIG. 7.

In another embodiment, Form B has both: 1) one or more TGA characteristics described above; and 2) an X-ray powder diffraction pattern comprising at least one peak at °2θ selected from 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In one embodiment, crystalline Form B as measured by DVS as shown in FIG. 8 is characterized by having a weight gain from about 0.6% at 60% RH to 2.9% at 70% RH, further increasing to 2.5% at 90% RH. Following a weight loss to 2.2% from 90% RH to 70% RH, a rapid weight loss is observed from 70 to 50% RH with a weight change from 2.2% to 0.4%. Constant gentle decrease in weight to 0% from 50 to 0% RH is observed. Cycles repeat showing little hysteresis.

In another embodiment, Form B has both: 1) one or more DVS characteristics described above; and 2) an X-ray powder diffraction pattern comprising at least one peak at °2θ selected from 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In one embodiment, crystalline Form B is substantially free of residual organic solvents.

In one embodiment, the crystalline form is designated crystalline Form C.

In one embodiment, crystalline Form C has an X-ray powder diffraction pattern comprising at least one characteristic peak at °2θ value selected from 16.4±0.2 and 19.7±0.2. In some embodiments only a single characteristic peak is present. In some embodiments two characteristic peaks are present.

In one embodiment, crystalline Form C has an X-ray powder diffraction pattern comprising peaks at °2θ values of 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

In one embodiment, crystalline Form C has an X-ray powder diffraction pattern comprising peaks at °2θ values of 5.7±0.2, 9.0±0.2, 11.0±0.2, 11.3±0.2, 12.3±0.2, 13.3±0.2, 13.9±0.2, 14.2±0.2, 15.1±0.2, 15.5±0.2, 15.8±0.2, 16.4±0.2, 17.1±0.2, 17.3±0.2, 17.8±0.2, 18.0±0.2, 18.4±0.2, 18.6±0.2, 19.3±0.2, 19.7±0.2, 21.1±0.2, 21.5±0.2, 21.8±0.2, 22.1±0.2, 22.8±0.2, 23.1±0.2, 23.2±0.2, 23.6±0.2, 23.7±0.2, 24.4±0.2, 24.7±0.2, 25.2±0.2, 26.3±0.2, 26.7±0.2, 27.2±0.2, 28.1±0.2, 29.0±0.2, 29.4±0.2 and 29.8±0.2.

In one embodiment, crystalline Form C has an X-ray powder diffraction pattern comprising two or more peaks at °2θ values at 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

In another embodiment, crystalline Form C has XRPD pattern substantially as shown in FIG. 9.

In one embodiment, crystalline Form C as measured by DSC is characterized by having a small endothermic peak onset about 58° C. and a strong endothermic peak onset at about 118° C. In one embodiment, crystalline Form C has a DSC thermogram substantially as shown in FIG. 10.

In another embodiment, Form C has both: 1) one or more DSC characteristics described above; and 2) an X-ray powder diffraction pattern comprising at least one peak at °2θ selected from 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

In one embodiment, crystalline Form C as measured by TGA is characterized by having a stepwise loss of mass of about 1.2% from about 45° C. to about 86° C. until the onset of degradation at about 260° C. In another embodiment, crystalline Form C has a TGA profile substantially as shown in FIG. 10.

In another embodiment, Form C has both: 1) one or more TGA characteristics described above; and 2) an X-ray powder diffraction pattern comprising at least one peak at °2θ selected from 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

In one embodiment, crystalline Form C is a hydrate.

In one embodiment, the crystalline form is designated crystalline Form D.

In one embodiment, crystalline Form D has an X-ray powder diffraction pattern comprising at least one characteristic peak.

In one embodiment, crystalline Form D has an X-ray powder diffraction pattern comprising a characteristic peak at a °2θ value of 4.4±0.2.

In another embodiment, crystalline Form D has an X-ray powder diffraction pattern comprising peaks at °2θ values of 4.4±0.2, 13.6±0.2, 13.8±0.2, 15.2±0.2, 16.3±0.2, 17.7±0.2, 18.0±0.2, 20.9±0.2, 22.6±0.2, 23.0±0.2, and 27.6±0.2.

In one embodiment, crystalline Form D has an X-ray powder diffraction pattern comprising peaks at °2θ values of 4.4±0.2, 8.9±0.2, 10.0±0.2, 11.2±0.2, 12.3±0.2, 12.7±0.2, 13.4±0.2, 13.6±0.2, 13.8±0.2, 14.3±0.2, 15.2±0.2, 16.1±0.2, 16.3±0.2, 16.9±0.2, 17.7±0.2, 18.0±0.2, 18.6±0.2, 19.2±0.2, 20.1±0.2, 20.9±0.2, 21.2±0.2, 21.8±0.2, 22.6±0.2, 23.0±0.2, 23.5±0.2, 24.2±0.2, 24.7±0.2, 25.2±0.2, 26.1±0.2, 26.3±0.2, 27.2±0.2, 27.6±0.2, 27.9±0.2, 28.3±0.2, 29.0±0.2 and 29.2±0.2.

In one embodiment, crystalline Form D has an X-ray powder diffraction pattern comprising two or more peaks at °2θ value at 4.4±0.2, 13.6±0.2, 13.8±0.2, 15.2±0.2, 16.3±0.2, 17.7±0.2, 18.0±0.2, 20.9±0.2, 22.6±0.2, 23.0±0.2, and 27.6±0.2.

In another embodiment, crystalline Form D has XRPD pattern substantially as shown in FIG. 13.

In one embodiment, crystalline Form D is characterized by having an endothermic peak with a maximum at about 84° C. and another endothermic peak with a maximum at about 110° C. by differential scanning calorimetry.

In one embodiment, crystalline Form D has a DSC thermogram substantially as shown in FIG. 14.

In another embodiment, crystalline Form D has both: 1) one or more DSC characteristics described above; and 2) an X-ray powder diffraction pattern comprising at least one peak at °2θ selected from 4.4±0.2, 13.6±0.2, 13.8±0.2, 15.2±0.2, 16.3±0.2, 17.7±0.2, 18.0±0.2, 20.9±0.2, 22.6±0.2, 23.0±0.2, and 27.6±0.2.

In one embodiment, crystalline Form D as measured by TGA is characterized by having a stepwise loss of mass of about 4.3% from about 45° C. to about 116° C. until the onset of degradation at about 260° C.

In another embodiment, crystalline Form D has a TGA profile substantially as shown in FIG. 14. In one embodiment, crystalline Form D is a hydrate.

In another embodiment, crystalline Form D has both: 1) one or more TGA characteristics described above; and 2) an X-ray powder diffraction pattern comprising at least one peak at °2θ selected from 4.4±0.2, 13.6±0.2, 13.8±0.2, 15.2±0.2, 16.3±0.2, 17.7±0.2, 18.0±0.2, 20.9±0.2, 22.6±0.2, 23.0±0.2, and 27.6±0.2.

In one embodiment, the crystalline form is designated crystalline Form E.

In one embodiment, crystalline Form E has an X-ray powder diffraction pattern comprising at least one characteristic peak.

In one embodiment, crystalline Form E has an X-ray powder diffraction pattern comprising at least one characteristic peak at °2θ values selected from 5.2±0.2 and 10.2±0.2. In some embodiments only a single characteristic peak is present. In some embodiments two characteristic peaks are present.

In one embodiment, crystalline Form E has an X-ray powder diffraction pattern comprising peaks at °2θ values of 5.2±0.2, 10.2±0.2, 11.8±0.2, 13.5±0.2, 14.3±0.2, 16.9±0.2, 17.7±0.2, 20.3±0.2, 20.5±0.2, 21.9±0.2.

In one embodiment, crystalline Form E has an X-ray powder diffraction pattern comprising peaks at °2θ values of 5.2±0.2, 9.2±0.2, 10.2±0.2, 11.2±0.2, 11.8±0.2, 13.5±0.2, 14.3±0.2, 15.4±0.2, 16.4±0.2, 16.9±0.2, 17.7±0.2, 18.0±0.2, 19.4±0.2, 20.3±0.2, 20.5±0.2, 21.0±0.2, 21.3±0.2, 21.9±0.2, 22.4±0.2, 22.7±0.2, 23.1±0.2, 23.8±0.2, 24.2±0.2, 25.7±0.2, 26.8±0.2, 27.2±0.2, 27.4±0.2, 27.9±0.2, 28.6±0.2 and 29.0±0.2.

In one embodiment, crystalline Form E has an X-ray powder diffraction pattern comprising two or more peaks at °2θ value at 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

In another embodiment, crystalline Form E has an XRPD pattern substantially as shown in FIG. 15.

In one embodiment, crystalline Form E as measured by DSC is characterized by having an endothermic peak onset at about 99° C. and a heat of fusion of 47 J/g.

In one embodiment, crystalline Form E has a DSC thermogram substantially as shown in FIG. 16.

In another embodiment, crystalline Form E has both: 1) one or more DSC characteristics described above; and 2) an X-ray powder diffraction pattern comprising at least one peak at °2θ selected from 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

In one embodiment, crystalline Form E as measured by TGA is characterized by having negligible loss of mass for crystalline Form E up to about 94° C. through the onset of degradation at about 240° C.

In another embodiment, crystalline Form E has a TGA profile substantially as shown in FIG. 17.

In another embodiment, crystalline Form E has both: 1) one or more TGA characteristics described above; and 2) an X-ray powder diffraction pattern comprising at least one peak at °2θ selected from 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

In one embodiment, crystalline Form E as measured by DVS is characterized by having a gradual weight gain of 1.2% between 5% to 95% RH. During desorption, the weight gained was lost with some hysteresis.

In another embodiment, crystalline Form E has a DVS isotherm substantially as shown in FIG. 18.

In another embodiment, crystalline Form E has both: 1) one or more DVS characteristics described above; and 2) an X-ray powder diffraction pattern comprising at least one peak at °2θ selected from 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

In one embodiment, crystalline Form E is substantially free of residual organic solvents.

Amorphous 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile free base has an XRPD pattern substantially as shown in FIG. 19, and a modulated DSC thermogram substantially as shown in FIG. 20.

In another embodiment, a mixture of crystalline Forms A and B have an XRPD pattern substantially as shown in the bottom trace of FIG. 21.

In one embodiment, the crystalline forms of the present invention are at least 40%, 50%, 60%, 70%, 80%, 90% or 95% crystalline.

In another aspect of the invention, pharmaceutical compositions are provided for use in the methods comprising a therapeutically effective amount of a crystalline form of the KRas G12C inhibitor 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, or a pharmaceutically acceptable salt thereof and/or a pharmaceutically acceptable excipient.

In one embodiment, the crystalline form is Form A. In another embodiment, the crystalline form is Form B. In one embodiment, the crystalline form is Form C. In another embodiment, the crystalline form is Form D. In one embodiment, the crystalline form is Form E. In one embodiment, the crystalline form is a mixture of any two or more of Forms A-E. In another embodiment, the crystalline form is a mixture of any two or more of Forms A-E with the amorphous form.

In one embodiment, the pharmaceutical compositions of the present invention contain 95% of a crystalline form of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile or salts thereof. In one embodiment, the pharmaceutical compositions of the present invention contain at least 95% of a crystalline form. In one embodiment, the pharmaceutical compositions of the present invention contain at least 90% of a crystalline form. In another embodiment, the pharmaceutical compositions of the present invention contain at least 80% of a crystalline form. In other embodiments, the pharmaceutical compositions of the present invention contain at least 70% of a crystalline form. In one embodiment, the pharmaceutical compositions of the present invention contain at least 60% of a crystalline form. In another embodiment, the pharmaceutical compositions of the present invention contain at least 50% of a crystalline form. In one embodiment, the crystalline form is Form A. In another embodiment, the crystalline form is Form B. In one embodiment, the crystalline form is Form C. In another embodiment, the crystalline form is Form D. In one embodiment, the crystalline form is Form E. In one embodiment, the crystalline form is a mixture of any two or more of Forms A-E. In another embodiment, the crystalline form is a mixture of any two or more of Forms A-E with the amorphous form.

In one aspect of the invention, provided herein are methods for inhibiting KRas G12C activity in a cell, comprising contacting the cell in which inhibition of KRas G12C activity is desired with a therapeutically effective amount of a crystalline form of the present invention, alone or in combination with one or more pharmaceutically acceptable excipients and/or diluents. In one embodiment, the crystalline form is Form A. In another embodiment, the crystalline form is Form B. In one embodiment, the crystalline form is Form C. In another embodiment, the crystalline form is Form D. In one embodiment, the crystalline form is Form E. In one embodiment, the crystalline form is a mixture of any two or more of Forms A-E. In another embodiment, the crystalline form is a mixture of any two or more of Forms A-E with the amorphous form.

In one aspect of the invention, provided herein are methods of treating cancer in a subject in need thereof, comprising administering to the subject a therapeutically effective amount of a crystalline form of KRAS G12C inhibitor of the present invention. In one embodiment, the cancer is a KRas G12C-associated cancer. In one embodiment, the KRas G12C-associated cancer is lung cancer. In one embodiment, the crystalline form is Form A. In another embodiment, the crystalline form is Form B. In one embodiment, the crystalline form is Form C. In another embodiment, the crystalline form is Form D. In one embodiment, the crystalline form is Form E. In one embodiment, the crystalline form is a mixture of any two or more of Forms A-E. In another embodiment, the crystalline form is a mixture of any two or more of Forms A-E with the amorphous form.

Also provided herein are methods for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of crystalline form of KRAS G12C inhibitor of the present invention or salts thereof, alone or in combination with one or more pharmaceutically acceptable excipients and/or diluent. In one embodiment, the crystalline form is Form A. In another embodiment, the crystalline form is Form B. In one embodiment, the crystalline form is Form C. In another embodiment, the crystalline form is Form D. In one embodiment, the crystalline form is Form E. In one embodiment, the crystalline form is a mixture of any two or more of Forms A-E. In another embodiment, the crystalline form is a mixture of any two or more of Forms A-E with the amorphous form.

In one embodiment, the subject is an adult patient. In one embodiment, the subject is a pediatric patient.

In some embodiments of any of the methods described herein, before treatment with the compositions or methods of the invention, the patient was treated with one or more of a chemotherapy, a targeted anticancer agent, radiation therapy, and surgery, and optionally, the prior treatment was unsuccessful; and/or the patient has been administered surgery and optionally, the surgery was unsuccessful; and/or the patient has been treated with a platinum-based chemotherapeutic agent, and optionally, the patient has been previously determined to be non-responsive to treatment with the platinum-based chemotherapeutic agent; and/or the patient has been treated with a kinase inhibitor, and optionally, the prior treatment with the kinase inhibitor was unsuccessful; and/or the patient was treated with one or more other therapeutic agent(s).

In another aspect of the invention, provided herein are process for the preparation of crystalline forms of the KRas G12C inhibitor. In one embodiment, the process describes the preparation of crystalline Form A. In one embodiment, the process describes the preparation of crystalline Form B. In one embodiment, the process describes the preparation of crystalline Form C. In one embodiment, the process describes the preparation of crystalline Form D. In one embodiment, the process describes the preparation of crystalline Form E.

DETAILED DESCRIPTION OF THE INVENTION

Figure 1A:
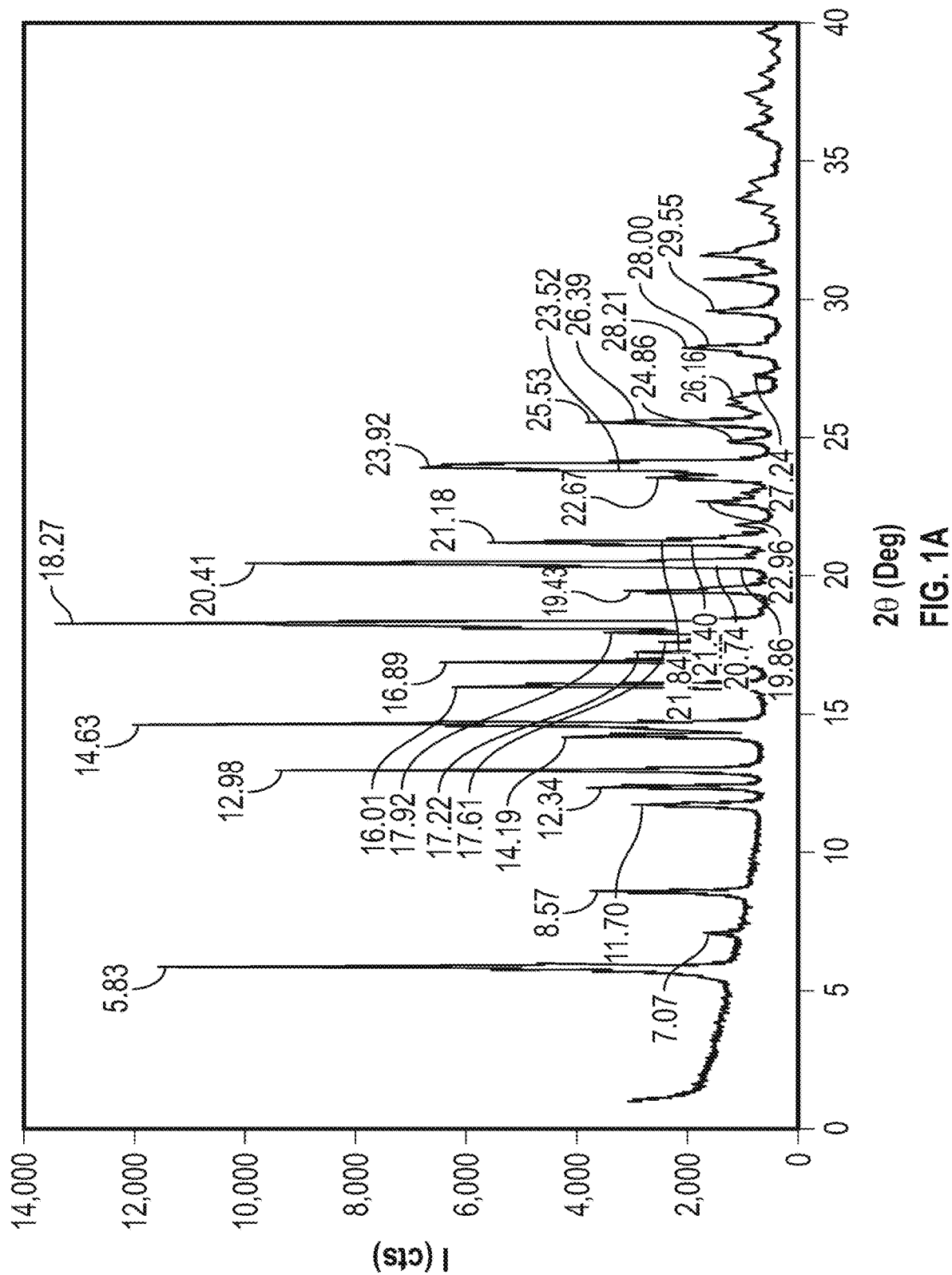
FIG. 1A and FIG. 1B illustrate X-ray powder diffraction (XRPD) patterns of crystalline Form A free base 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, according to Examples 1A and 1B respectively.

The present invention relates to crystalline forms of the KRas G12C inhibitor 2-[(2S)-4-[7-(8-chloro-1-naphthyl)-2-

[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile and a crystalline form of a pharmaceutically acceptable salt thereof. In particular, the present invention relates to crystalline forms of the KRas G12C inhibitor 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, pharmaceutical compositions comprising the crystalline forms, processes for preparing the crystalline forms and methods of use thereof.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to the KRas G12C inhibitor of the present invention: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile and a novel salt thereof as described herein. This compound is capable of negatively modulating or inhibiting all or a portion of the enzymatic activity of KRas G12C. The KRas G12C inhibitor of the present invention interacts with and irreversibly bind to KRas G12C by forming a covalent adduct with the sulfhydryl side chain of the cysteine residue at position 12 resulting in the inhibition of the enzymatic activity of KRas G12C.

As used herein, the term "Form A" or "crystalline Form A" when used alone refers to 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form A.

As used herein, the term "Form B" or "crystalline Form B" when used alone refers to 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form B.

As used herein, the term "Form C" or "crystalline Form C" when used alone refers to 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form C.

As used herein, the term "Form D" or "crystalline Form D" when used alone refers to 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form D.

As used herein, the term "Form E" or "crystalline Form E" when used alone refers to 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form E.

As used herein, the term "solvate" refers to a crystalline form of the KRas G12C inhibitor which contains solvent.

As used herein, the term "hydrate" refers to a solvate wherein the solvent comprises water.

As used herein, the term "residual organic solvents" refers to organic volatile chemicals used or produced during the crystallization/manufacturing processes that are not completely removed during the manufacturing technique.

As used herein, the term "substantially free of residual organic solvents" means that the manufactured pharmaceutical preparation, e.g., a pharmaceutical preparation comprising a crystalline form of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile or a crystalline form of a salt thereof, contains less than 1.0% by weight of residual organic solvents, contains less than 0.5% by weight of residual organic solvents, contains less than 0.4% by weight of residual organic solvents, contains less than 0.3% by weight of residual organic solvents, contains less than 0.2% by weight of residual organic solvents, or contains less than 0.1% by weight of residual organic solvents.

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994.

In some embodiments of any of the methods or uses described herein, an assay is used to determine whether the patient has KRas G12C mutation using a sample (e.g., a biological sample or a biopsy sample such as a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR, quantitative real-time RT-PCR, allele-specific genotyping or ddPCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

As used herein, a "therapeutically effective amount" of a crystalline form of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile or salt thereof is an amount that is sufficient to ameliorate, or in some manner reduce a symptom or stop or reverse progression of a condition, or negatively modulate or inhibit the activity of KRas G12C. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, the term "about" when used to modify a numerically defined parameter (e.g., the dose of a crystalline form of the KRAS inhibitor detailed herein or a crystalline form of a pharmaceutically acceptable salt thereof, or the length of treatment time described herein) means that the parameter may vary by as much as 10% below or above the stated numerical value for that parameter. For example, a dose of about 5 mg/kg may vary between 4.5 mg/kg and 5.5 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg. Likewise, about 5% or more, 10% or more, 15% or more, 20% or more, and 25% or more means about 5% or more, about 10% or more, about 15% or more, about 20% or more, and about 25% or more.

As used herein, the term "about" when used in reference to XRPD peak positions refers to the inherent variability of peaks depending on the calibration of the instrument, processes used to prepare the crystalline forms of the present invention, age of the crystalline forms and the type of instrument used in the analysis. The variability of the instrumentation used for XRPD analysis was about +−0.2° 2θ.

General Methods and Instrumentation

The general methods outlined below were used in the exemplified Examples, unless otherwise noted.

Crystalline forms may be analyzed using any suitable analytical method or assay procedure including, but not limited to, X-Ray Powder Diffraction, NMR, differential scanning calorimetry, thermo-gravimetric analysis, and gravimetric vapor sorption to assure formation of the preferred crystalline form of the KRas G12C inhibitor. The crystalline form is typically produced in an amount of greater that 50% by weight isolated yield, greater that 60% by weight isolated yield, greater that 70% by weight isolated yield, greater that 80% by weight isolated yield, greater that 90% by weight isolated yield or greater that 95% by weight isolated yield.

In one embodiment, the crystalline forms of the present invention are at least 40%, 50%, 60%, 70%, 80%, 90% or 95% crystalline.

I. X-Ray Powder Diffraction (XRPD)

X-Ray Powder Diffraction pattern (diffractograms) analysis was conducted using a PANalytical X'Pert Pro MPD diffractometer using an incident beam of Cu Kα radiation produced in a long fine focused source and a nickel, and in accordance with the manufacturer's instructions. The diffractometer was configured using the symmetric Bragg-Brentano geometry.

Prior to analysis, a silicon specimen (NIST SRM 640e) was analyzed to verify the observed position of the Si 111 peak is consistent with NIST-certified position Typically, a specimen of the sample was prepared as a thin, circular layer center on a silicon zero-background substrate. Anti-scatter slits (SS) were used to minimize the background generated by air. Soller slits for the incident and diffracted beams to minimize broadening from axial divergence. Diffraction patterns were collected using a scanning position-sensitive detector (X'Celerator) located 240 mm from the sample. The software used for data collection and analysis was Data Collector Software, v. 5.5.

II. Differential Scanning Calorimetry (DSC)

For certain samples, Differential Scanning Calorimetry (DSC) analysis was conducted using a Mettler-Toledo DSC3+ differential scanning calorimeter according to the manufacturer's instructions. A tau lag adjustment was performed using indium, tin and zinc. The temperature and enthalpy were adjusted using octane, phenyl salicylate, indium, tin and zinc.

Typically each sample was placed in a hermetically sealed aluminium DSC pan, the sample was weighed and the lid was pierced, and inserted into the DSC cell. A second aluminum DSC pan of the same weight was configured as the sample pan for the reference side of the cell, and the lid was pierced. Data were collected from 25° C. to 350° C. at 10° C./min.

For certain other samples DSC data were collected on a TA Instruments Q2000 equipped with a 50 position auto-sampler. Typically, 0.5-3 mg of each sample, in a pin-holed aluminium pan, was heated at 10° C./min from 25° C. to 300° C. A purge of dry nitrogen at 50 ml/min was maintained over the sample. Modulated temperature DSC was carried out using an underlying heating rate of 2° C./min and temperature modulation parameters of 0.636° C. (amplitude) every 60 seconds (period). The instrument control software was Advantage for Q Series and Thermal Advantage and the data were analysed using Universal Analysis.

In still other samples, DSC data were collected on a TA Instruments Discovery DSC equipped with a 50 position auto-sampler. Typically, 0.5-3 mg of each sample, in a pin-holed aluminium pan, was heated at 10° C./min from 25° C. to ~300° C. A purge of dry nitrogen at 50 ml/min was maintained over the sample. The instrument control software was TRIOS and the data were analysed using TRIOS or Universal Analysis.

Routine variations on the above techniques could be implemented by a skilled practitioner.

III. Thermo-Gravimetric Analysis (TGA)

TGA analysis or combined DSC/TGA analysis was performed using a Mettler-Toledo TGA/DSC3+ analyzer according to the manufacturer's instructions. The temperature and enthalpy were adjusted using indium, tin and zinc, and verified using indium. The balance was verified using calcium oxalate. Typically, each sample was loaded into an open aluminium DSC pan, the pan was hermetically sealed, the lid was pierced, the pan was inserted into the TGA furnace and heated at 10° C./min from ambient temperature to 350° C. under a nitrogen purge.

IV. Dynamic Vapor Sorption (DVS)

Vapor Sorption isotherms were obtained using a Surface Measurement System (SMS) DVS Intrinsic moisture sorption analyzer, controlled by DVS Intrinsic Control software. Samples were not dried prior to analysis. Sorption and desorption data were collected over a range of 5%-95% relative humidity (RH) at 10% RH increments under a nitrogen purge. The equilibrium criterion used for analysis was less than 0.0100% weight change in 5 minutes with a maximum equilibration time of 3 hours.

VI. Polarized Light Microscopy

Crystal formation was observed using polarized light microscopy. Light microscopy was performed using a Leica DMLP Compound Polarizing Light Microscope, equipped with a Spot Insight Color Camera. Each sample was placed on a glass slide, a cover glass was placed over the sample, and a drop of mineral oil typically was added to cover the sample by capillarity. Images were acquired at ambient temperature using Spot Advance Software Version 4.5.9, built Jun. 9, 2005.

VII. Nuclear Magnetic Resonance

Solution NMR spectra were acquired using an Avance 600 MHz NMR spectrometer according to the manufacturer's instructions. Sample were prepare by solving about 5-10 mg of sample in DMSO d6-containing TMS.

KRAS G12C Inhibitor

In one aspect of the invention, provided herein are crystalline forms of the KRAS G12C inhibitor 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, also known as MRTX849.

As noted above, methods for manufacturing the KRas G12C inhibitor disclosed herein are known. For example, International Patent Application PCT/US2018/061060 filed Nov. 14, 2018, published as WO2019/099524A1 on May 23, 2019, and the related US application publication number US2019014444 describes suitable intermediates and general reaction schemes for preparing KRas G12C inhibitors, and also provides a detailed synthetic route for the preparation of amorphous 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile in Example 478. Methods for preparing crystalline forms of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile are provided herein.

Crystalline Forms of the KRAS G12C Inhibitor

Exemplary methods for preparing crystalline Form A through Form E are described in Examples 1-5, respectively.

Figure 19:
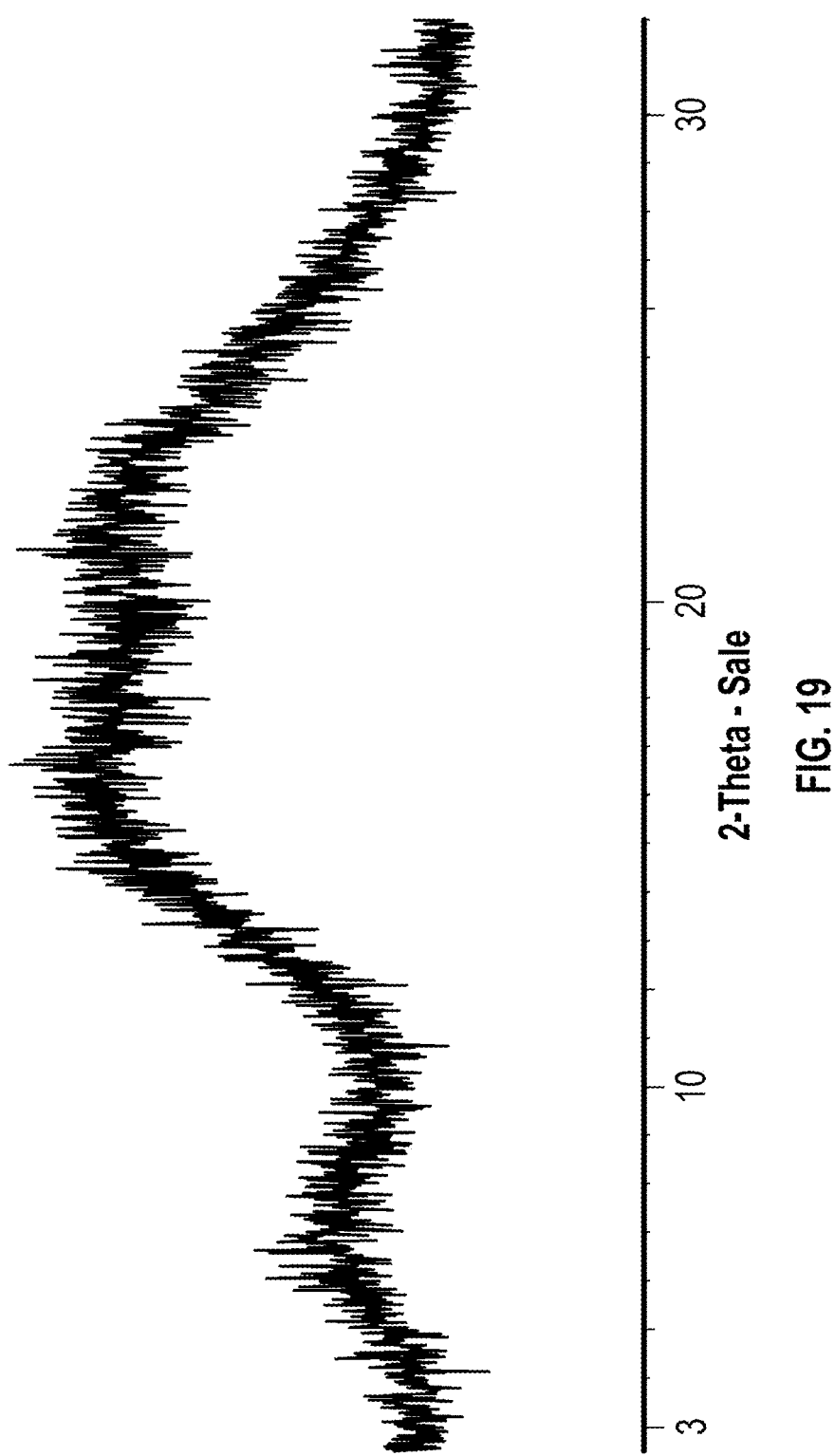
FIG. 19 illustrates an X-ray powder diffraction (XRPD) pattern of amorphous free base 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile.

The X-ray powder diffraction pattern ("XRPD") of the amorphous free base of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile is shown in FIG. 19. As shown in FIG. 19, the XRPD pattern of the amorphous free base lacks any characteristic peaks.

Figure 20:
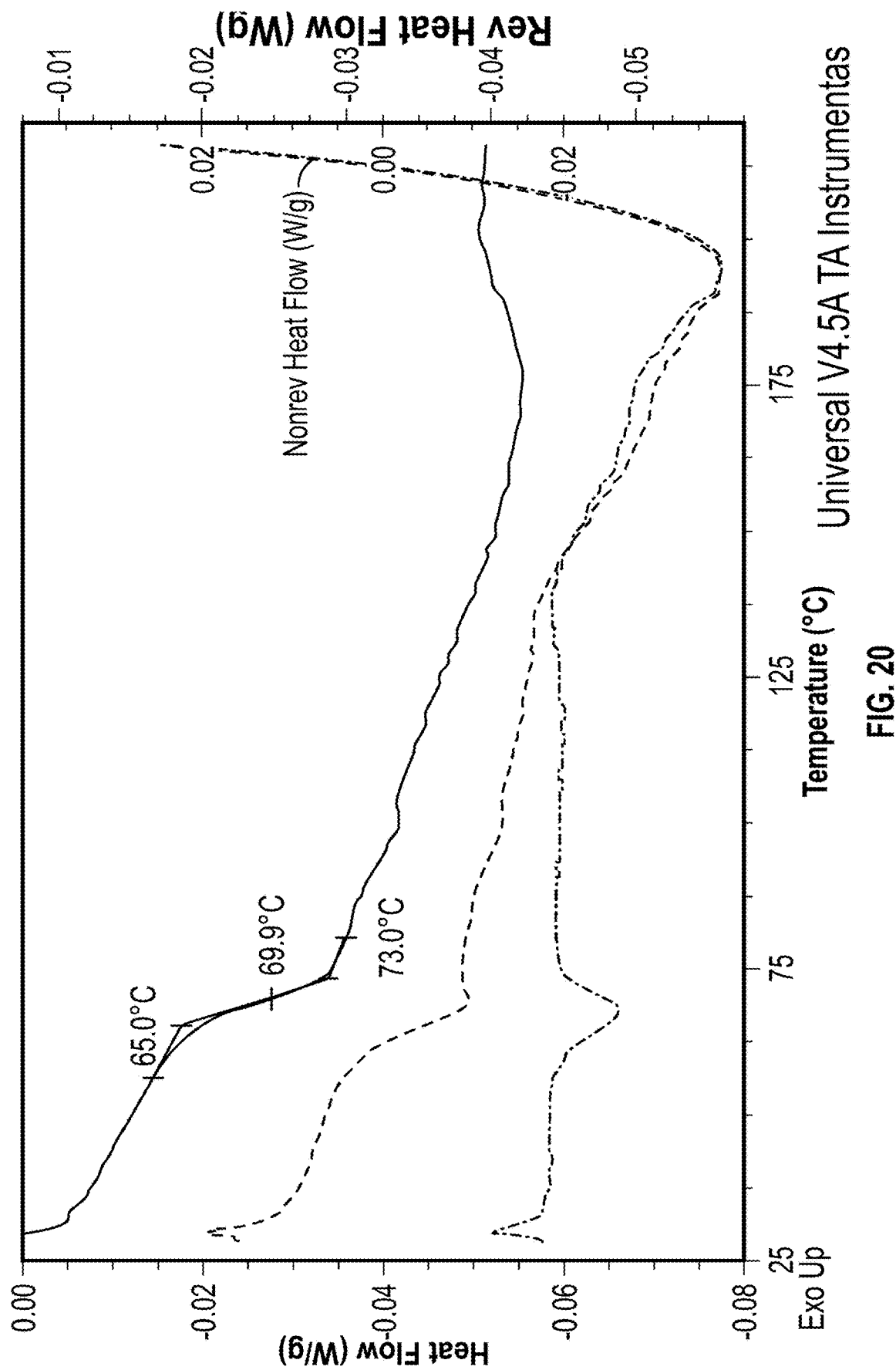
FIG. 20 illustrates a modulated DSC profile of amorphous free base 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, according to Comparative Example 3.

The DSC profile of amorphous free base 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile is shown in FIG. 20. As shown in FIG. 20, the DSC thermogram shows a glass transition temperature of ~70° C., which is a relatively low glass transition temperature and therefore known to be associated with processability difficulties and increased physical and chemical instability due to greater molecular mobility within the solid.

In one embodiment, the crystalline form is designated crystalline Form A. In one embodiment, crystalline Form A has an X-ray powder diffraction pattern ("XRPD") comprising at least one characteristic peak at °2θ values selected from 8.6±0.2, 14.6±0.2, 16.9±0.2 and 18.3±0.2. In some embodiments only a single characteristic peak is present. In some embodiments two characteristic peaks are present. In some embodiments three characteristic peaks are present. In some embodiments four characteristic peaks are present.

In one embodiment, crystalline Form A has an X-ray powder diffraction pattern comprising peaks at °2θ values of 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

In another embodiment crystalline Form A has an X-ray powder diffraction pattern comprising peaks at °2θ values of 5.8±0.2, 7.1±0.2, 8.6±0.2, 11.7±0.2, 12.3±0.2, 13.0±0.2, 14.2±0.2, 14.6±0.2, 16.0±0.2, 16.9±0.2, 17.2±0.2, 17.6±0.2, 17.9±0.2, 18.1±0.2, 18.3±0.2, 19.4±0.2, 19.7±0.2, 20.4±0.2, 20.7±0.2, 21.2±0.2, 21.4±0.2, 21.8±0.2, 22.7±0.2, 23.0±0.2, 23.5±0.2, 23.9±0.2, 24.7±0.2, 25.5±0.2, 26.2±0.2, 26.4±0.2, 27.2±0.2, 28.0±0.2, 28.2±0.2 and 29.6±0.2.

In another embodiment, crystalline Form A has an X-ray powder diffraction pattern comprising two or more peaks at °2θ at 8.6±0.2, 14.6±0.2, 16.9±0.2 and 18.3±0.2.

In other embodiments, crystalline Form A has an XRPD pattern substantially as shown in FIG. 1.

Figure 2:
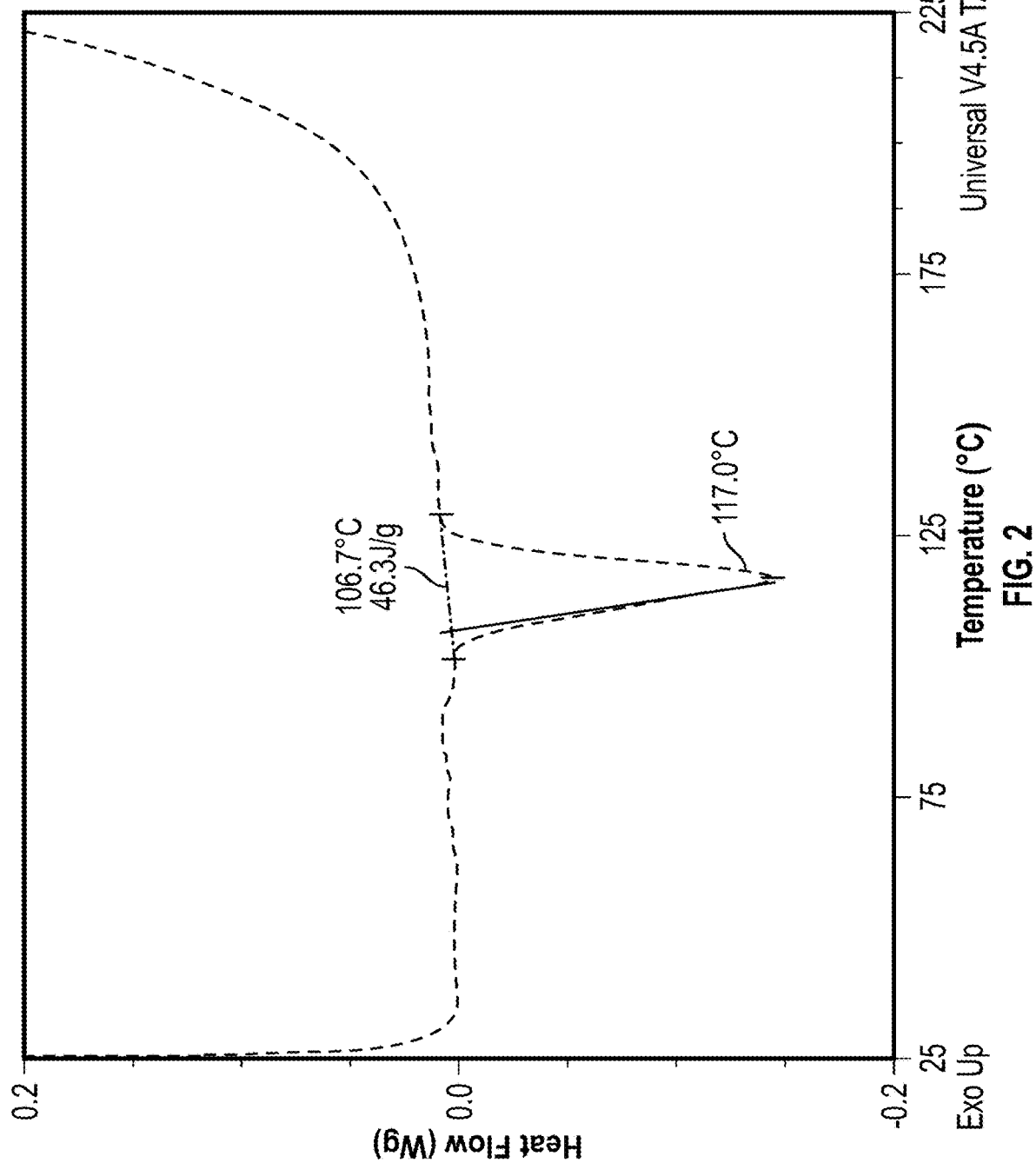
FIG. 2 illustrates a differential scanning calorimetry (DSC) profile of crystalline Form A prepared according to Example 1A.
Figure 11:
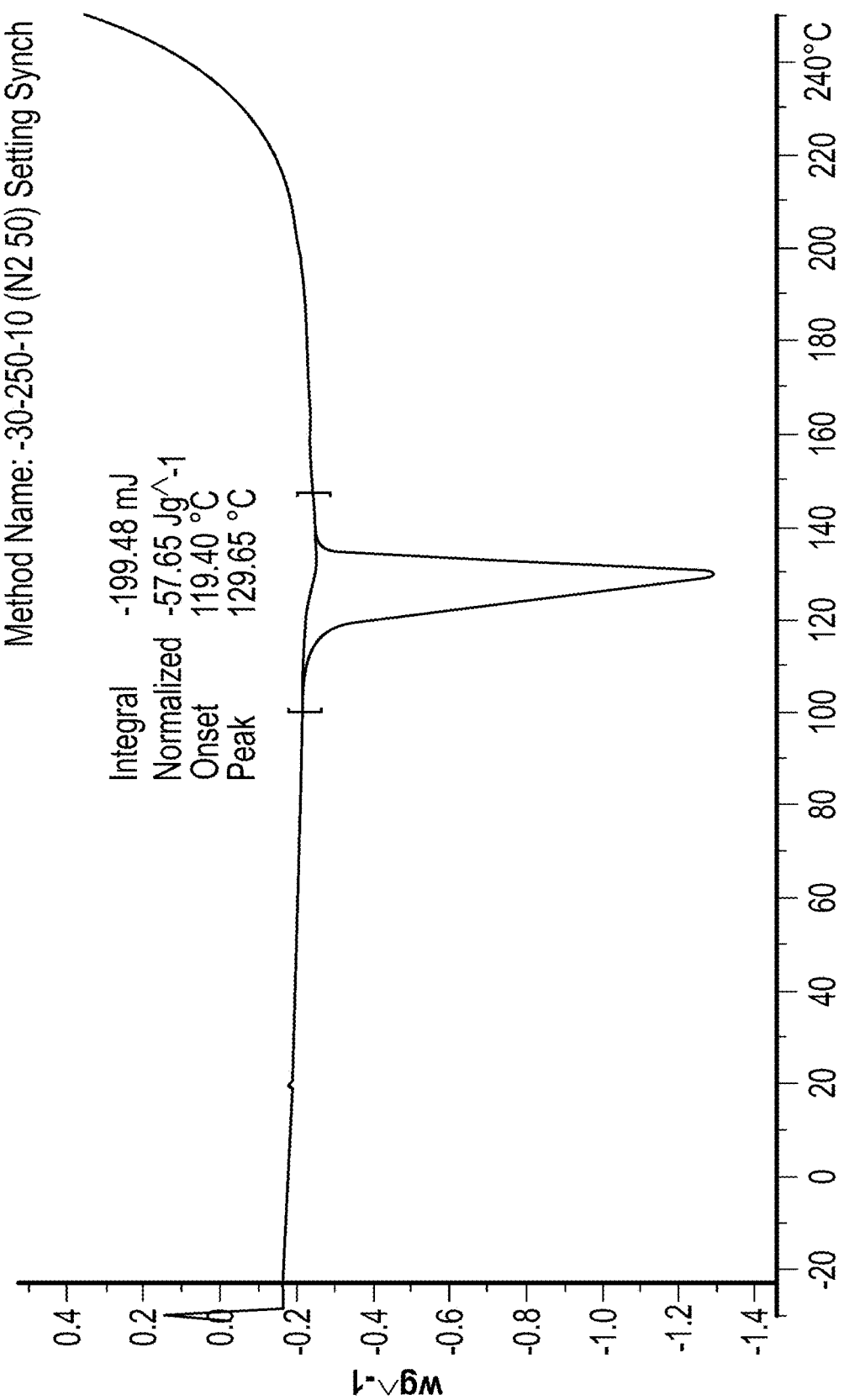
FIG. 11 illustrates a differential scanning calorimetry (DSC) profile of crystalline Form A prepared according to Example 1B.

In one embodiment, crystalline Form A is characterized by having an endothermic peak onset at about 107° C. with a heat of fusion of 46 J/g as measured by differential scanning calorimetry ("DSC"). In another embodiment, crystalline Form A has a DSC thermogram substantially as shown in FIG. 2. In one embodiment, crystalline Form A is characterized by having an endothermic peak onset at about 119° C. with a heat of fusion of 58 J/g as measured by differential scanning calorimetry ("DSC"). In another embodiment, crystalline Form A has a DSC thermogram substantially as shown in FIG. 11.

In another embodiment, Form A has both: 1) one or more DSC characteristics described above; and 2) an X-ray powder diffraction pattern comprising at least one peak at °2θ selected from 8.6±0.2, 14.6±0.2, 16.9±0.2 and 18.3±0.2.

In another embodiment, Form A has both: 1) one or more DSC characteristics described above; and 2) an X-ray powder diffraction pattern comprising at least one peak at °2θ selected from 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

Figure 3:
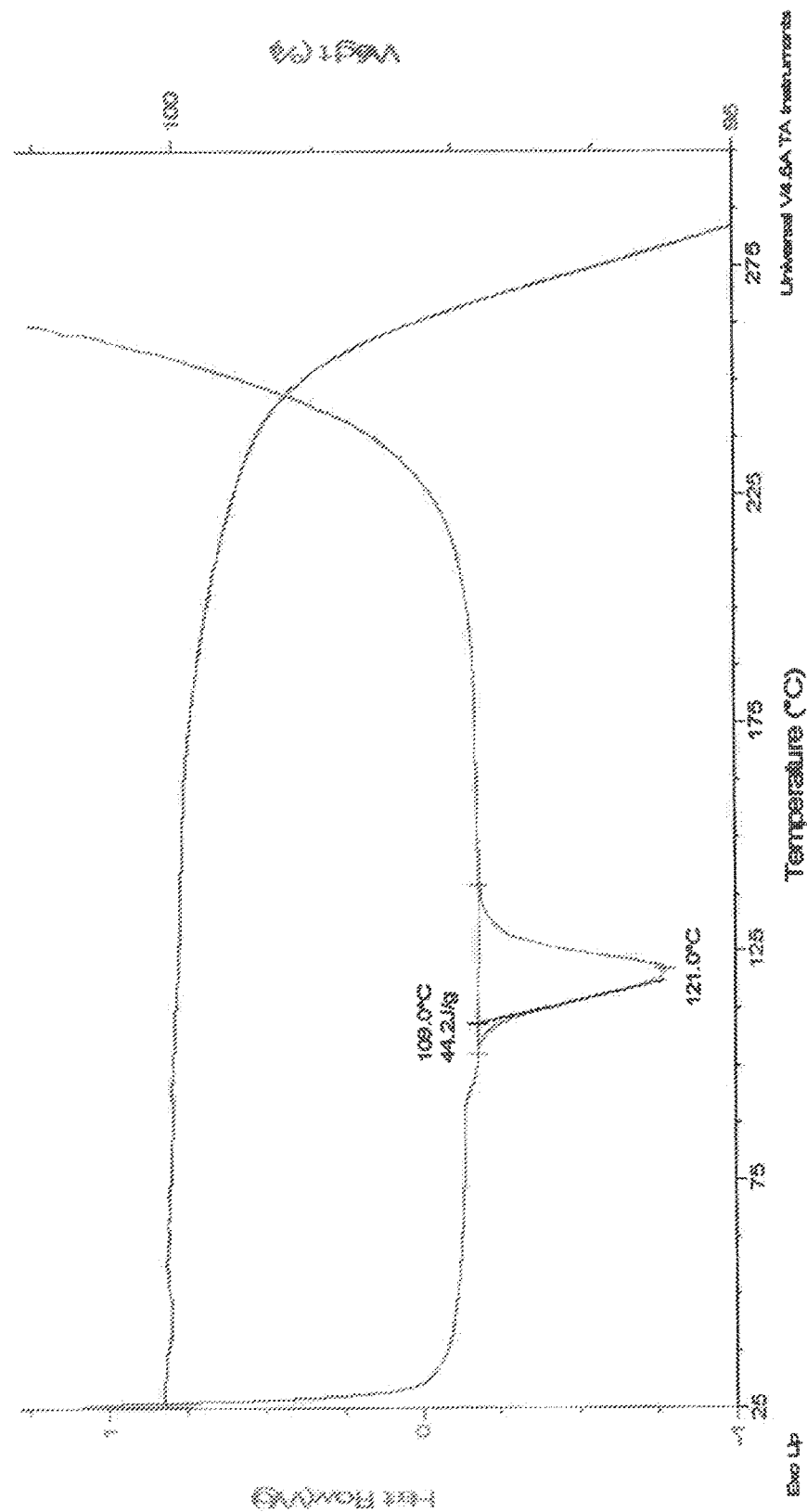
FIG. 3 illustrates a combined thermogravimetric analysis (TGA) and differential scanning calorimetry (DSC) profile of crystalline Form A prepared according to Example 1A.

In one embodiment, crystalline Form A is characterized by having negligible weight loss until degradation starting at about 200° C. as measured by thermogravimetric analysis ("TGA"). In another embodiment, crystalline Form A has a TGA profile substantially as shown in FIG. 3.

In another embodiment, Form A has both: 1) one or more TGA characteristics described above; and 2) an X-ray powder diffraction pattern comprising at least one peak at °2θ selected from 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

In another embodiment, Form A has both: 1) one or more TGA characteristics described above; and 2) an X-ray powder diffraction pattern comprising at least one peak at °2θ selected from 8.6±0.2, 14.6±0.2, 16.9±0.2 and 18.3±0.2.

Figure 4:
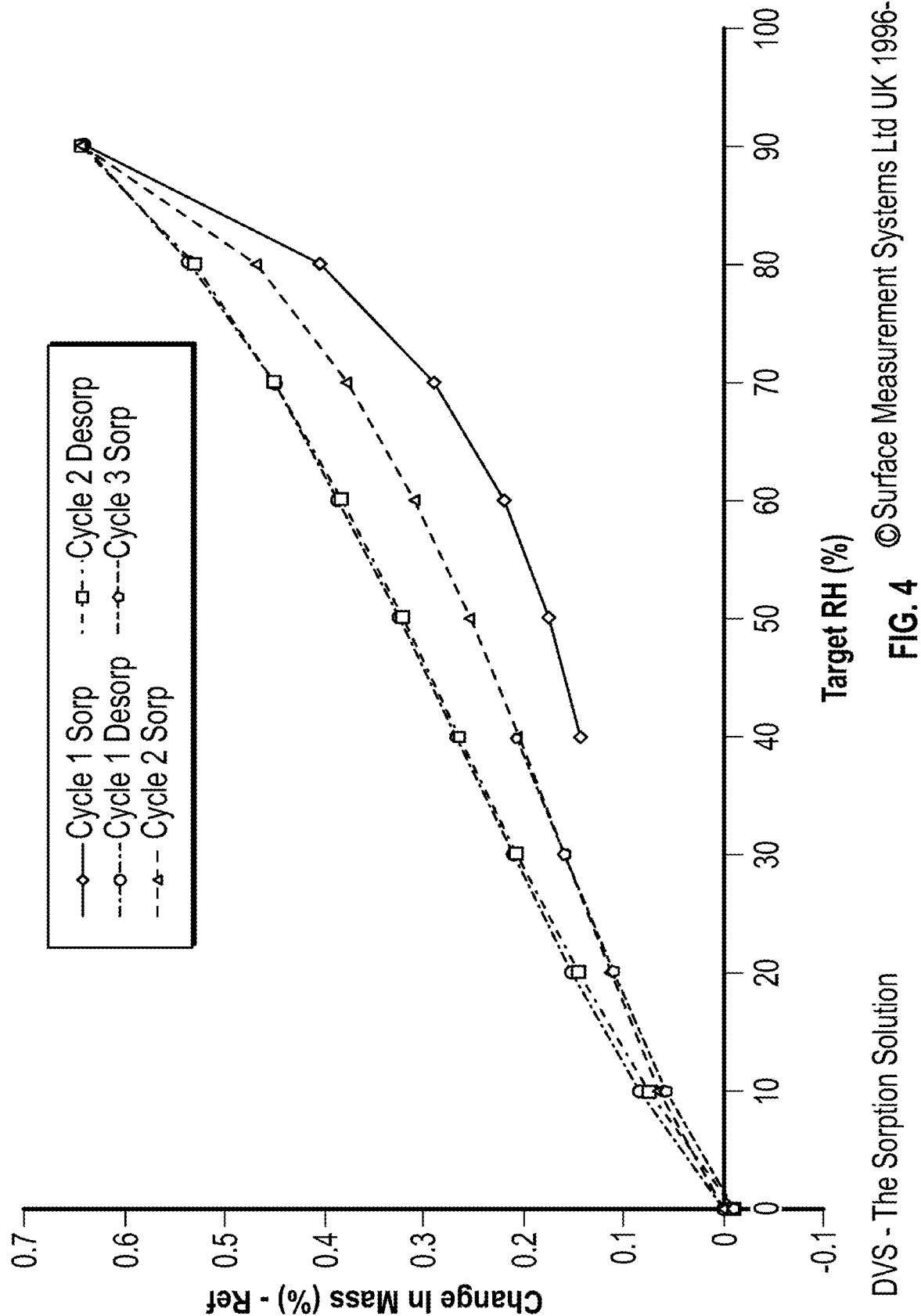
FIG. 4 illustrates a dynamic vapor sorption (DVS) isotherm profile of crystalline Form A prepared according to Example 1.

In one embodiment, crystalline Form A is characterized by having an observed weight gain from 0.4% from 5% to 90% RH and as RH declined during desorption, the observed weight gain was lost as measured by dynamic vapor sorption ("DVS"). In another embodiment, crystalline Form A has a DVS isotherm substantially as shown in FIG. 4.

In another embodiment, Form A has both: 1) one or more DVS characteristics described above; and 2) an X-ray powder diffraction pattern comprising at least one peak at °2θ selected from 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

In another embodiment, Form A has both: 1) one or more DVS characteristics described above; and 2) an X-ray powder diffraction pattern comprising at least one peak at °2θ selected from 8.6±0.2, 14.6±0.2, 16.9±0.2 and 18.3±0.2.

In one embodiment, crystalline Form A is substantially free of residual organic solvents.

In one embodiment, the crystalline form is designated crystalline Form B.

In one embodiment, crystalline Form B has an X-ray powder diffraction pattern comprising at least one characteristic peak at °2θ values selected from 16.7±0.2, 17.5±0.2 and 18.8±0.2. In some embodiments only a single characteristic peak is present. In some embodiments two characteristic peaks are present. In some embodiments three characteristic peaks are present.

In one embodiment, crystalline Form B has an X-ray powder diffraction pattern comprising peaks at °2θ values of 5.8±0.2, 13.3±0.2, 13.9±0.2, 14.2±0.2, 15.6±0.2, 15.9±0.2, 16.7±0.2, 17.4±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In one embodiment, crystalline Form B has an X-ray powder diffraction pattern comprising peaks at °2θ values of 5.8±0.2, 9.1±0.2, 11.2±0.2, 11.6±0.2, 12.3±0.2, 13.0±0.2, 13.3±0.2, 13.6±0.2, 13.9±0.2, 14.2±0.2, 14.5±0.2, 15.3±0.2, 15.6±0.2, 15.9±0.2, 16.7±0.2, 17.4±0.2, 17.9±0.2, 18.1±0.2, 18.4±0.2, 18.8±0.2, 19.5±0.2, 19.9±0.2, 20.4±0.2, 21.4±0.2, 21.8±0.2, 22.6±0.2, 23.1±0.2, 23.4±0.2, 23.7±0.2, 24.0±0.2, 24.3±0.2, 24.7±0.2, 25.1±0.2, 25.6±0.2, 25.8±0.2, 26.3±0.2, 26.7±0.2, 27.3±0.2, 27.6±0.2, 28.6±0.2, 29.4±0.2, 29.7±0.2 and 30.0±0.2.

In another embodiment, crystalline Form B has an X-ray powder diffraction pattern comprising two or more peaks at °2θ at 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

Figure 5A:
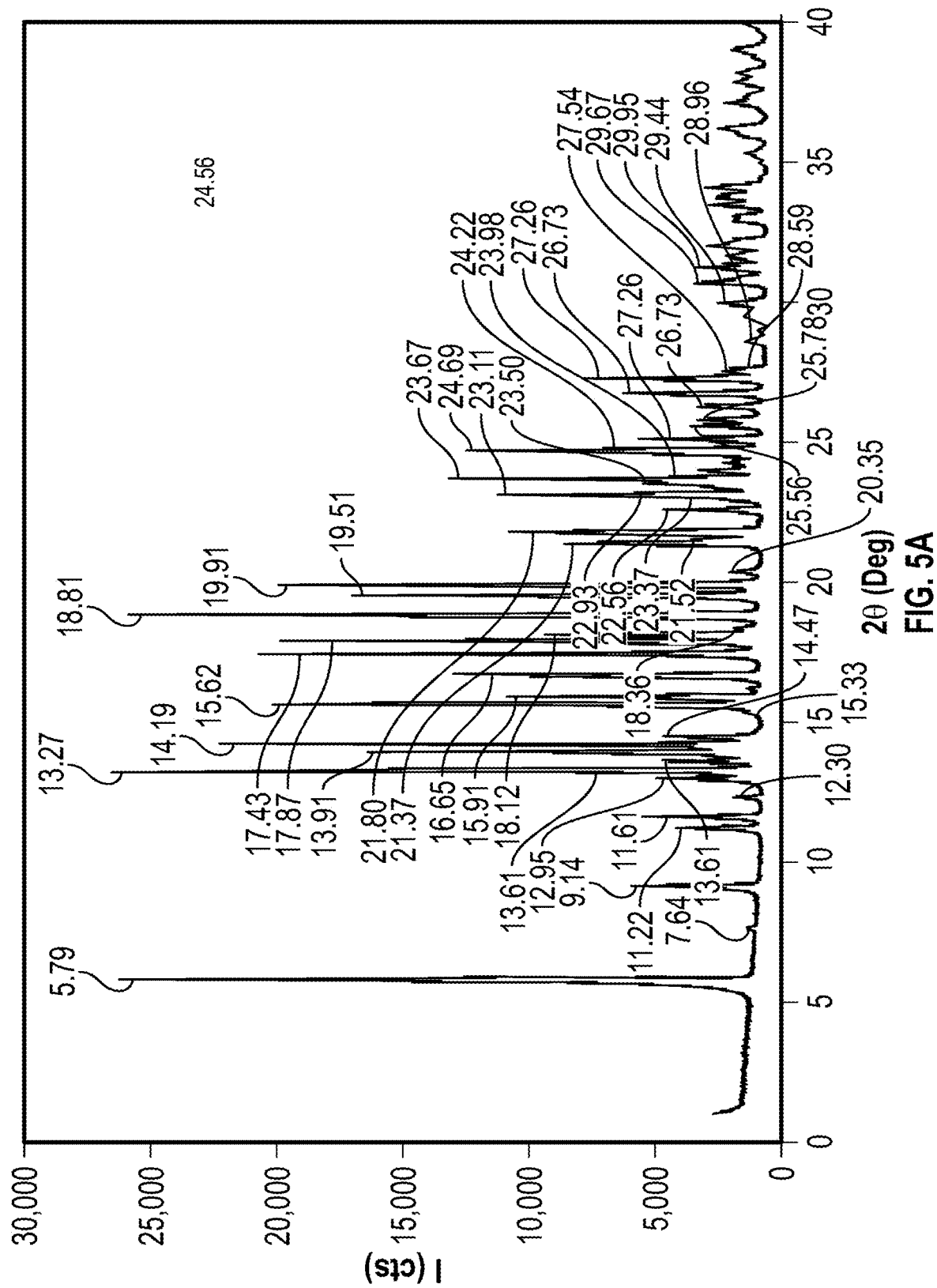
FIG. 5A illustrates an XRPD pattern of crystalline Form B made according to Example 2D.
Figure 5B:
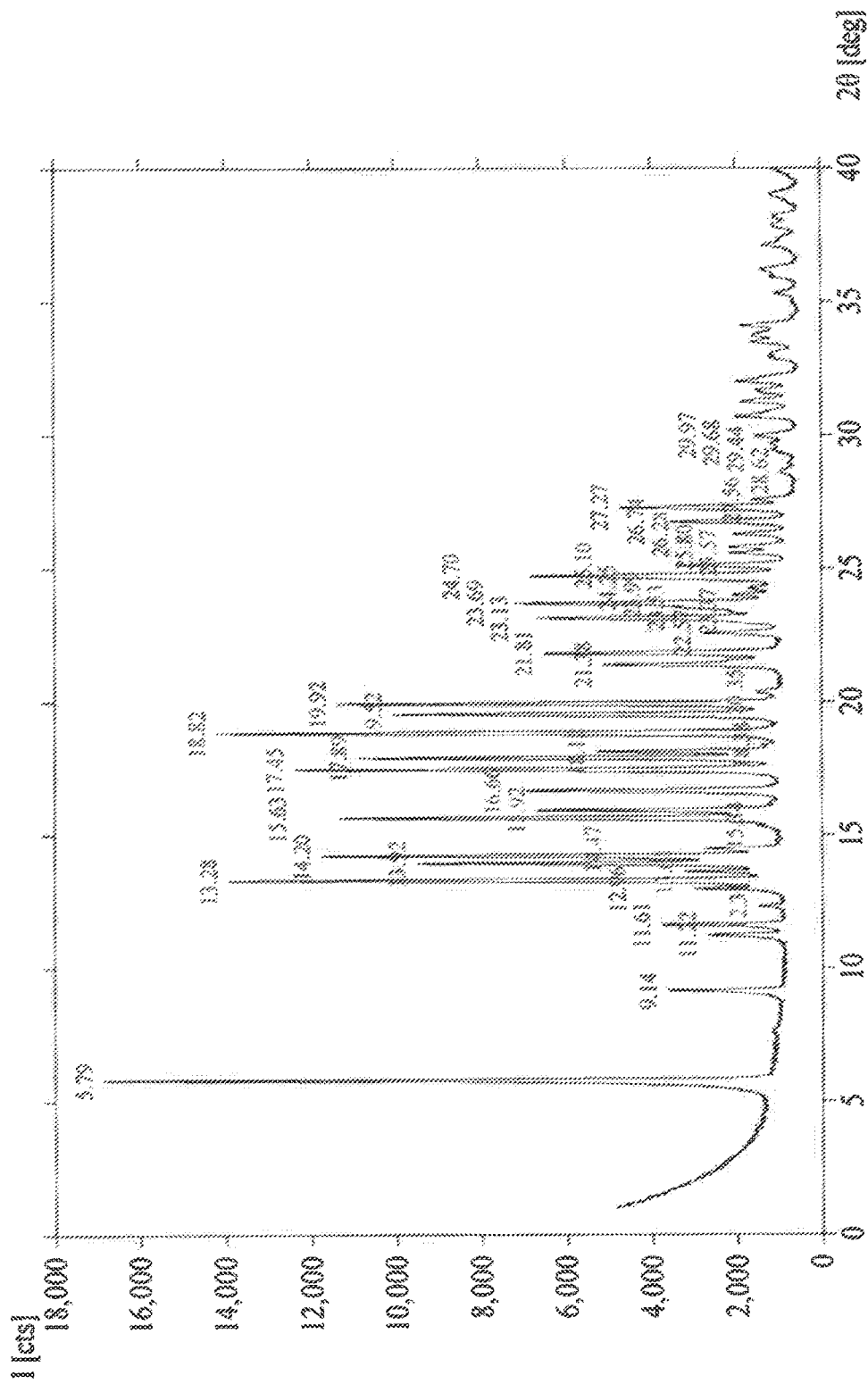
FIG. 5B illustrates an additional XRPD pattern of crystalline Form B.

In another embodiment, crystalline Form B has an XRPD pattern substantially as shown in FIG. 5A or in FIG. 5B.

Figure 6:
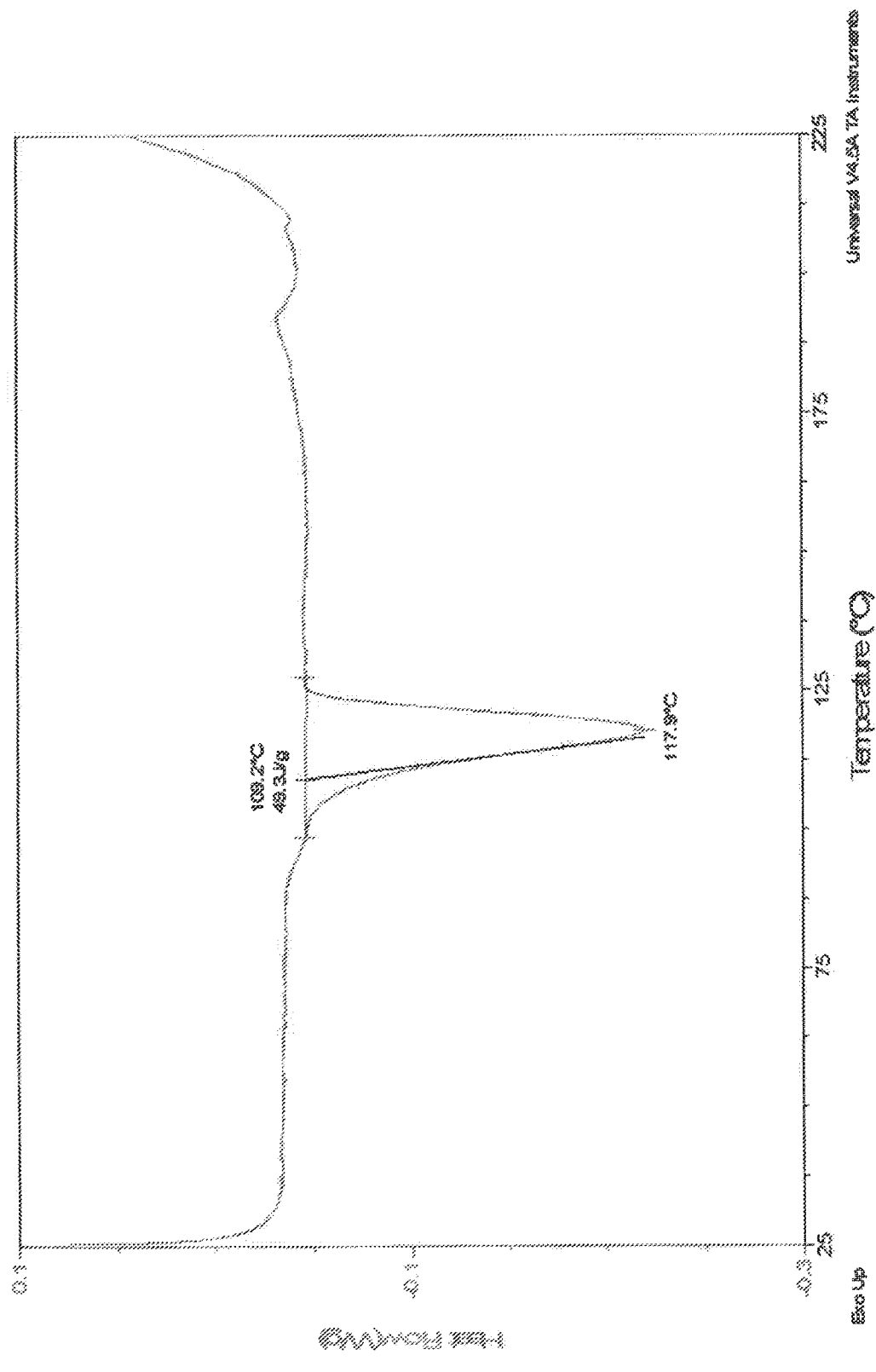
FIG. 6 illustrates a DSC profile of crystalline Form B prepared according to Example 2B.

In one embodiment, crystalline Form B is characterized by having negligible weight loss up to 111° C. and having an endothermic peak onset at about 118° C. with a heat of fusion of 49 J/g as measured by DSC. In one embodiment, crystalline Form B has a DSC thermogram substantially as shown in FIG. 6.

In another embodiment, Form B has both: 1) one or more DSC characteristics described above; and 2) an X-ray powder diffraction pattern comprising at least one peak at °2θ selected from 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

Figure 7:
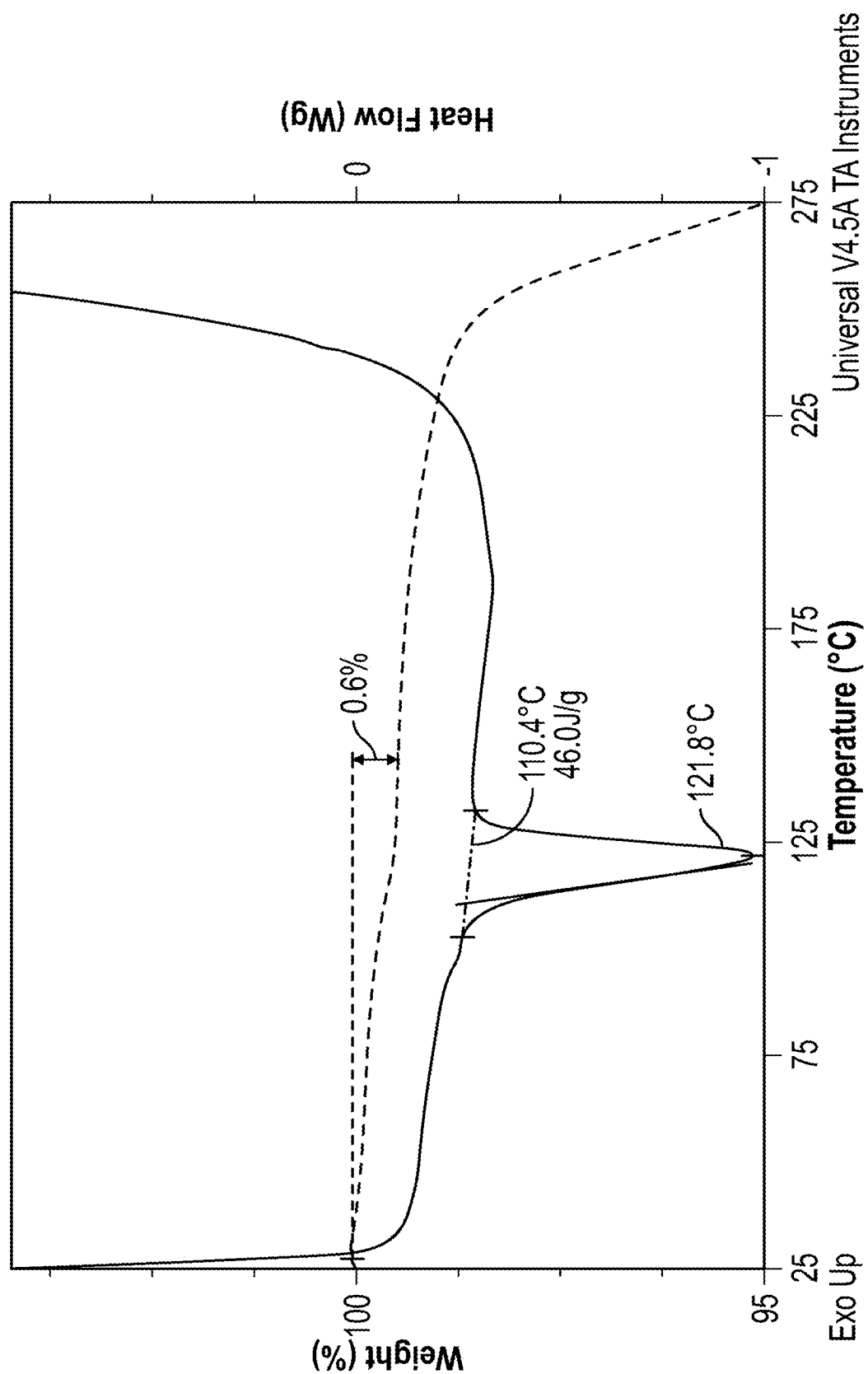
FIG. 7 illustrates a combined DSC and TGA profile of crystalline Form B prepared according to Example 2B.

In one embodiment, crystalline Form B as measured by TGA is characterized by having a negligible weight loss of mass for crystalline Form B up to about 111° C. until the onset of degradation at about 250° C. In another embodiment, crystalline Form B has a TGA profile substantially as shown in FIG. 7.

In another embodiment, Form B has both: 1) one or more TGA characteristics described above; and 2) an X-ray powder diffraction pattern comprising at least one peak at °2θ selected from 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In one embodiment, crystalline Form B as measured by DVS is characterized by having a weight gain of 0.2 wt % between 5% and 55% RH, increasing by 3.5% between 55% and 95% RH. The weight gain corresponds to 1.3 mol water. During desorption, the weight gain was lost with some hysteresis. In another embodiment, crystalline Form B has a DVS isotherm substantially as shown in FIG. 8.

Figure 8:
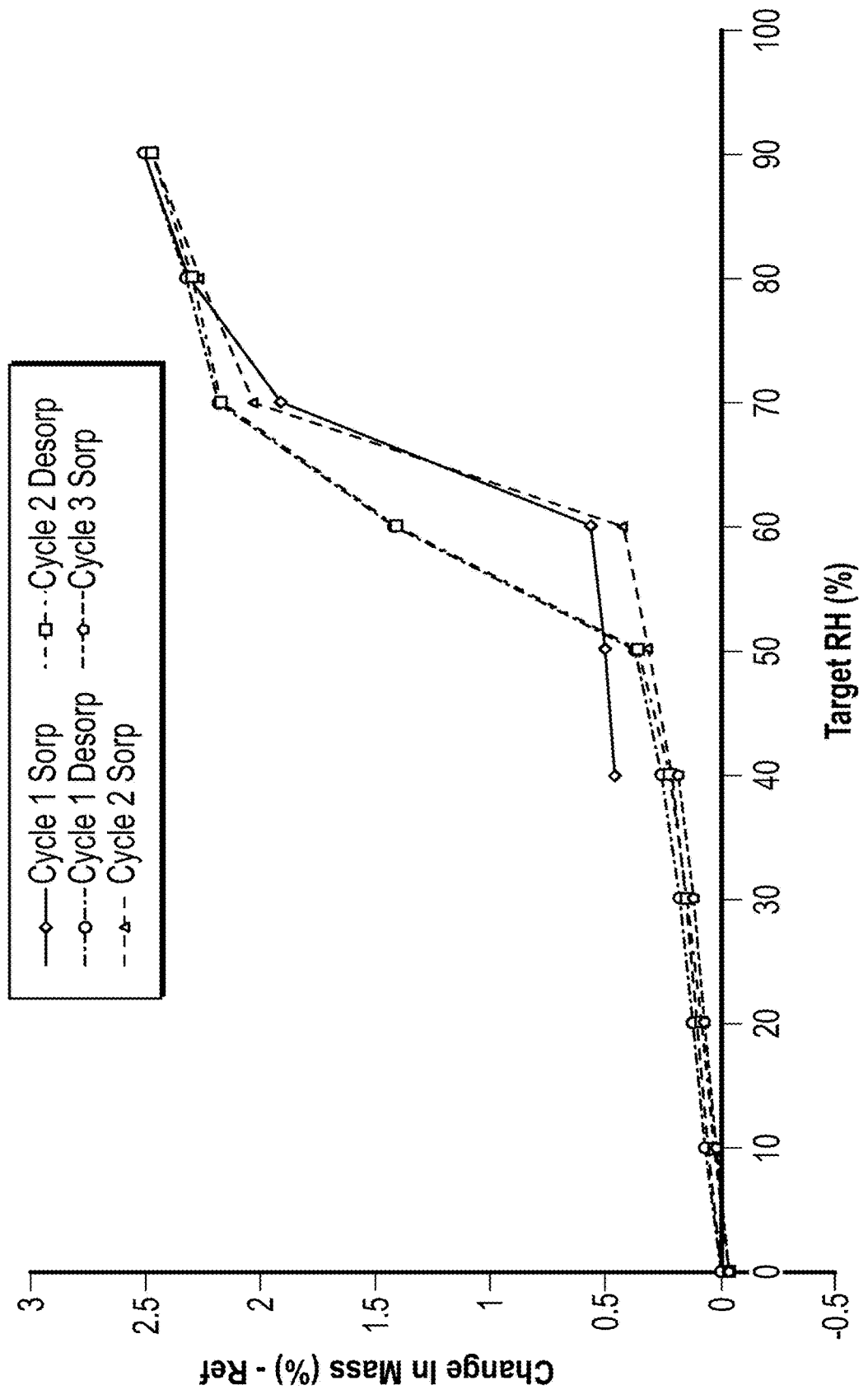
FIG. 8 illustrates a DVS isotherm profile of crystalline Form B prepared according to Example 2B.

In one embodiment, crystalline Form B as measured by DVS as shown in FIG. 8 is characterized by having a weight gain from about 0.6% at 60% RH to 2.9% at 70% RH, further increasing to 2.5% at 90% RH. Following a weight loss to 2.2% from 90% RH to 70% RH, a rapid weight loss is observed from 70 to 50% RH with a weight change from 2.2% to 0.4%. Constant gentle decrease in weight to 0% from 50 to 0% RH is observed. Cycles repeat showing little hysteresis.

In another embodiment, Form B has both: 1) one or more DVS characteristics described above; and 2) an X-ray powder diffraction pattern comprising at least one peak at °2θ selected from 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

In one embodiment, crystalline Form B is substantially free of residual organic solvents.

In one embodiment, the crystalline form is designated crystalline Form C.

In one embodiment, crystalline Form C has an X-ray powder diffraction pattern comprising at least one characteristic peak at °2θ value selected from 16.4±0.2 and 19.7±0.2. In some embodiments only a single characteristic peak is present. In some embodiments two characteristic peaks are present.

In one embodiment, crystalline Form C has an X-ray powder diffraction pattern comprising peaks at °2θ values of 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

In one embodiment, crystalline Form C has an X-ray powder diffraction pattern comprising peaks at °2θ values of 5.7±0.2, 9.0±0.2, 11.0±0.2, 11.3±0.2, 12.3±0.2, 13.3±0.2, 13.9±0.2, 14.2±0.2, 15.1±0.2, 15.5±0.2, 15.8±0.2, 16.4±0.2, 17.1±0.2, 17.3±0.2, 17.8±0.2, 18.0±0.2, 18.4±0.2, 18.6±0.2, 19.3±0.2, 19.7±0.2, 21.1±0.2, 21.5±0.2, 21.8±0.2, 23.1±0.2, 23.2±0.2, 23.6±0.2, 23.7±0.2, 24.4±0.2, 24.7±0.2, 25.2±0.2, 26.3±0.2, 26.7±0.2, 27.2±0.2, 28.1±0.2, 29.0±0.2, 29.4±0.2 and 29.8±0.2.

In one embodiment, crystalline Form C has an X-ray powder diffraction pattern comprising two or more peaks at °2θ values at 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

Figure 9:
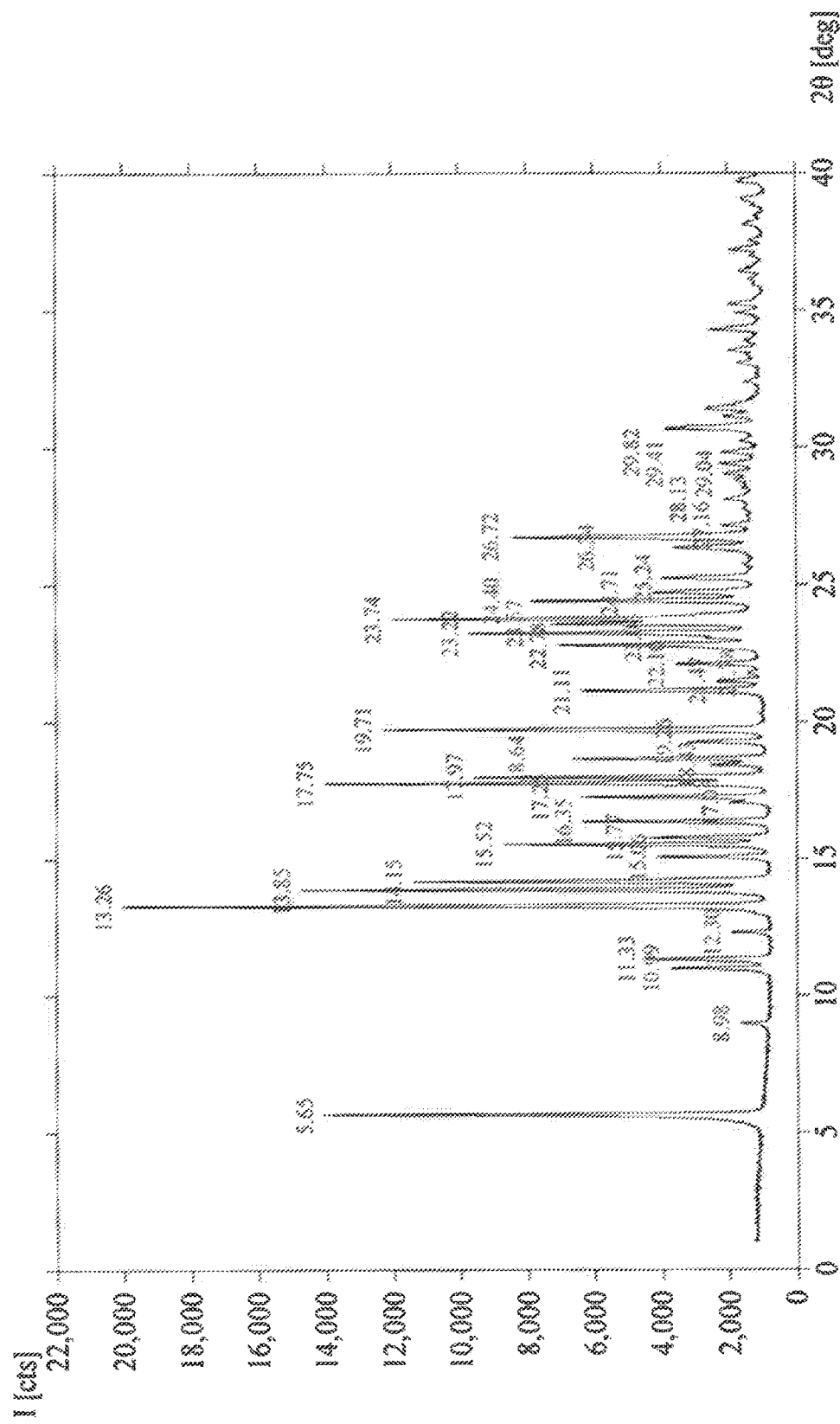
FIG. 9 illustrates an XRPD pattern of crystalline Form C prepared according to Example 3.

In another embodiment, crystalline Form C has an XRPD pattern substantially as shown in FIG. 9.

Figure 10:
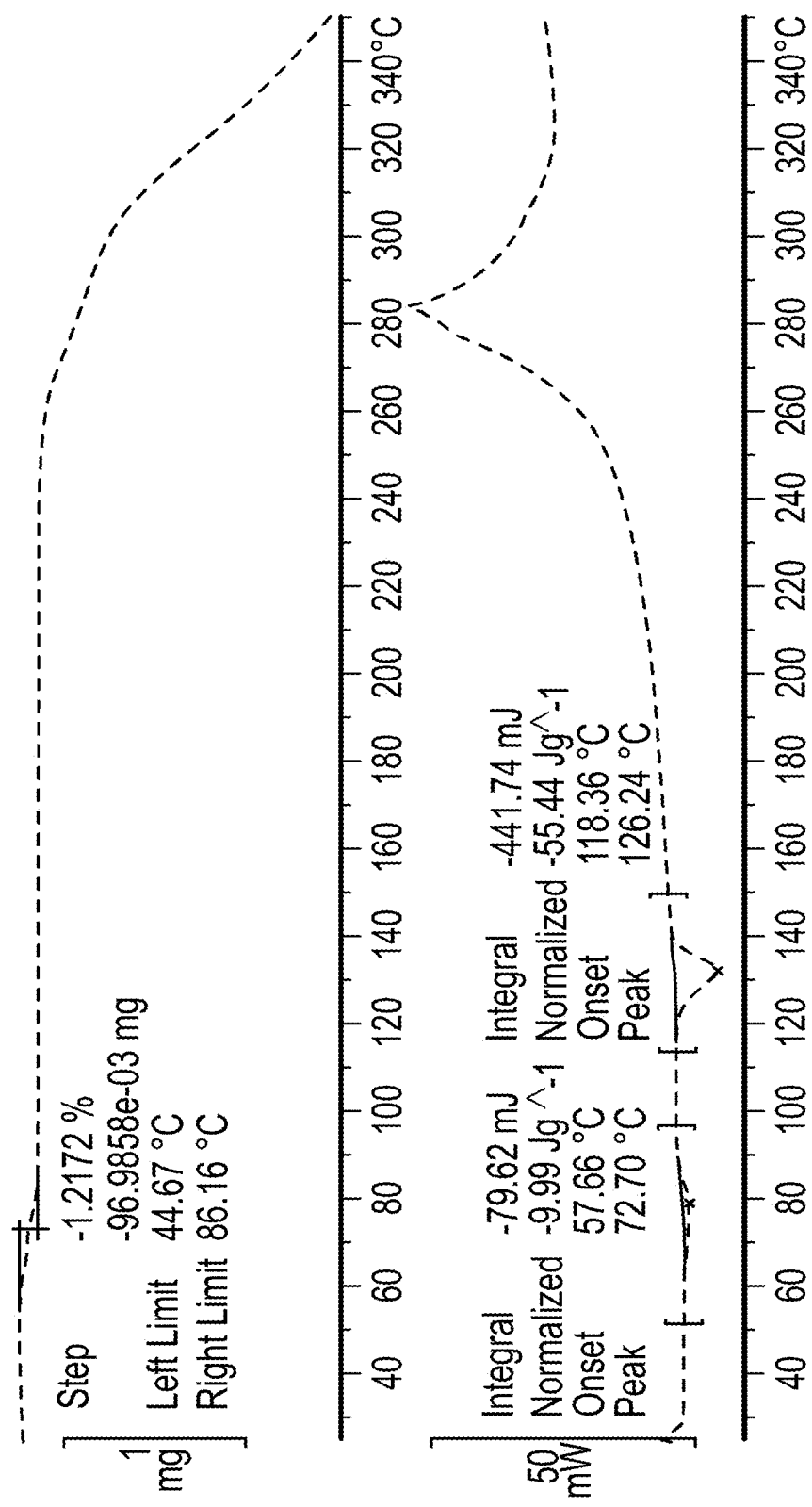
FIG. 10 illustrates a combined DSC and TGA profile of crystalline Form C prepared according to Example 3.

In one embodiment, crystalline Form C is characterized by having a small endothermic peak onset about 58° C. and a strong endothermic peak onset at about 118° C. by DSC. In one embodiment, crystalline Form C has a DSC thermogram substantially as shown in FIG. 10.

In another embodiment, Form C has both: 1) one or more DSC characteristics described above; and 2) an X-ray powder diffraction pattern comprising at least one peak at °2θ selected from 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

In one embodiment, crystalline Form C as measured by TGA is characterized by having a gradual loss of mass for crystalline Form C of 1.2% from about 45° C. to about 86° C. until the onset of degradation at about 260° C. In another embodiment, crystalline Form C has a TGA profile substantially as shown in FIG. 10.

In another embodiment, Form C has both: 1) one or more TGA characteristics described above; and 2) an X-ray powder diffraction pattern comprising at least one peak at °2θ selected from 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

In one embodiment, crystalline Form C is substantially free of residual organic solvents.

In one embodiment, crystalline Form C is a hydrate.

In one embodiment, the crystalline form is designated crystalline Form D.

In one embodiment, crystalline Form D has an X-ray powder diffraction pattern comprising at least one characteristic peak.

In one embodiment, crystalline Form D has an X-ray powder diffraction pattern at a °2θ value of 4.4±0.2.

In another embodiment, crystalline Form D has an X-ray powder diffraction pattern comprising peaks at °2θ values of 4.4±0.2, 13.6±0.2, 13.8±0.2, 15.2±0.2, 16.3±0.2, 17.7±0.2, 18.0±0.2, 20.1±0.2, 22.6±0.2, 23.0±0.2, and 27.6±0.2.

In one embodiment, crystalline Form D has an X-ray powder diffraction pattern comprising peaks at °2θ values of 4.4±0.2, 8.9±0.2, 10.0±0.2, 11.2±0.2, 12.3±0.2, 12.7±0.2, 13.4±0.2, 13.6±0.2, 13.8±0.2, 14.3±0.2, 15.2±0.2, 16.1±0.2, 16.3±0.2, 16.9±0.2, 17.7±0.2, 18.0±0.2, 18.6±0.2, 19.2±0.2, 20.1±0.2, 21.2±0.2, 21.8±0.2, 22.6±0.2, 23.0±0.2, 23.5±0.2, 24.2±0.2, 24.7±0.2, 25.2±0.2, 26.1±0.2, 26.3±0.2, 27.2±0.2, 27.6±0.2, 27.9±0.2, 28.3±0.2, 29.0±0.2 and 29.2±0.2.

In one embodiment, crystalline Form D has an X-ray powder diffraction pattern comprising two or more peaks at °2θ value at 4.4±0.2, 13.6±0.2, 13.8±0.2, 15.2±0.2, 16.3±0.2, 17.7±0.2, 18.0±0.2, 20.9±0.2, 22.6±0.2, 23.0±0.2, and 27.6±0.2.

Figure 13:
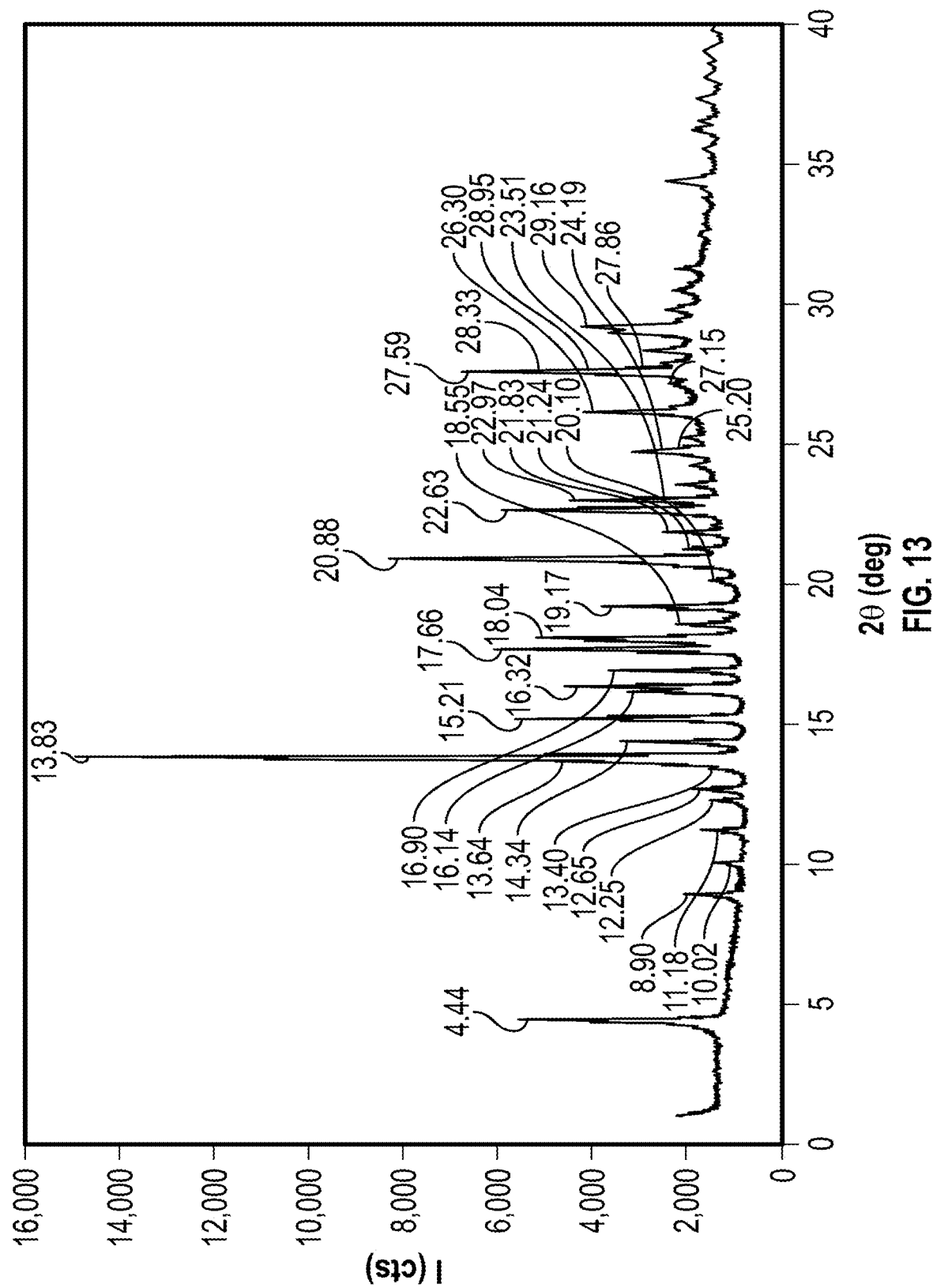
FIG. 13 illustrates an XRPD pattern of crystalline Form D prepared according to Example 4.

In another embodiment, crystalline Form D has XRPD pattern substantially as shown in FIG. 13.

Figure 14:
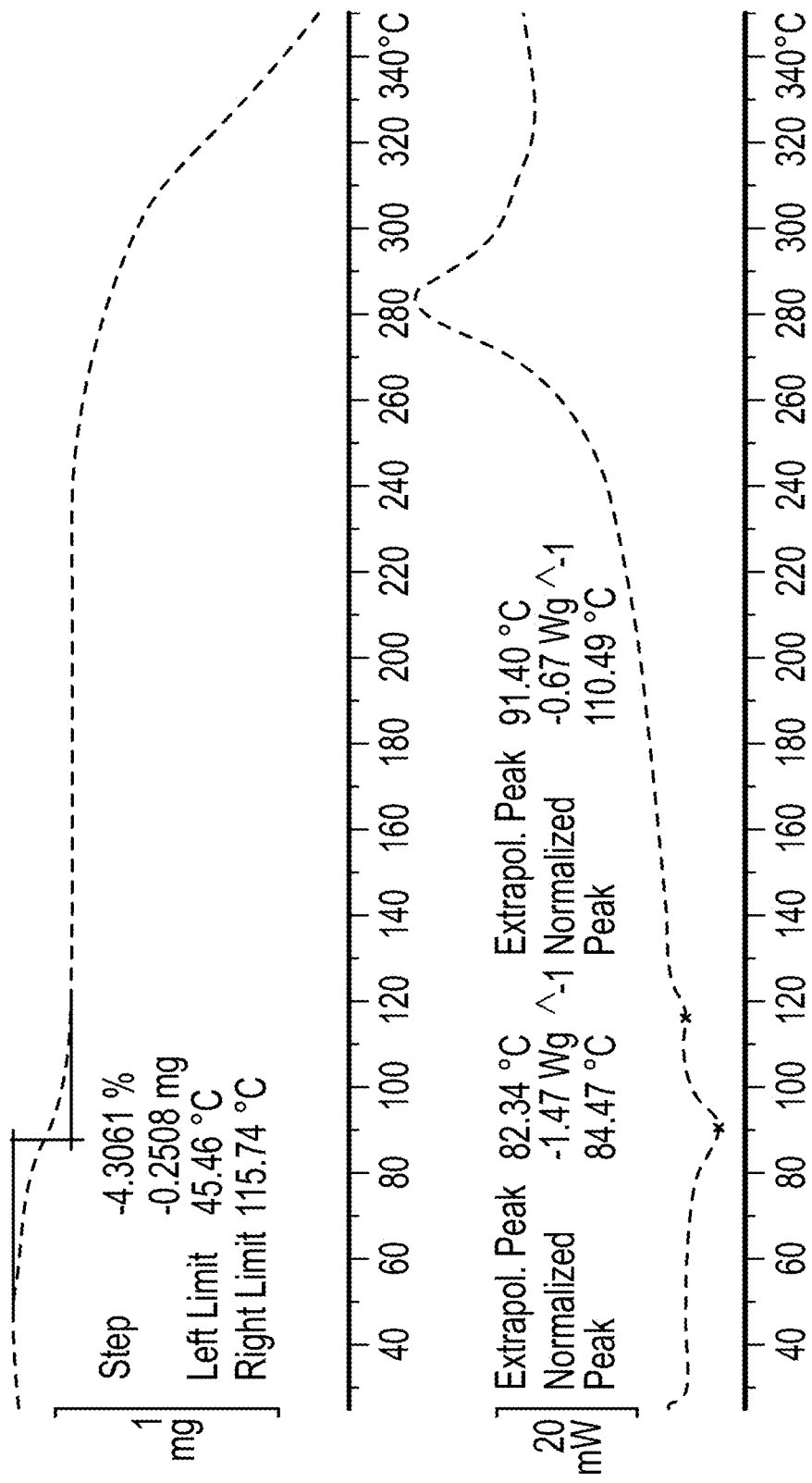
FIG. 14 illustrates a DSC profile and TGA profile of crystalline Form D prepared according to Example 4.

In one embodiment, crystalline Form D is characterized by having an endothermic peak maximum at about 84° C. and another endothermic peak with a peak maximum at about 110° C. by differential scanning calorimetry. In one embodiment, crystalline Form D has a DSC thermogram substantially as shown in FIG. 14.

In another embodiment, crystalline Form D has both: 1) one or more DSC characteristics described above; and 2) an X-ray powder diffraction pattern comprising at least one peak at °2θ selected from 4.4±0.2, 13.6±0.2, 13.8±0.2, 15.2±0.2, 16.3±0.2, 17.7±0.2, 18.0±0.2, 20.9±0.2, 22.6±0.2, 23.0±0.2, and 27.6±0.2.

In one embodiment, crystalline Form D as measured by TGA is characterized by having a gradual loss of mass for crystalline Form D of 4.3% from about 45° C. to about 116° C. until the onset of degradation at about 260° C. In another embodiment, crystalline Form D has a TGA profile substantially as shown in FIG. 14.

In another embodiment, crystalline Form D has both: 1) one or more TGA characteristics described above; and 2) an X-ray powder diffraction pattern comprising at least one peak at °2θ selected from 4.4±0.2, 13.6±0.2, 13.8±0.2, 15.2±0.2, 16.3±0.2, 17.7±0.2, 18.0±0.2, 20.9±0.2, 22.6±0.2, 23.0±0.2, and 27.6±0.2.

In one embodiment, crystalline Form D is substantially free of residual organic solvents.

In one embodiment, crystalline Form D is a hydrate.

In one embodiment, the crystalline form is designated crystalline Form E.

In one embodiment, crystalline Form E has an X-ray powder diffraction pattern comprising at least one characteristic peak.

In one embodiment, crystalline Form E has an X-ray powder diffraction pattern comprising at least one characteristic peak at °2θ values selected from 5.2±0.2 and 10.2±0.2. In some embodiments only a single characteristic peak is present. In some embodiments two characteristic peaks are present.

In one embodiment, crystalline Form E has an X-ray powder diffraction pattern comprising peaks at °2θ values of 5.2±0.2, 9.2±0.2, 10.2±0.2, 11.2±0.2, 11.8±0.2, 13.5±0.2, 14.3±0.2, 15.4±0.2, 16.4±0.2, 16.9±0.2, 17.7±0.2, 18.0±0.2, 19.4±0.2, 20.3±0.2, 20.5±0.2, 21.0±0.2, 21.3±0.2, 21.9±0.2, 22.4±0.2, 22.7±0.2, 23.1±0.2, 23.8±0.2, 24.2±0.2, 25.7±0.2, 26.8±0.2, 27.2±0.2, 27.4±0.2, 27.9±0.2, 28.6±0.2 and 29.0±0.2.

In another embodiment, crystalline Form E has an X-ray powder diffraction pattern comprising peaks at °2θ values of 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2

In one embodiment, crystalline Form E has an X-ray powder diffraction pattern comprising two or more peaks at °2θ value at 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

Figure 15:
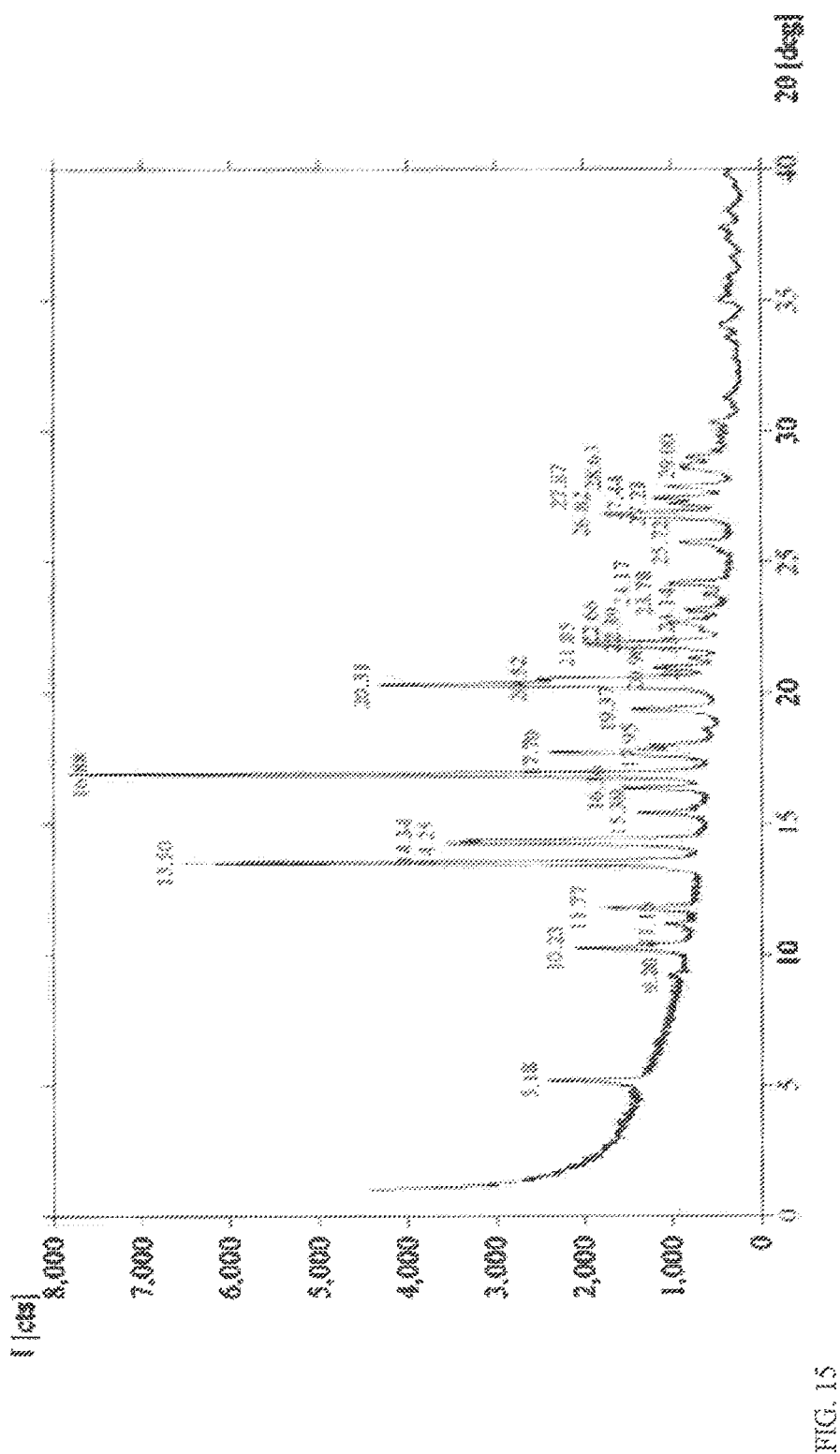
FIG. 15 illustrates an XRPD pattern of crystalline Form E prepared according to Example 5.

In another embodiment, crystalline Form E has XRPD pattern substantially as shown in FIG. 15.

Figure 16:
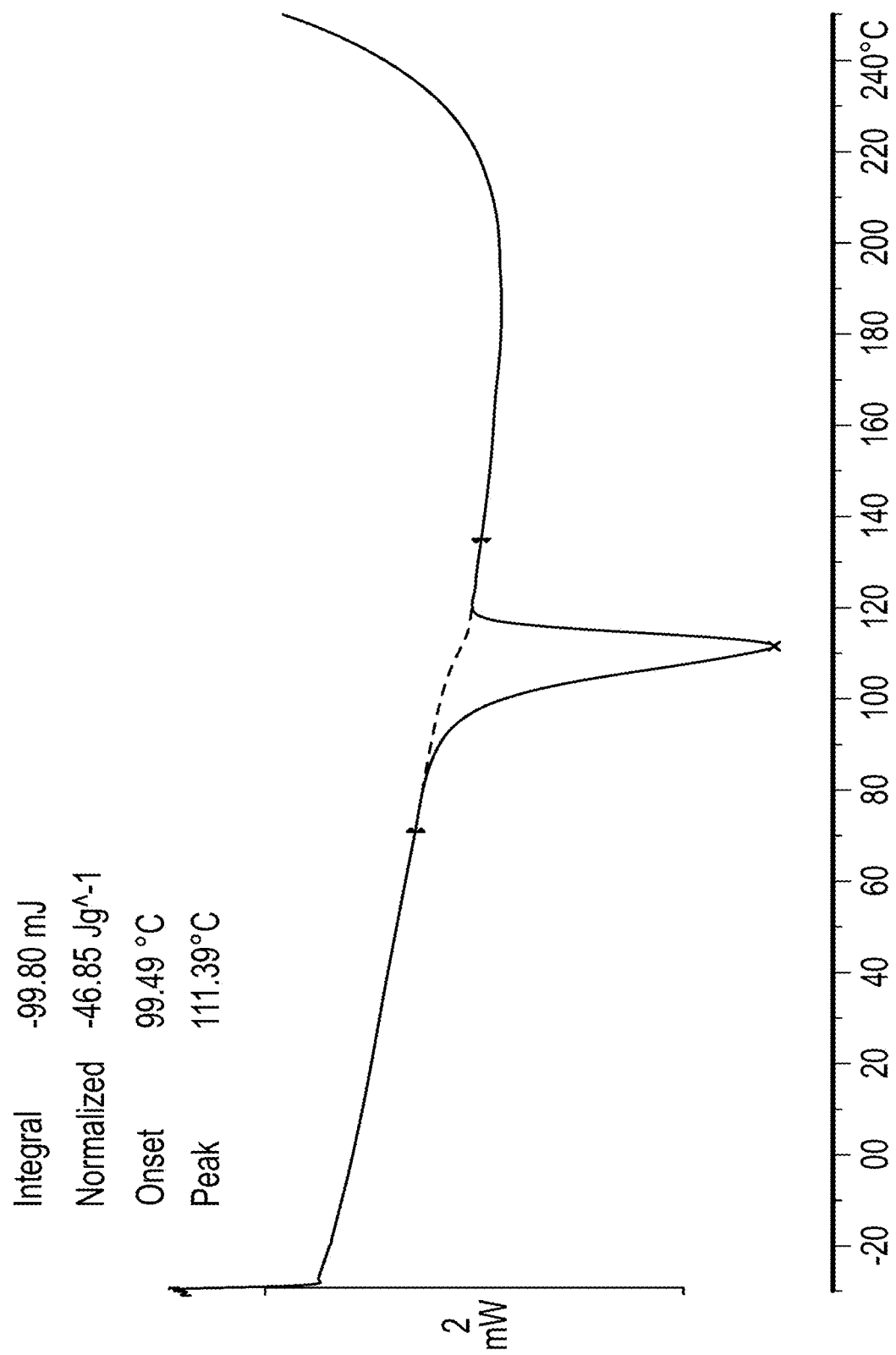
FIG. 16 illustrates a DSC profile of crystalline Form E prepared according to Example 5.

In one embodiment, crystalline Form E as measured by DSC is characterized by having an endothermic peak onset at about 99° C. and a heat of fusion of 47 J/g. In one embodiment, crystalline Form E has a DSC thermogram substantially as shown in FIG. 16.

In another embodiment, crystalline Form E has both: 1) one or more DSC characteristics described above; and 2) an X-ray powder diffraction pattern comprising at least one peak at °2θ selected from 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

Figure 17:
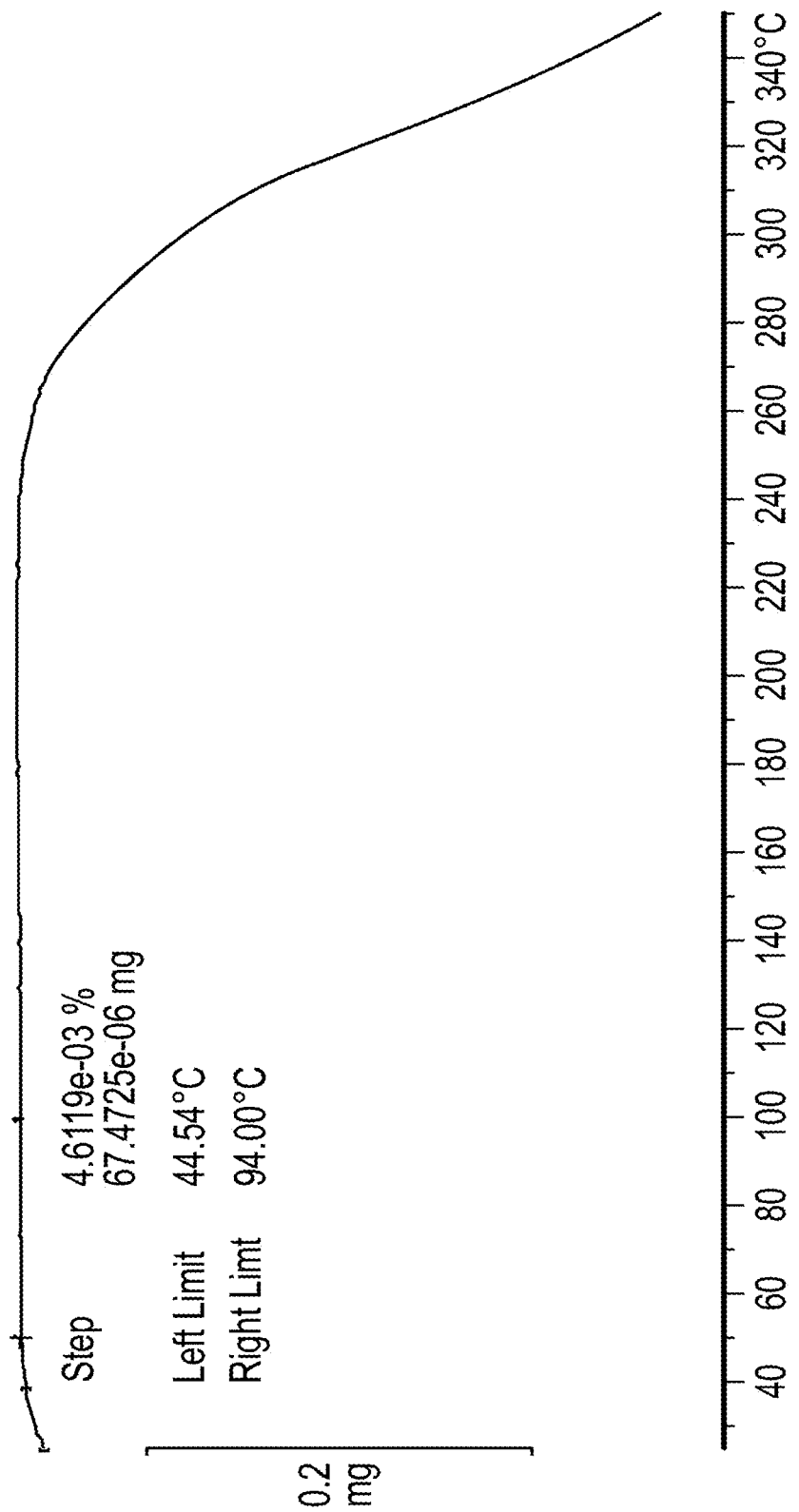
FIG. 17 illustrates a TGA profile of crystalline Form E prepared according to Example 5.

In one embodiment, crystalline Form E as measured by TGA is characterized by having negligible loss of mass for crystalline Form E of up to about 94° C. through the onset of degradation at about 240° C. In another embodiment, crystalline Form E has a TGA profile substantially as shown in FIG. 17.

In another embodiment, crystalline Form E has both: 1) one or more TGA characteristics described above; and 2) an X-ray powder diffraction pattern comprising at least one peak at °2θ selected from 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

Figure 18:
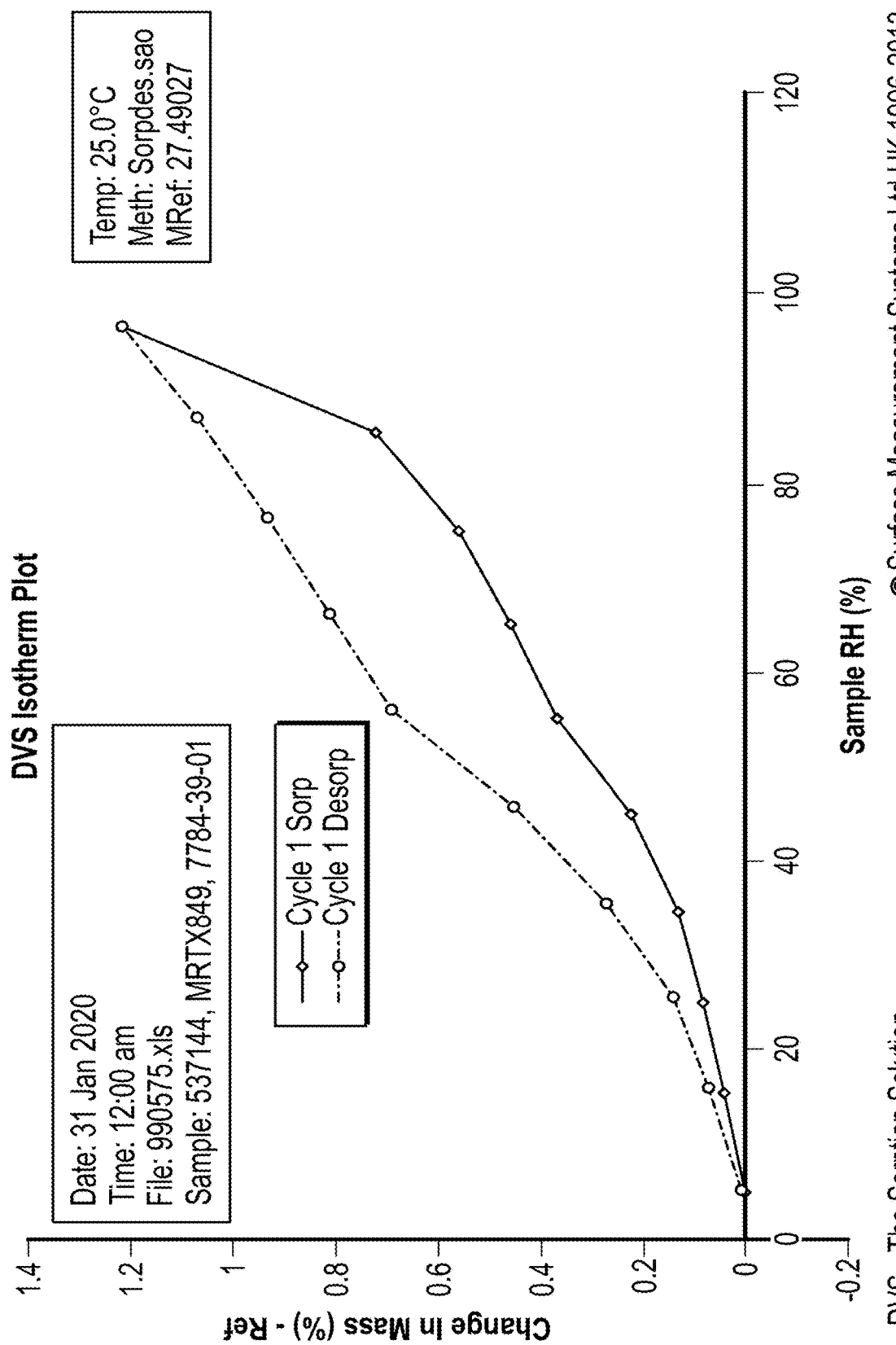
FIG. 18 illustrates a DVS isotherm profile of crystalline Form E.

In one embodiment, crystalline Form E as measured by DVS is characterized by having a gradual weight gain of 1.2% between 5% to 96% RH. During desorption, the weight gained was lost with some hysteresis. In another embodiment, crystalline Form E has a DVS isotherm substantially as shown in FIG. 18.

In another embodiment, crystalline Form E has both: 1) one or more TGA characteristics described above; and 2) an X-ray powder diffraction pattern comprising at least one peak at °2θ selected from 5.2±0.2, 10.2±0.2, 11.8±0.2, 13.5±0.2, 14.3±0.2, 16.9±0.2, 17.7±0.2, 20.3±0.2, 20.5±0.2 and 21.9±0.2.

In one embodiment, crystalline Form E is substantially free of residual organic solvents Processes for Preparing Crystalline Forms In one embodiment, crystalline Form A is obtained by the process comprising the steps: suspending 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile in heptane; temperature cycling the resulting suspension between about 25° C. to about 80° C.; and evaporating off the heptane to obtain crystalline Form A.

In another embodiment, crystalline Form A is obtained by dissolving amorphous 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile in a mixture of IPA:MTBE, then cooling the solution to 50° C., then seeding Form A 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile and cooling to 25° C. and filtering and drying to obtain crystalline Form A.

In another embodiment, crystalline Form A is obtained by dissolving 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile in IPA at about at 50° C., then allowing crystals of Form A to form over time upon cooling to sub-ambient temperature.

In one embodiment, the process further comprises collecting the crystalline Form A. In other embodiments, the process further comprises drying the crystalline Form A in a vacuum oven prior to or after collection.

In one embodiment, the water-immiscible organic solvent is heptane.

In one embodiment, crystalline Form B is obtained by the process comprising the steps: (a) suspending 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile in a mixture of water and a water-miscible organic solvent that has been heated to about 50° C.; and (c) slowly cooling the suspension to about 5° C. to obtain crystalline Form B. In one such embodiment the sample was cooled to about 5° C. at the rate of about 0.5° C./min.

In one embodiment, the process further comprises collecting the crystalline Form B. In other embodiments, the process further comprises drying the crystalline Form B in a vacuum oven prior to or after collection.

In one embodiment, the process further comprises seeding the suspension with a predetermined amount of crystalline Form B when the suspension reaches a temperature of 30° C. during step (c) to assist in crystallization. In one embodiment, the suspension was seeded with crystalline Form B at 30° C. and then cooled to 5° C.

In one embodiment, the water-miscible organic solvent is 10% water in isopropyl alcohol.

In one embodiment, the water-miscible organic solvent is isopropanol.

In another embodiment, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile is dissolved in 10% H2O in IPA at about 50° C., then cooled to about 5° C. at about 0.5° C./min. In this embodiment, when the solution reaches about 30° C. it is seeded with Form B and cooling continues, resulting in a partially crystalline solid at 5° C. In another embodiment, additional seeding steps are employed before drying under vacuum. In some embodiments the solids are analyzed by X-ray powder diffraction to confirm Form B.

In still another embodiment, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile is dissolved in isopropanol/water (75/25 v/v) at about 70° C., then cooled to about 40° C. over about 30 minutes. In this embodiment a Form B seed slurry is added to the solution, held for about an hour at about 40° C. and then cooled to about 5° C. over about 10 hours. In this embodiment solids are collected, for instance by vacuum filtration and dried. In some embodiments the solids are analyzed by X-ray powder diffraction to confirm Form B.

In yet another embodiment, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile is dissolved in isopropanol/heptane at about 60° C., then cooled to about 45° C. over about 15 minutes. In this embodiment, a seed slurry is added to the solution, held at successively lower temperatures until reaching about 20° C. In this embodiment, solids are collected, for instance by vacuum filtration, and dried. In some embodiments the solids are analyzed by X-ray powder diffraction to confirm Form B.

In still another embodiment, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile is dissolved in 30% water:IPA at about 50° C., then cooled to about 25° C. and seeded Form B, then cooled to about 5° C. and stirred. In this embodiment a slurry forms and is filtered and then dried to obtain solids. In some embodiments the solids are analyzed by X-ray powder diffraction to confirm Form B.

In another embodiment of the invention, crystalline Form C is prepared by placing 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile in isopropanol/water (75/25 v/v) and stirring, for instance for about 14 days at ambient temperature, then collecting solids by filtering the resulting slurry through a syringe filter. In some embodiments the solids are analyzed by X-ray powder diffraction to confirm Form C.

In another embodiment crystalline Form D is prepared by dissolving 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile in isopropanol at ambient temperature, evaporating the solution at ~40° C. to obtain powdered and glassy solids, adding water to the solids and stirring, and then collecting solids by filtration, preferably vacuum filtration. In some embodiments these solids are analyzed by X-ray powder diffraction to confirm Form D.

In another embodiment crystalline Form E is prepared by placing 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form D in the presence of phosphorus pentoxide. In some embodiments this is accomplished by placing the Form D crystals in an open container and placing that open container in a larger vessel containing the phosphorous pentoxide. In some embodiments the resulting Form E crystals are analyzed by X-ray powder diffraction.

In one embodiment, the crystalline forms of the present invention are at least 40%, 50%, 60%, 70%, 80%, 90% or 95% crystalline.

The crystalline forms of the anhydrous free base Forms A through E may be formulated into pharmaceutical compositions.

Pharmaceutical Compositions

In another aspect, the invention provides pharmaceutical compositions crystalline forms of the KRas G12C inhibitor according to the invention and a pharmaceutically acceptable carrier, excipient, or diluent that may be used in the methods disclosed herein. The crystalline forms of the KRas G12C inhibitor and salts thereof may be formulated by any method well known in the art and may be prepared for administration by any route, including, without limitation, parenteral, oral, sublingual, transdermal, topical, intranasal, intratracheal, or intrarectal. In certain embodiments, the crystalline forms of the KRas G12C inhibitor or tartrate salt are administered intravenously in a hospital setting. In one embodiment, administration may be by the oral route.

In one embodiment, the crystalline form is Form A. In another embodiment, the crystalline form is Form B. In one embodiment, the crystalline form is Form C. In another embodiment, the crystalline form is Form D. In one embodiment, the crystalline form is Form E. In one embodiment, the crystalline form is a mixture of any of Forms A-E.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, citric acid, oxalic acid, tartaric acid, succinic acid, malic acid, fumaric acid, maleic acid, ascorbic acid, benzoic acid, tannic acid, pamoic acid, alginic acid, glutamic acid, ascorbic acid, adipic acid, aspartic acid, cinnamic acid, lauric acid, malonic acid, nicotinic acid, galactaric acid, gentisic acid, hippuric acid, glucoheptonic acid, thiocyanic acid, alginic acid, camphoric acid, gluconic acid, glucuronic acid, glutaric acid, glycerophosphoric acid, lactic acid, nicotinic acid, orotic acid, oleic acid, capric acid, caproic acid, palmitic acid, sebacic acid, stearic acid, pyroglutamic acid, salicylic acid, polyglutamic acid, methanesulfonic acid, ethanesulfonic acid, benzenesulfonic acid, toluenesulfonic acid, ethanedisulfonic acid, naphthalenesulfonic acid, naphthalenedisulfonic acid, hydroxynaphthoic acid, polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, tosylate, mesylate, besylate, sulfonate, phosphate, carboxylate (such as benzoate, succinate, acetate, fumarate, glycolate, maleate, malate, citrate, tartrate, oxalate, ascorbate, cinnamate, mandelate, gentisate, hippurate), aminoacid (such as aspartate, glutamate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to about 300 mg/kg, from about 0.1 to about 100 mg/kg per day, from about 0.5 to about 50 mg/kg per day, or from about 1 to about 25 mg/kg per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

In one embodiment, the pharmaceutical compositions of the present invention contain at least 95% of a crystalline form. In other embodiments, the pharmaceutical compositions of the present invention contain at least 90% of a crystalline form. In another embodiment, the pharmaceutical compositions of the present invention contain at least 80% of a crystalline form. In other embodiments, the pharmaceutical compositions of the present invention contain at least 70% of a crystalline form. In one embodiment, the pharmaceutical compositions of the present invention contain at least 60% of a crystalline form. In another embodiment, the pharmaceutical compositions of the present invention contain at least 50% of a crystalline form.

The pharmaceutical compositions comprising the crystalline forms of the KRas G12C inhibitor or salt thereof may be used in the methods of use described herein.

Methods of Use

The compositions and methods provided herein may be used for the treatment of a wide variety of cancers including tumors such as lung, colorectal, pancreas, prostate, breast, brain, skin, cervical carcinomas, testicular carcinomas, etc. More particularly, cancers that may be treated by the compositions and methods of the invention include, but are not limited to, tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

Also provided herein is a method for treating cancer in a subject in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a crystalline form of the KRas G12C inhibitor, alone or in combination with or pharmaceutically acceptable excipients and/or diluents. In one embodiment, the crystalline form is Form A. In another embodiment, the crystalline form is Form B. In one embodiment, the crystalline form is Form C. In another embodiment, the crystalline form is Form D. In one embodiment, the crystalline form is Form E. In one embodiment, the crystalline form is a mixture of any of Forms A-E.

In one embodiment, a crystalline form of the KRas G12C inhibitor is administered as a capsule during the period of time. In embodiments of the invention, a tablet or capsule comprises about 10 mg to about 1500 mg, for instance about 10 mg, about 20 mg, about 30 mg, about 40 mg, about 50 mg, about 60 mg, about 70 mg, about 0 mg, about 90 mg, about 100 mg, about 125 mg, about 150 mg, about 175 mg, about 200 mg, about 250 mg, about 300 mg, about 350 mg, about 400 mg, about 500 mg, about 600 mg, about 700 mg, about 800 mg, about 900 mg, about 1000 mg, about 1100 mg, about 1200 mg, about 1300 mg, about 1400 mg and about 1500 mg.

In one embodiment, the method comprises oral administration of a crystalline form once or twice a day on a daily basis (during a period of time), e.g., in an amount of about about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 250 mg, about 300 mg, about 350 mg, about 400 mg, about 500 mg, about 600 mg, about 700 mg, about 800 mg, about 900 mg, about 1000 mg, about 1100 mg, about 1200 mg, about 1300 mg, about 1400 mg and about 1500 mg. Oral administration of a crystalline form of the KRas G12C inhibitor occurs, for example, once a day on a daily basis (during a period of time). In one embodiment, the KRAS inhibitor is orally administered once daily. In one embodiment, the crystalline form of the KRAS G12C inhibitor is orally administered twice daily.

One skilled in the art will recognize that, both in vivo and in vitro trials using suitable, known and generally accepted cell and/or animal models are predictive of the ability of a test compound of the combination or the combination to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

In some embodiments, the methods provided herein can result in a 1% to 99% (e.g., 1% to 98%, 1% to 95%, 1% to 90%, 1 to 85%, 1 to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 1% to 5%, 2% to 99%, 2% to 90%, 2% to 85%, 2% to 80%, 2% to 75%, 2% to 70%, 2% to 65%, 2% to 60%, 2% to 55%, 2% to 50%, 2% to 45%, 2% to 40%, 2% to 35%, 2% to 30%, 2% to 25%, 2% to 20%, 2% to 15%, 2% to 10%, 2% to 5%, 4% to 99%, 4% to 95%, 4% to 90%, 4% to 85%, 4% to 80%, 4% to 75%, 4% to 70%, 4% to 65%, 4% to 60%, 4% to 55%, 4% to 50%, 4% to 45%, 4% to 40%, 4% to 35%, 4% to 30%, 4% to 25%, 4% to 20%, 4% to 15%, 4% to 10%, 6% to 99%, 6% to 90%, 6% to 85%, 6% to 80%, 6% to 75%, 6% to 70%, 6% to 65%, 6% to 60%, 6% to 55%, 6% to 50%, 6% to 45%, 6% to 40%, 6% to 35%, 6% to 30%, 6% to 25%, 6% to 20%, 6% to 15%, 6% to 10%, 8% to 99%, 8% to 95%, 8% to 90%, 8% to 85%, 8% to 80%, 8% to 75%, 8% to 70%, 8% to 65%, 8% to 60%, 8% to 55%, 8% to 50%, 8% to 45%, 8% to 40%, 8% to 35%, 8% to 30%, 8% to 25%, 8% to 20%, 8% to 15%, 10% to 99%, 10% to 95%, 10% to 90%, 10% to 85%, 10% to 80%, 10% to 75%, 10% to 70%, 10% to 65%, 10% to 60%, 10% to 55%, 10% to 50%, 10% to 45%, 10% to 40%, 10% to 35%, 10% to 30%, 10% to 25%, 10% to 20%, 10% to 15%, 15% to 99%, 15% to 95%, 15% to 90%, 15% to 85%, 15% to 80%, 15% to 75%, 15% to 70%, 15% to 65%, 15% to 60%, 15% to 55%, 15% to 50%, 15% to 55%, 15% to 50%, 15% to 45%, 15% to 40%, 15% to 35%, 15% to 30%, 15% to 25%, 15% to 20%, 20% to 99%, 20% to 95%, 20% to 90%, 20% to 85%, 20% to 80%, 20% to 75%, 20% to 70%, 20% to 65%, 20% to 60%, 20% to 55%, 20% to 50%, 20% to 45%, 20% to 40%, 20% to 35%, 20% to 30%, 20% to 25%, 25% to 99%, 25% to 95%, 25% to 90%, 25% to 85%, 25% to 80%, 25% to 75%, 25% to 70%, 25% to 65%, 25% to 60%, 25% to 55%, 25% to 50%, 25% to 45%, 25% to 40%, 25% to 35%, 25% to 30%, 30% to 99%, 30% to 95%, 30% to 90%, 30% to 85%, 30% to 80%, 30% to 75%, 30% to 70%, 30% to 65%, 30% to 60%, 30% to 55%, 30% to 50%, 30% to 45%, 30% to 40%, 30% to 35%, 35% to 99%, 35% to 95%, 35% to 90%, 35% to 85%, 35% to 80%, 35% to 75%, 35% to 70%, 35% to 65%, 35% to 60%, 35% to 55%, 35% to 50%, 35% to 45%, 35% to 40%, 40% to 99%, 40% to 95%, 40% to 90%, 40% to 85%, 40% to 80%, 40% to 75%, 40% to 70%, 40% to 65%, 40% to 60%, 40% to 55%, 40% to 60%, 40% to 55%, 40% to 50%, 40% to 45%, 45% to 99%, 45% to 95%, 45% to 95%, 45% to 90%, 45% to 85%, 45% to 80%, 45% to 75%, 45% to 70%, 45% to 65%, 45% to 60%, 45% to 55%, 45% to 50%, 50% to 99%, 50% to 95%, 50% to 90%, 50% to 85%, 50% to 80%, 50% to 75%, 50% to 70%, 50% to 65%, 50% to 60%, 50% to 55%, 55% to 99%, 55% to 95%, 55% to 90%, 55% to 85%, 55% to 80%, 55% to 75%, 55% to 70%, 55% to 65%, 55% to 60%, 60% to 99%, 60% to 95%, 60% to 90%, 60% to 85%, 60% to 80%, 60% to 75%, 60% to 70%, 60% to 65%, 65% to 99%, 60% to 95%, 60% to 90%, 60% to 85%, 60% to 80%, 60% to 75%, 60% to 70%, 60% to 65%, 70% to 99%, 70% to 95%, 70% to 90%, 70% to 85%, 70% to 80%, 70% to 75%, 75% to 99%, 75% to 95%, 75% to 90%, 75% to 85%, 75% to 80%, 80% to 99%, 80% to 95%, 80% to 90%, 80% to 85%, 85% to 99%, 85% to 95%, 85% to 90%, 90% to 99%, 90% to 95%, or 95% to 100%) reduction in the volume of one or more solid tumors in a patient following treatment with the combination therapy for a period of time between 1 day and 2 years (e.g., between 1 day and 22 months, between 1 day and 20 months, between 1 day and 18 months, between 1 day and 16 months, between 1 day and 14 months, between 1 day and 12 months, between 1 day and 10 months, between 1 day and 9 months, between 1 day and 8 months, between 1 day and 7 months, between 1 day and 6 months, between 1 day and 5 months, between 1 day and 4 months, between 1 day and 3 months, between 1 day and 2 months, between 1 day and 1 month, between one week and 2 years, between 1 week and 22 months, between 1 week and 20 months, between 1 week and 18 months, between 1 week and 16 months, between 1 week and 14 months, between 1 week and 12 months, between 1 week and 10 months, between 1 week and 9 months, between 1 week and 8 months, between 1 week and 7 months, between 1 week and 6 months, between 1 week and 5 months, between 1 week and 4 months, between 1 week and 3 months, between 1 week and 2 months, between 1 week and 1 month, between 2 weeks and 2 years, between 2 weeks and 22 months, between 2 weeks and 20 months, between 2 weeks and 18 months, between 2 weeks and 16 months, between 2 weeks and 14 months, between 2 weeks and 12 months, between 2 weeks and 10 months, between 2 weeks and 9 months, between 2 weeks and 8 months, between 2 weeks and 7 months, between 2 weeks and 6 months, between 2 weeks and 5 months, between 2 weeks and 4 months, between 2 weeks and 3 months, between 2 weeks and 2 months, between 2 weeks and 1 month, between 1 month and 2 years, between 1 month and 22 months, between 1 month and 20 months, between 1 month and 18 months, between 1 month and 16 months, between 1 month and 14 months, between 1 month and 12 months, between 1 month and 10 months, between 1 month and 9 months, between 1 month and 8 months, between 1 month and 7 months, between 1 month and 6 months, between 1 month and 6 months, between 1 month and 5 months, between 1 month and 4 months, between 1 month and 3 months, between 1 month and 2 months, between 2 months and 2 years, between 2 months and 22 months, between 2 months and 20 months, between 2 months and 18 months, between 2 months and 16 months, between 2 months and 14 months, between 2 months and 12 months, between 2 months and 10 months, between 2 months and 9 months, between 2 months and 8 months, between 2 months and 7 months, between 2 months and 6 months, or between 2 months and 5 months, between 2 months and 4 months, between 3 months and 2 years, between 3 months and 22 months, between 3 months and 20 months, between 3 months and 18 months, between 3 months and 16 months, between 3 months and 14 months, between 3 months and 12 months, between 3 months and 10 months, between 3 months and 8 months, between 3 months and 6 months, between 4 months and 2 years, between 4 months and 22 months, between 4 months and 20 months, between 4 months and 18 months, between 4 months and 16 months, between 4 months and 14 months, between 4 months and 12 months, between 4 months and 10 months, between 4 months and 8 months, between 4 months and 6 months, between 6 months and 2 years, between 6 months and 22 months, between 6 months and 20 months, between 6 months and 18 months, between 6 months and 16 months, between 6 months and 14 months, between 6 months and 12 months, between 6 months and 10 months, or between 6 months and 8 months) (e.g., as compared to the size of the one or more solid tumors in the patient prior to treatment).

The phrase "time of survival" means the length of time between the identification or diagnosis of cancer (e.g., any of the cancers described herein) in a mammal by a medical professional and the time of death of the mammal (caused by the cancer). Methods of increasing the time of survival in a mammal having a cancer are described herein.

In some embodiments, any of the methods described herein can result in an increase (e.g., a 1% to 400%, 1% to 380%, 1% to 360%, 1% to 340%, 1% to 320%, 1% to 300%, 1% to 280%, 1% to 260%, 1% to 240%, 1% to 220%, 1% to 200%, 1% to 180%, 1% to 160%, 1% to 140%, 1% to 120%, 1% to 100%, 1% to 95%, 1% to 90%, 1% to 85%, 1% to 80%, 1% to 75%, 1% to 70%, 1% to 65%, 1% to 60%, 1% to 55%, 1% to 50%, 1% to 45%, 1% to 40%, 1% to 35%, 1% to 30%, 1% to 25%, 1% to 20%, 1% to 15%, 1% to 10%, 1% to 5%, 5% to 400%, 5% to 380%, 5% to 360%, 5% to 340%, 5% to 320%, 5% to 300%, 5% to 280%, 5% to 260%, 5% to 240%, 5% to 220%, 5% to 200%, 5% to 180%, 5% to 160%, 5% to 140%, 5% to 120%, 5% to 100%, 5% to 90%, 5% to 80%, 5% to 70%, 5% to 60%, 5% to 50%, 5% to 40%, 5% to 30%, 5% to 20%, 5% to 10%, 10% to 400%, 10% to 380%, 10% to 360%, 10% to 340%, 10% to 320%, 10% to 300%, 10% to 280%, 10% to 260%, 10% to 240%, 10% to 220%, 10% to 200%, 10% to 180%, 10% to 160%, 10% to 140%, 10% to 120%, 10% to 100%, 10% to 90%, 10% to 80%, 10% to 70%, 10% to 60%, 10% to 50%, 10% to 40%, 10% to 30%, 10% to 20%, 20% to 400%, 20% to 380%, 20% to 360%, 20% to 340%, 20% to 320%, 20% to 300%, 20% to 280%, 20% to 260%, 20% to 240%, 20% to 220%, 20% to 200%, 20% to 180%, 20% to 160%, 20% to 140%, 20% to 120%, 20% to 100%, 20% to 90%, 20% to 80%, 20% to 70%, 20% to 60%, 20% to 50%, 20% to 40%, 20% to 30%, 30% to 400%, 30% to 380%, 30% to 360%, 30% to 340%, 30% to 320%, 30% to 300%, 30% to 280%, 30% to 260%, 30% to 240%, 30% to 220%, 30% to 200%, 30% to 180%, 30% to 160%, 30% to 140%, 30% to 120%, 30% to 100%, 30% to 90%, 30% to 80%, 30% to 70%, 30% to 60%, 30% to 50%, 30% to 40%, 40% to 400%, 40% to 380%, 40% to 360%, 40% to 340%, 40% to 320%, 40% to 300%, 40% to 280%, 40% to 260%, 40% to 240%, 40% to 220%, 40% to 200%, 40% to 180%, 40% to 160%, 40% to 140%, 40% to 120%, 40% to 100%, 40% to 90%, 40% to 80%, 40% to 70%, 40% to 60%, 40% to 50%, 50% to 400%, 50% to 380%, 50% to 360%, 50% to 340%, 50% to 320%, 50% to 300%, 50% to 280%, 50% to 260%, 50% to 240%, 50% to 220%, 50% to 200%, 50% to 180%, 50% to 160%, 50% to 140%, 50% to 120%, 50% to 100%, 50% to 90%, 50% to 80%, 50% to 70%, 50% to 60%, 60% to 400%, 60% to 380%, 60% to 360%, 60% to 340%, 60% to 320%, 60% to 300%, 60% to 280%, 60% to 260%, 60% to 240%, 60% to 220%, 60% to 200%, 60% to 180%, 60% to 160%, 60% to 140%, 60% to 120%, 60% to 100%, 60% to 90%, 60% to 80%, 60% to 70%, 70% to 400%, 70% to 380%, 70% to 360%, 70% to 340%, 70% to 320%, 70% to 300%, 70% to 280%, 70% to 260%, 70% to 240%, 70% to 220%, 70% to 200%, 70% to 180%, 70% to 160%, 70% to 140%, 70% to 120%, to 100%, 70% to 90%, 70% to 80%, 80% to 400%, 80% to 380%, 80% to 360%, 80% to 340%, 80% to 320%, 80% to 300%, 80% to 280%, 80% to 260%, 80% to 240%, 80% to 220%, 80% to 200%, 80% to 180%, 80% to 160%, 80% to 140%, 80% to 120%, 80% to 100%, 80% to 90%, 90% to 400%, 90% to 380%, 90% to 360%, 90% to 340%, 90% to 320%, 90% to 300%, 90% to 280%, 90% to 260%, 90% to 240%, 90% to 220%, 90% to 200%, 90% to 180%, 90% to 160%, 90% to 140%, 90% to 120%, 90% to 100%, 100% to 400%, 100% to 380%, 100% to 360%, 100% to 340%, 100% to 320%, 100% to 300%, 100% to 280%, 100% to 260%, 100% to 240%, 100% to 220%, 100% to 200%, 100% to 180%, 100% to 160%, 100% to 140%, 100% to 120%, 120% to 400%, 120% to 380%, 120% to 360%, 120% to 340%, 120% to 320%, 120% to 300%, 120% to 280%, 120% to 260%, 120% to 240%, 120% to 220%, 120% to 200%, 120% to 180%, 120% to 160%, 120% to 140%, 140% to 400%, 140% to 380%, 140% to 360%, 140% to 340%, 140% to 320%, 140% to 300%, 140% to 280%, 140% to 260%, 140% to 240%, 140% to 220%, 140% to 200%, 140% to 180%, 140% to 160%, 160% to 400%, 160% to 380%, 160% to 360%, 160% to 340%, 160% to 320%, 160% to 300%, 160% to 280%, 160% to 260%, 160% to 240%, 160% to 220%, 160% to 200%, 160% to 180%, 180% to 400%, 180% to 380%, 180% to 360%, 180% to 340%, 180% to 320%, 180% to 300%, 180% to 280%, 180% to 260%, 180% to 240%, 180% to 220%, 180% to 200%, 200% to 400%, 200% to 380%, 200% to 360%, 200% to 340%, 200% to 320%, 200% to 300%, 200% to 280%, 200% to 260%, 200% to 240%, 200% to 220%, 220% to 400%, 220% to 380%, 220% to 360%, 220% to 340%, 220% to 320%, 220% to 300%, 220% to 280%, 220% to 260%, 220% to 240%, 240% to 400%, 240% to 380%, 240% to 360%, 240% to 340%, 240% to 320%, 240% to 300%, 240% to 280%, 240% to 260%, 260% to 400%, 260% to 380%, 260% to 360%, 260% to 340%, 260% to 320%, 260% to 300%, 260% to 280%, 280% to 400%, 280% to 380%, 280% to 360%, 280% to 340%, 280% to 320%, 280% to 300%, 300% to 400%, 300% to 380%, 300% to 360%, 300% to 340%, or 300% to 320%) in the time of survival of the patient (e.g., as compared to a patient having a similar cancer and administered a different treatment or not receiving a treatment).

The following Examples are intended to illustrate further certain embodiments of the invention and are not intended to limit the scope of the invention.

Comparative Example 1

Preparation of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (amorphous)

This Example illustrates the preparation of amorphous free base of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile.

Step 1: Preparation of I07

N,N-dimethyl acetamide (3.75 w/w) was charged to a reactor followed by the addition of benzyl (S)-2-(cyanomethyl) piperazine-1-carboxylate (I05, 1 w/w). The reaction mixture was agitated for 5 min. and cooled to 20° C. Tert-butyl 2,4-dichloro-5,8-dihydropyrid (I06, 1.11 w/w) was then charged into the reactor (1.11 w/w), followed by slow addition of N,N-diisopropylethylamine (0.75 w/w). The reaction mixture was agitated until the reaction was complete (IPC HPLC, NMT 5% of I05) then diluted with ethyl acetate (9 w/w) and purified water (10 w/w). After 20-30 min., the reaction mixture was allowed to settle, and the aqueous and organic phases were separated. The aqueous phase was extracted back by ethyl acetate (4.5 w/w). The combined organic phase was washed sequentially three times by purified water (10 w/w), 10% sodium chloride solution (11 w/w), dried over Na2SO4 (0.5 w/w), and then filtered. The mixture was concentrated under reduced pressure and the resulting crude I07 was used in the subsequent step without further purification.

Step 2: Preparation of I09

The crude I07 was dissolved in 1,4-dioxane (23 w/w), (S)-(1-Methylpyrrolidin-2-yl), methanol (I08, 1.332 w/w) was then added, followed by cesium carbonate (3.77 w/w), and the resulting mixture was degassed with dry nitrogen for 15 min. RuPhos Pd G3 (0.323 w/w) was charged to the reaction mixture, and degassed with dry nitrogen for 15 min. after which time the reaction mixture temperature was raised to 110° C. After the reaction was deemed complete (IPC HPLC, NMT 5% of I07), the mixture was cooled to 25° C., diluted with ethyl acetate (18 w/w) and purified water (20.5 w/w). The resulting crude mixture was filtered through Celite (2 w/w) Nutsche Filter, and the reactor and filter bed were washed with ethyl acetate (4.5 w/w). The aqueous and organic phases were then separated. The aqueous phase was extracted back by ethyl acetate (4.5 w/w). The combined organic phase was washed twice sequentially with 1.5% L-Cysteine solution (21.33 w/w), 10% sodium chloride solution (22.35 w/w), dried over Na2SO4 (0.5 w/w), and filtered through Nutsche Filter. The reactor and the filter bed were washed with ethyl acetate (2 w/w). The organic phase was concentrated under reduced pressure and the resulting residue was purified by chromatography to afford I09.

Step 3: Preparation of I10

In a reactor, I09 was dissolved in dichloromethane (23 w/w) and trifluoro acetic acid (7.5 w/w) was slowly added. After the reaction was complete (IPC HPLC, NMT 5% of I09), the mixture was concentrated, diluted with ethyl acetate (22.5 w/w), and purified water (10 w/w). The organic phase was separated, washed with 1.5N HCl aq. solution (14 w/w) and the phases were separated. The combined aqueous phase was extracted twice with ethyl acetate (22.5 w/w). The phases were separated and the pH 8-10 of the aqueous phase was adjusted using potassium carbonate (2.5-5.0 w/w). The aqueous phase was extracted three times with dichloromethane (17 w/w). The combined organic phases were collected and washed with 10% sodium chloride solution (9.35 w/w), dried over Na2SO4 (0.5 w/w), filtered through Nutsche Filter. The reactor and the filter bed were washed with dichloromethane (2 w/w). The reaction mixture was concentrated under reduced pressure, and the resulting crude I10 was used in the following step without further purification.

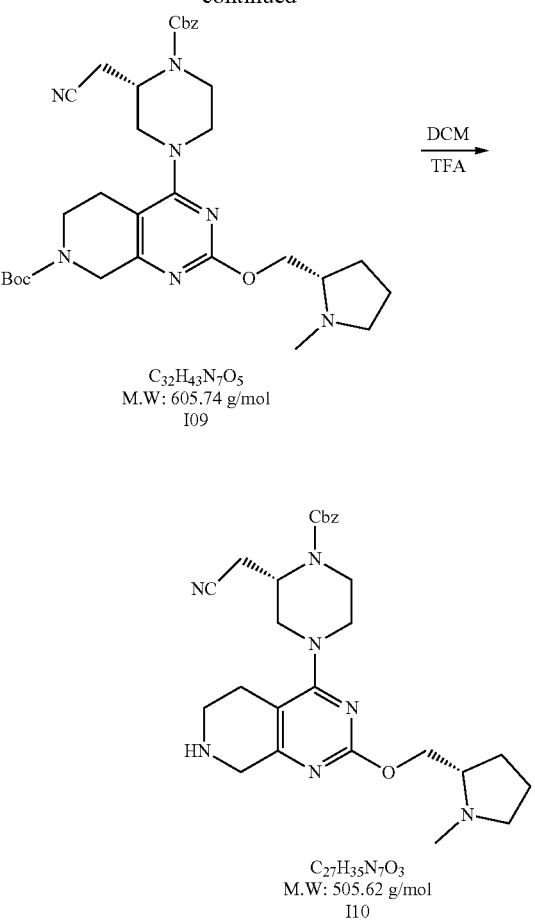

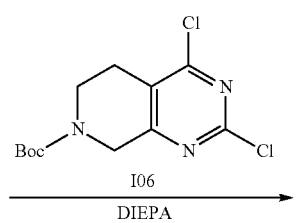

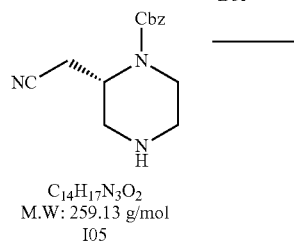

Step 4: Preparation of I15

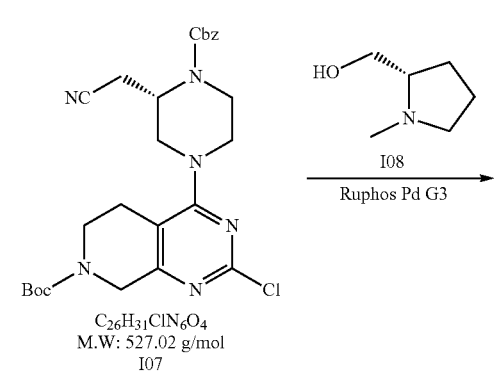

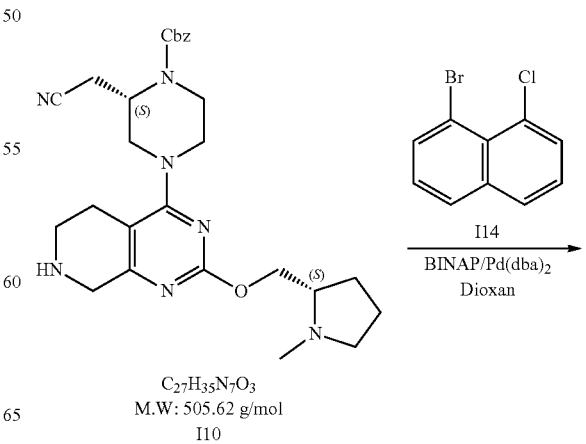

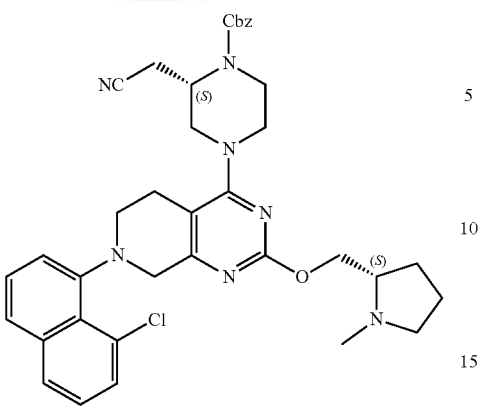

C$_{37}$H$_{40}$ClN$_7$O$_3$
M.W: 666.22
I15

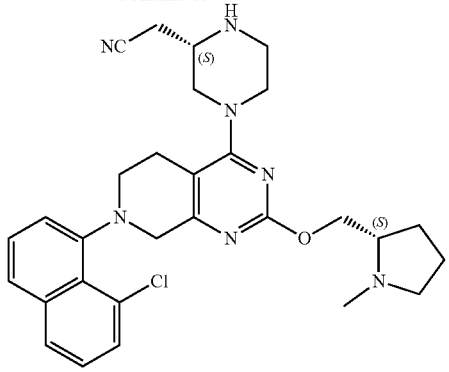

C$_{29}$H$_{34}$ClN$_7$O
M.W.: 532.09
I16

Step 5: Preparation of I16

1,4-dioxane (10.0 w/w) and I10 (1 w/w) were charged to a reactor. The reaction mixture was agitated for 10-15 min. and degassed with nitrogen. 1-bromo-8-chloro-naphthalene (I14, 0.96 w/w) and potassium phosphate tribasic (2.10 w/w) were added to the reactor. The reaction mixture was agitated for 10-15 min. and degassed with nitrogen. (R)-BINAP (0.25 w/w) was then added to the mixture at 25° C. followed by tris(dibenzylideneacetone)-dipalladium (0) (0.18 w/w). The reaction mixture temperature was raised to 75-80° C. and agitated for 12 hours. After reaction was complete (IPC HPLC, NMT 5% of I10), the mixture was cooled to 25° C. and filtered through a Celite bed. The filter bed was washed with ethyl acetate (4.5 w/w). The filtrate was diluted with water (5 w/w) and the phases were separated. The aqueous phase was extracted with ethyl acetate (4.5 w/w). The combined organic phase was washed with brine solution (1 w/w), dried over Na$_2$SO$_4$ (0.5 w/w) and concentrated under reduced pressure. The resulting residue was purified by chromatography to yield I15.

Acetonitrile (7 w/w) was charged to a reactor, agitated for 10-15 min under nitrogen atmosphere then I15 (1 w/w) was added, and the mixture was cooled to 10° C. TMSI (1.05 w/w) was added while maintaining the temperature at 10° C. After the addition was complete the temperature was raised to 20-25° C. and the mixture was further agitated for 2 hours. After reaction was deemed complete (IPC HPLC, NMT 5% of I15), the reaction mixture was quenched with aqueous sodium bisulphite solution (10.0 w/w), and the temperature was raised to 25° C. The reaction mixture was agitated for 15 min at 25° C. followed by the addition of ethyl acetate (10.0 w/w). The agitation was stopped, the phases were separated, and the organic phase was collected and washed with 10% sodium bisulphite solution (6.5 w/w). The two aqueous phases were combined, extracted with ethyl acetate (4.5 w/w), and the pH was adjusted to 9-10 using sodium carbonate. The mixture was further extracted with ethyl acetate (2×9 w/w). The combined organic phase was washed with water (5.0 w/w) followed by brine solution (0.5 w/w), dried over Na$_2$SO$_4$ (0.5 w/w), and concentrated under reduced pressure to afford I16.

Step 6: Preparation of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile

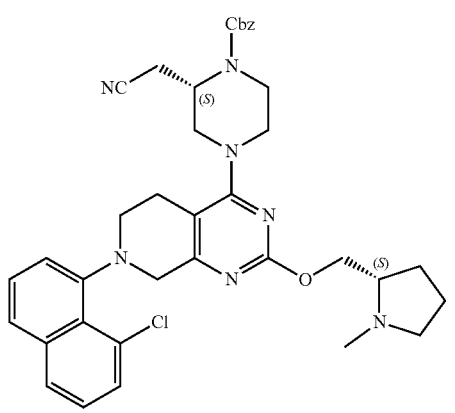

C$_{37}$H$_{40}$ClN$_7$O$_3$
M.W.: 666.22
I15

TMSI, ACN →

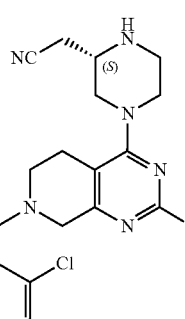

C$_{29}$H$_{34}$ClN$_2$O
MW: 532.09
I16

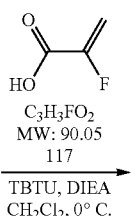

C$_3$H$_3$FO$_2$
MW: 90.05
117

TBTU, DIEA
CH$_2$Cl$_2$, 0° C. →

35
-continued

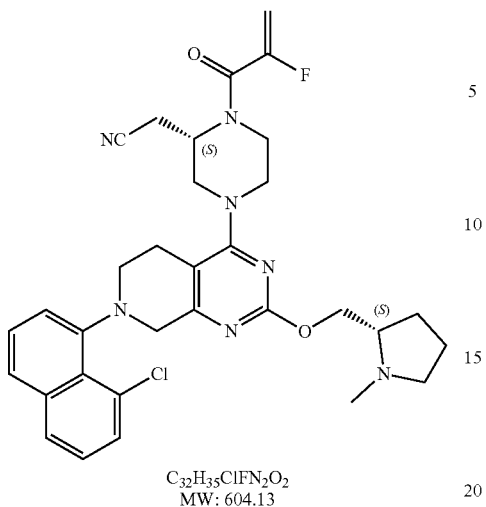

C₃₂H₃₅ClFN₂O₂
MW: 604.13

Dichloromethane (13 w/w) was charged to a reactor, agitated for 10-15 min under nitrogen atmosphere 2-fluoroacrylic acid (0.51 w/w), and TBTU (2.42 w/w) were then added. The reaction mixture was cooled to ~5° C., and DIEA (1.46 w/w) was added while maintaining the temperature at ~5° C. Dichloromethane (13 w/w/) and I16 (1 w/w) were then charged at 25° C. The crude mixture was further agitated for 1 hour at 25° C. and the reaction progress was monitored by an in-process HPLC. After reaction was deemed complete (IPC HPLC, NMT2% of 116), the crude mixture was diluted with 10% K$_2$CO$_3$ aqueous solution (10.0 w/w), agitated for additional 30 min. at 25° C. then filtered through a bed of celite. The phases were separated, and the organic phase was collected, concentrated and dissolved back in ethyl acetate (9 w/w) as organic phase-1. The aqueous phase was extracted by ethyl acetate (4.5 w/w), and the resulting aqueous and organic phase-2 were separated. The organic phases (1 and 2) were combined, washed with 10% K$_2$CO$_3$ aqueous solution (10.0 w/w), water (10 w/w), aqueous 10% sodium chloride solution (11 w/w) and concentrated under reduced pressure. The resulting residue was purified by chromatography eluting to yield 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile.

¹H NMR (400 MHz, Acetic) δ=7.82 (d, J=8.0 Hz, 1H), 7.69 (d, J=8.0 Hz, 1H), 7.56 (d, J=7.6 Hz, 1H), 7.49 (t, J=7.6 Hz, 1H), 7.41-7.30 (m, 2H), 5.58-5.25 (m, 2H), 5.17-4.59 (m, 4H), 4.57-4.28 (m, 3H), 4.24-3.78 (m, 4H), 3.67-3.13 (m, 7H), 3.08 (br d, J=2.4 Hz, 3H), 2.98 (br d, J=6.4 Hz, 1H), 2.83-2.61 (m, 1H), 2.45-2.29 (m, 1H), 2.24-2.08 (m, 3H).

The X-ray powder diffraction pattern of an amorphous preparation of yield 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile is shown in FIG. 1.

Comparative Example 2

Alternate Preparation 1 of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (amorphous)

Example 478 from WO2019/099524

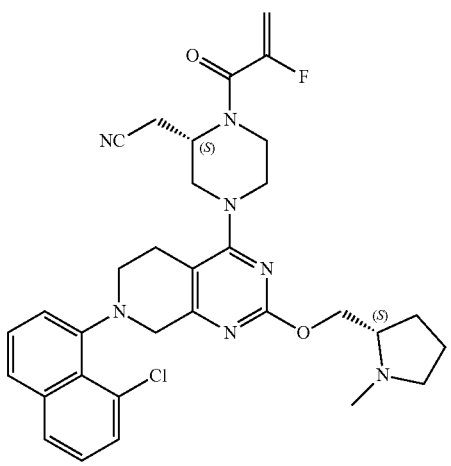

2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (amorphous)

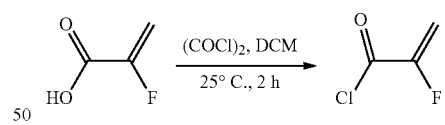

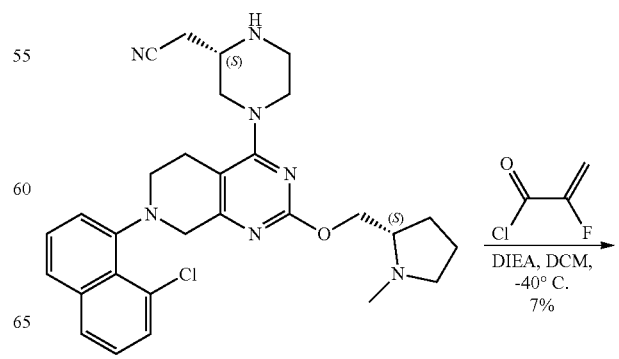

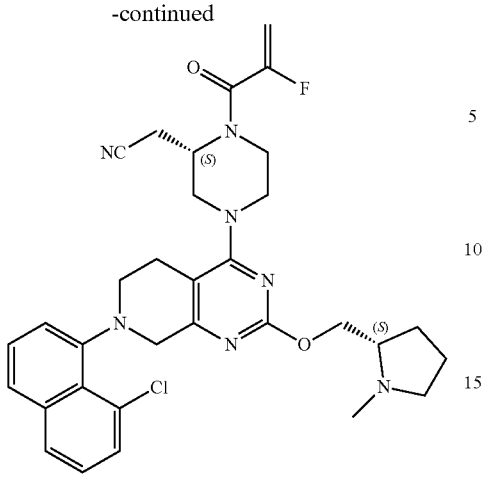

2-fluoroprop-2-enoyl chloride. To a solution of 2-fluoroprop-2-enoic acid (400 mg, 4.44 mmol, 1 eq) in DCM (4 mL) was added (COCl)$_2$ (846 mg, 6.66 mmol, 583 μL, 1.5 eq) and DMF (32.5 mg, 444 umol, 34.2 uL, 0.1 eq). The mixture was stirred at 25° C. for 2 hrs. The reaction mixture was concentrated under reduced pressure to remove a part of solvent and give a residue in DCM. Compound 2-fluoroprop-2-enoyl chloride (400 mg, crude) was obtained as a yellow liquid and used into the next step without further purification.

Step A: 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile. To a solution of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]piperazin-2-yl]acetonitrile (300 mg, 528 umol, 1 eq, HCl) in DCM (5 mL) was added DIEA (1.73 g, 13.4 mmol, 2.33 mL, 25.4 eq) and 2-fluoroprop-2-enoyl chloride (286 mg, 2.64 mmol, 5 eq) in DCM (5 mL). The mixture was stirred at 0° C. for 1 hour. The reaction mixture was concentrated under reduced pressure to give a residue. The residue was purified by column chromatography (Al$_2$O$_3$, Dichloromethane/Methanol=10/1 to 10/1). The residue was purified by prep-HPLC (column: Gemini 150*25 5u; mobile phase: [water (0.05% ammonia hydroxide v/v)-ACN]; B %: 55%-85%, 12 min). The residue was purified by prep-HPLC (column: Phenomenex Synergi C18 150*30 mm*4 um; mobile phase: [water (0.225% FA)-ACN]; B %: 20%-50%, 10.5 min). The residue was concentrated under reduced pressure to remove ACN, and then lyophilization. Title compound 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (EXAMPLE 478, 24.1 mg, 36.7 umol, 7% yield, 99.1% purity, FA) was obtained as a brown solid.

SFC condition: "AD—3S_3_5_40_3ML Column: Chiralpak AD—3 100×4.6 mm I.D., 3 um Mobile phase: methanol (0.05% DEA) in CO$_2$ from 5% to 40% Flow rate: 3 mL/min Wavelength: 220 nm".

$^1$H NMR (400 MHz, Acetic) δ=7.82 (d, J=8.0 Hz, 1H), 7.69 (d, J=8.0 Hz, 1H), 7.56 (d, J=7.6 Hz, 1H), 7.49 (t, J=7.6 Hz, 1H), 7.41-7.30 (m, 2H), 5.58-5.25 (m, 2H), 5.17-4.59 (m, 4H), 4.57-4.28 (m, 3H), 4.24-3.78 (m, 4H), 3.67-3.13 (m, 7H), 3.08 (br d, J=2.4 Hz, 3H), 2.98 (br d, J=6.4 Hz, 1H), 2.83-2.61 (m, 1H), 2.45-2.29 (m, 1H), 2.24-2.08 (m, 3H).

Comparative Example 3

Alternate Preparation 2 of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (amorphous)

Scheme 1. Synthesis

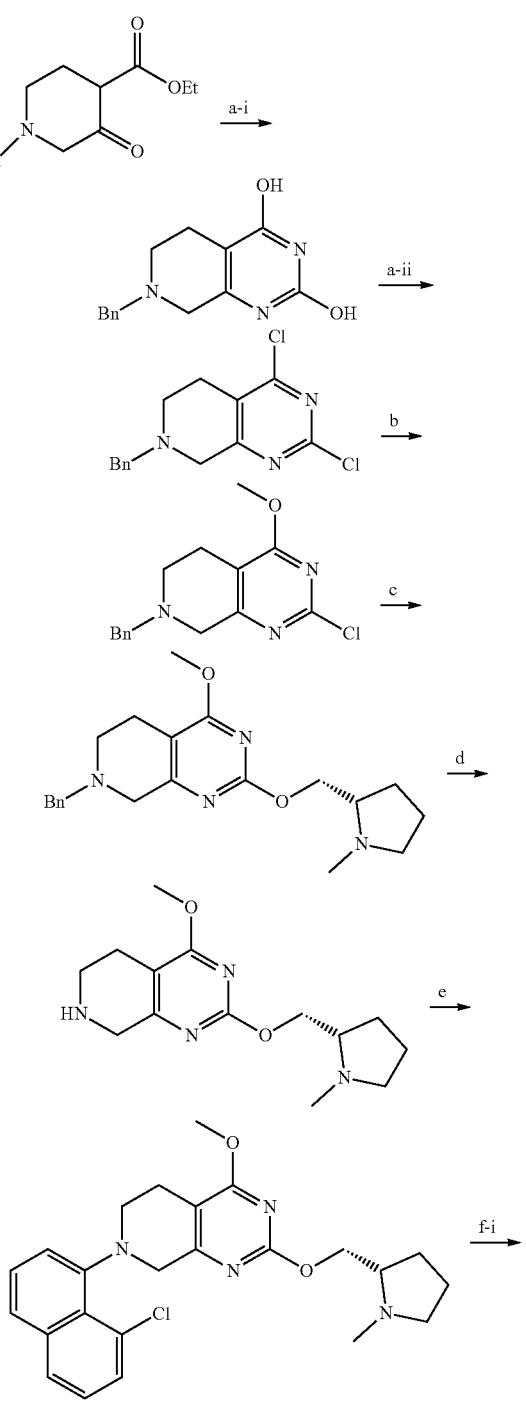

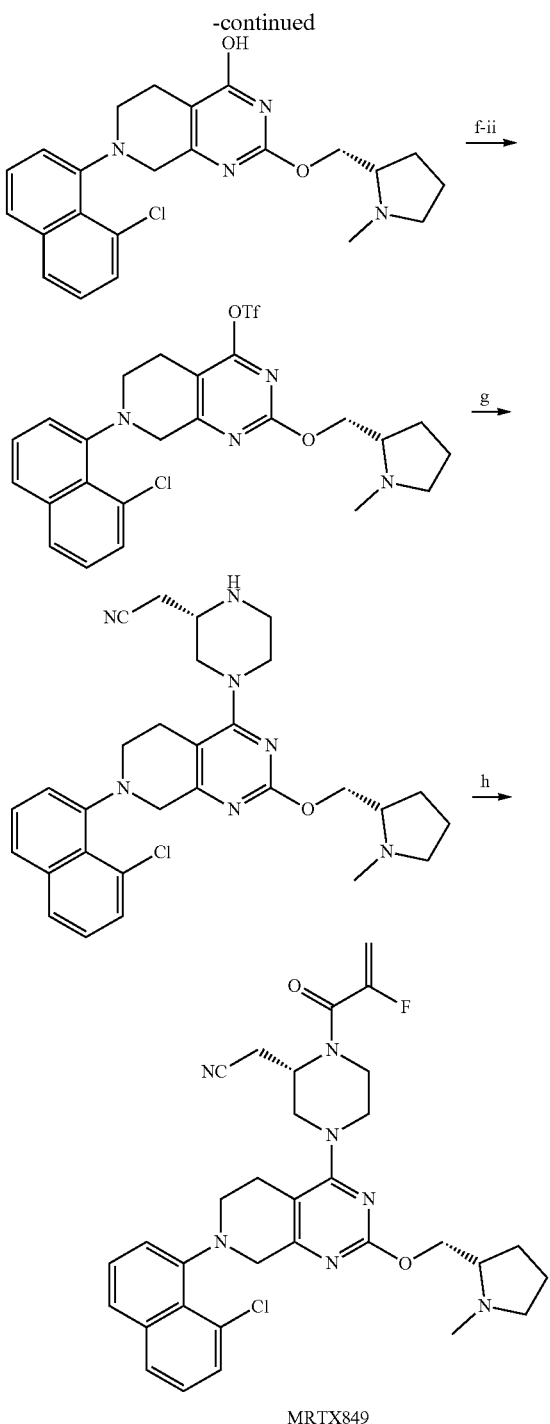

MRTX849

Reagents and Conditions. a) (i) urea, NaOEt/EtOH, 80° C., 20 h, 62%; (ii) POCl₃, 110° C., 12 h, 60%; b) NaOMe/MeOH 0-25° C., 30 min, 92%; c) (S)-(1-methylpyrrolidin-2-yl)methanol, rac-BINAP, Pd(OAc)₂, Cs₂CO₃, toluene, 110° C., 8 h, 83%; d) Pd(OH)2/C, H2, MeOH, 40° C. 48 h, 90%; e) Pd2(dba)3, RuPhos, Cs2CO3, toluene, 90° C., 10 h, 53%; f) (i) EtSH, NaH, DMF, 60° C., 1 h, 94%; (ii) Tf₂O, TEA, 4 Å MS, DCM, −40° C., 30 min, 20%; g) (S)-2-(piperazin-2-yl)acetonitrile, DIEA, DMA, rt, 15 min, 44%; h) 2-fluoroprop-2-enoic acid, T3P, TEA, 0° C., 30 min, 29%.

7-Benzyl-5,6,7,8-tetrahydropyrido[3,4-d]pyrimidine-2,4-diol: Na (46.3 g, 2.01 mol, 4.0 equiv) was added portionwise to anhydrous EtOH (2.5 L). The reaction mixture was stirred at 60° C. for 30 min until the suspension became homogeneous. To the resultant solution was added urea (90.8 g, 1.51 mol, 3.0 equiv) and the mixture was stirred for 10 min until the urea was dissolved. To the solution was added ethyl 1-benzyl-3-oxopiperidine-4-carboxylate-HCl salt (150 g, 504 mmol, 1.0 equiv). The mixture was stirred at 80° C. for 20 h and subsequently concentrated under reduced pressure to provide the crude residue. The residue was dissolved in water (1 L) and acidified to pH=6 with HCl (12N, 80 mL). The solid was collected by filtration and washed with MTBE (600 mL). The solid was azeotropically dried with toluene to afford 7-benzyl-5,6,7,8-tetrahydropyrido[3,4-d]pyrimidine-2,4-diol (80.0 g, 62% yield) as a white solid.

7-Benzyl-2,4-dichloro-5,6,7,8-tetrahydropyrido[3,4-d]pyrimidine: A mixture of 7-benzyl-5,6,7,8-tetrahydropyrido[3,4-d]pyrimidine-2,4-diol (80.0 g, 311 mmol, 1.0 equiv) in POCl₃ (750 mL, 8.07 mol, 26 equiv) was stirred at 110° C. for 12 h. The reaction mixture was concentrated to dryness under reduced pressure. The residue was dissolved in ethyl acetate (1 L) and diluted with satd aq Na₂CO₃ (500 mL). The mixture was separated and the organic solvent was dried over anh Na₂SO₄, filtered through a pad of silica gel, and concentrated under reduced pressure. The resultant residue was purified by flash chromatography (SiO₂, petroleum ether/ethyl acetate, 10/1 to 1/1) to afford 7-benzyl-2,4-dichloro-5,6,7,8-tetrahydropyrido[3,4-d]pyrimidine (55 g, 60% yield) as a white solid, LCMS [ESI, M+1]: 294.

7-Benzyl-2-chloro-4-methoxy-5,6,7,8-tetrahydropyrido[3,4-d]pyrimidine: To a solution of 7-benzyl-2,4-dichloro-5,6,7,8-tetrahydropyrido[3,4-d]pyrimidine (100 g, 340 mmol, 1.0 equiv) in MeOH (2 L) was added sodium methoxide (22.0 g, 408 mmol, 1.2 equiv) at 0° C. After stirring at 25° C. for 30 min, the mixture was acidified to pH 7 with aqueous 2 N HCl. To the resultant mixture was added water (1 L) and the suspension was filtered and the solid was washed with water (200 mL). The filter cake was dissolved in ethyl acetate (1 L) and washed with water (500 mL) and brine (500 mL). The organic phase was separated, dried over sodium sulfate, filtered and the filtrate was concentrated under reduced pressure to provide 7-benzyl-2-chloro-4-methoxy-5,6,7,8-tetrahydropyrido[3,4-d]pyrimidine (92.0 g, 92% yield); white solid; HPLC: >98%; 1'H NMR (400 MHz, CDCl3) δ 7.36-7.06 (m, 5H), 3.92 (s, 3H), 3.65-3.55 (m, 2H), 3.46 (s, 2H), 2.66 (t, J=6.0, 2H), 2.55 (t, J=5.6, 2H); LCMS [ESI, M+1]: 290.

(S)-7-Benzyl-4-methoxy-2-((1-methylpyrrolidin-2-yl)methoxy)-5,6,7,8-tetrahydropyrido[3,4-d]pyrimidine: To a mixture of 7-benzyl-2-chloro-4-methoxy-5,6,7,8-tetrahydropyrido[3,4-d]pyrimidine (92.0 g, 318 mmol, 1.0 equiv), [(2S)-1-methylpyrrolidin-2-yl]methanol (73.1 g, 635 mmol, 75.4 mL, 2 equiv) in toluene (2 L) was added palladium acetate (7.13 g, 31.8 mmol, 0.1 equiv), rac-BINAP (39.5 g, 63.5 mmol, 0.2 equiv) and cesium carbonate (310 g, 953 mmol, 3 equiv) under an atmosphere of nitrogen. The reaction mixture was purged with nitrogen 3 times and was then stirred at 110° C. for 8 h under nitrogen. The mixture was cooled to room temperature, filtered and diluted with ethyl acetate (1.5 L). The mixture was acidified with aqueous 1 N HCl to pH 3~4 and washed with ethyl acetate (1 L). The aqueous layer was neutralized with saturated aqueous sodium carbonate solution to pH 8-9 and extracted with ethyl acetate (3×1.5 L). The combined organic phase was dried over anh sodium sulfate, filtered and concentrated under reduced pressure to provide (S)-7-benzyl-4-methoxy-2-((1-methylpyrrolidin-2-yl)methoxy)-5,6,7,8-tetrahydropyrido[3,4-d]pyrimidine (103 g, 83% yield); yellow oil; $^1$H NMR (400 MHz, CDCl$_3$) δ 7.31-7.16 (m, 5H), 4.30 (dd, J=5.2, 10.8 Hz, 1H), 4.11-4.01 (m, 1H), 3.88 (s, 3H), 3.60 (s, 2H), 3.42 (s, 2H), 3.00 (br t, J=7.6 Hz, 1H), 2.71-2.45 (m, 5H), 2.38 (s, 3H), 2.18 (dt, J=7.2, 9.2 Hz, 1H), 2.04-1.88 (m, 1H), 1.82-1.55 (m, 3H); LCMS [ESI, M+1]: 369.

(S)-4-Methoxy-2-((1-methylpyrrolidin-2-yl)methoxy)-5,6,7,8-tetrahydropyrido[3,4-d]pyrimidine: To a solution of (S)-7-benzyl-4-methoxy-2-((1-methylpyrrolidin-2-yl)methoxy)-5,6,7,8-tetrahydropyrido[3,4-d]pyrimidine (58.0 g, 157 mmol, 1.0 equiv) in MeOH (1 L) was added Pd(OH)$_2$/C (10.0 g, 20 wt. %, 27.1 mmol). The mixture was stirred at 40° C. for 48 h under hydrogen gas (45 psi). The mixture was purged with nitrogen, filtered and the filtrate was concentrated under reduced pressure to provide (S)-4-methoxy-2-((1-methylpyrrolidin-2-yl)methoxy)-5,6,7,8-tetrahydropyrido[3,4-d]pyrimidine (41.0 g, 90% yield); yellow oil; $^1$H NMR (400 MHz, CDCl$_3$) δ 4.37 (dd, J=4.8, 10.4 Hz, 1H), 4.13 (dt, J=7.2, 10.4 Hz, 1H), 3.95 (s, 3H), 3.83 (s, 2H), 3.09-3.01 (m, 3H), 2.69-2.58 (m, 1H), 2.49 (t, J=5.6 Hz, 2H), 2.45-2.41 (m, 1H), 2.46-2.39 (m, 2H), 2.24 (dt, J=7.2, 9.2 Hz, 1H), 2.08-2.01 (m, 1H), 1.85-1.63 (m, 3H). LCMS [ESI, M+1]: 279.

(S)-7-(8-Chloronaphthalen-1-yl)-4-methoxy-2-((1-methylpyrrolidin-2-yl)methoxy)-5,6,7,8-tetrahydropyrido[3,4-d]pyrimidine: To a mixture of (S)-4-methoxy-2-((1-methylpyrrolidin-2-yl)methoxy)-5,6,7,8-tetrahydropyrido[3,4-d]pyrimidine (60 g, 215 mmol, 1 equiv) and 1-bromo-8-chloro-naphthalene (67.9 g, 280 mmol, 1.3 equiv) in toluene (1 L) was added RuPhos (40.2 g, 86.2 mmol, 0.4 equiv), Pd$_2$(dba)$_3$ (39.5 g, 43.1 mmol, 0.2 equiv), Cs$_2$CO$_3$ (175 g, 539 mmol, 2.5 equiv) under nitrogen. The mixture was stirred at 90° C. for 10 h under nitrogen. The mixture was cooled to room temperature and was filtered through Celite; the filter cake was washed with ethyl acetate (1.50 L×2). The filtrate was adjusted to pH 2 with 1.0 M aqueous HCl and was washed with ethyl acetate (1 L×2) and separated. The water layer was slowly neutralized with solid Na$_2$CO$_3$ and was then extracted with ethyl acetate (1.5 L×3). The combined organic layer was dried over Na$_2$SO$_4$, filtered and concentrated under reduced pressure. The resultant residue was purified by flash chromatography (petroleum ether/ethyl acetate, 3:1 then ethyl acetate/methanol, 10:1) to provide (S)-7-(8-chloronaphthalen-1-yl)-4-methoxy-2-((1-methylpyrrolidin-2-yl)methoxy)-5,6,7,8-tetrahydropyrido[3,4-d]pyrimidine (52 g, 53% yield). Yellow solid; $^1$H NMR (400 MHz, CDCl3) δ 7.76-7.71 (m, 1H), 7.61-7.57 (m, 1H), 7.53-7.48 (m, 1H), 7.45-7.40 (m, 1H), 7.34-7.29 (m, 1H), 7.24-7.20 (m, 1H), 4.49-4.40 (m, 1H), 4.34-4.25 (m, 1H), 4.19 (ddd, J=4.8, 7.2, 10.8 Hz, 1H), 4.02 (s, 3H), 3.87 (dd, J=0.8, 17.2 Hz, 1H), 3.64-3.53 (m, 1H), 3.23-3.13 (m, 1H), 3.12-3.05 (m, 11H), 3.03-2.93 (m, 1H), 2.74-2.57 (m, 2H), 2.49 (s, 3H), 2.31-2.23 (m, 1H), 2.05 (s, 1H), 1.90-1.75 (m, 3H); LCMS [ESI, M+1]: 439.

(S)-7-(8-Chloronaphthalen-1-yl)-2-((1-methylpyrrolidin-2-yl)methoxy)-5,6,7,8-tetrahydropyrido[3,4-d]pyrimidin-4-ol: To a solution of NaH (3.19 g, 79.7 mmol, 60 wt. %, 2.0 equiv) in DMF (200 mL) was added EtSH (10.1 mL, 137 mmol, 3.4 equiv) at 0° C. over 30 min. To this mixture was added a solution of (S)-7-(8-chloronaphthalen-1-yl)-4-methoxy-2-((1-methylpyrrolidin-2-yl)methoxy)-5,6,7,8-tetrahydropyrido[3,4-d]pyrimidine (17.5 g, 39.87 mmol, 1.0 equiv) in DMF (200 mL). The mixture was stirred at 60° C. for 1 h. The mixture was cooled to 0° C. and diluted with saturated aqueous NH$_4$Cl (200 mL). The aqueous layer was extracted with ethyl acetate (150 mL×2) and chloroform (150 mL×2) and the combined organic layer was dried over anhydrous Na$_2$SO$_4$, filtered and concentrated under reduced pressure. The crude residue was purified by column chromatography [Al$_2$O$_3$, petroleum ether/ethyl acetate, 1:1 to ethyl acetate/ethanol (2% NH$_4$OH), 1:1] to afford (S)-7-(8-chloronaphthalen-1-yl)-2-((1-methylpyrrolidin-2-yl)methoxy)-5,6,7,8-tetrahydropyrido[3,4-d]pyrimidin-4-ol (16.5 g, 94%). Yellow solid; Rf=0.05 [4:3:1, petroleum ether/ethyl acetate/ethanol (2% NH$_4$OH]; $^1$H NMR (400 MHz, CDCl3) δ 7.77-7.71 (m, 1H), 7.58 (d, J=8.0 Hz, 1H), 7.51 (d, J=7.6 Hz, 1H), 7.42 (dt, J=2.0, 7.6 Hz, 1H), 7.37-7.28 (m, 1H), 7.22 (d, J=7.6 Hz, 1H), 4.60-4.33 (m, 2H), 4.15-4.08 (m, 11H), 3.75-3.67 (m, 1H), 3.54 (br dd, J=2.4, 9.2 Hz, 1H), 3.47 (s, 1H), 3.34-3.19 (m, 1H), 3.18-3.05 (m, 1H), 3.00-2.73 (m, 2H), 2.57 (d, J=9.6 Hz, 3H), 2.50-2.33 (m, 1H), 2.07-1.78 (m, 4H), 1.32-1.17 (m, 1H); LCMS [ESI, M+1]: 425.

(S)-7-(8-Chloronaphthalen-1-yl)-2-((1-methylpyrrolidin-2-yl)methoxy)-5,6,7,8-tetrahydropyrido[3,4-d]pyrimidin-4-yl trifluoromethanesulfonate: To a suspension of (S)-7-(8-chloronaphthalen-1-yl)-2-((1-methylpyrrolidin-2-yl)methoxy)-5,6,7,8-tetrahydropyrido[3,4-d]pyrimidin-4-ol (500 mg, 1.18 mmol, 1.0 equiv) and 4 Å MS (300 mg) in dichloromethane (3.0 mL) was added Tf$_2$O (388 μL, 2.35 mmol, 2.0 equiv) and TEA (819 μL, 5.88 mmol, 5.0 equiv) at −40° C. The mixture was stirred at −40° C. for 30 min. Subsequently, the mixture was concentrated under reduced pressure. The resultant residue was purified by column chromatography (SiO$_2$, petroleum ether/ethyl acetate, 10:1 to 1:1) to afford (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (134 mg, 20% yield). Yellow solid; Rf=0.05 (petroleum ether/ethyl acetate, 3:1); $^1$H NMR (400 MHz, CDCl$_3$) δ 7.77 (dd, J=0.8, 8.0 Hz, 1H), 7.65 (d, J=7.6 Hz, 1H), 7.54 (dd, J=1.2, 7.6 Hz, 1H), 7.46 (t, J=7.6 Hz, 1H), 7.35 (t, J=7.6 Hz, 1H), 7.26-7.21 (m, 1H), 4.50-4.36 (m, 2H), 4.25 (ddd, J=3.6, 6.4, 10.4 Hz, 1H), 3.97 (d, J=18.0 Hz, 1H), 3.72-3.60 (m, 1H), 3.31-3.06 (m, 3H), 2.85-2.64 (m, 2H), 2.49 (s, 3H), 2.37-2.25 (m, 1H), 2.13-2.05 (m, 1H), 1.93-1.72 (m, 3H)); LCMS [ESI, M+1]: 557.

2-((S)-4-(7-(8-Chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile: To a solution of (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (11.0 g, 10.6 mmol, 54% purity, 1.0 equiv) in DMA (100 mL) was added (S)-2-(piperazin-2-yl)acetonitrile (1.47 g, 11.7 mmol, 1.1 equiv) and DIEA (3.71 mL, 21.3 mmol, 2.0 equiv) at 15° C. The mixture was stirred at 15° C. for 15 min. Subsequently, the reaction mixture was concentrated under reduced pressure give a residue. The crude residue was purified by reversed phase flash chromatography [water, acetonitrile (0.1% FA)] to afford 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl)acetonitrile (2.5 g, 44%). Yellow solid; $^1$H NMR (400 MHz, CDCl3) δ 7.75 (d, J=8.0 Hz, 1H), 7.61 (dd, J=2.4, 8.0 Hz, 1H), 7.55-7.49 (m, 1H), 7.39-7.29 (m, 2H), 7.26-7.19 (m, 1H), 4.51-4.32 (m, 2H), 4.18-4.12 (m, 1H), 4.07-3.90 (m, 1H), 3.90-3.70 (m, 2H), 3.62-3.48 (m, 1H), 3.37-3.19 (m, 1H), 3.18-3.02 (m, 5H), 3.01-2.79 (m, 2H), 2.67 (br dd, J=4.8, 6.8 Hz, 1H), 2.59-2.48 (m, 3H), 2.48 (d, J=2.8 Hz, 3H), 2.34-2.21 (m, 1H), 2.12-2.04 (m, 1H), 1.79-1.69 (m, 3H). LCMS [ESI, M+1]: 532.

2-((S)-4-(7-(8-Chloronaphthalen-1-yl)-2-(((S)-1-methylpyrrolidin-2-yl)methoxy)-5,6,7,8-tetrahydropyrido[3,4-d]

pyrimidin-4-yl)-1-(2-fluoroacryloyl)piperazin-2-yl)acetonitrile: To a suspension of 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)piperazin-2-yl) acetonitrile (80 mg, 1.50 mmol, 1.0 equiv) and 4 Å molecular sieves (500 mg) in ethyl acetate (5.0 mL) at 0° C. was added triethylamine (1.67 mL, 12.0 mmol, 8.0 equiv), 2-fluoroprop-2-enoic acid (271 mg, 3.01 mmol, 2.0 equiv) and T3P (2.68 mL, 4.51 mmol, 50 wt. % in ethyl acetate, 3.0 equiv). The mixture was warmed to 15° C. over 30 min and the reaction mixture was diluted with satd aq sodium carbonate (20 mL). The aqueous phase was extracted with ethyl acetate (2×20 mL) and the combined organic layer was dried over anh sodium sulfate, filtered and concentrated to provide the crude residue. The residue was purified by prep-HPLC; column: Waters Xbridge C18 150×50 mm×10 m, mobile phase: A [water (10 mM NH4HCO3)], B (ACN), B %: 42%-72%, 11.5 min); to afford 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile (263 mg, 29%). Off-white solid; mp 91.0-117.5° C.; HPLC: 98.9%; SFC: 100% ee, Chiralpak column (IC-3 50×4.6 mm I.D. 3 μm), 60% CH$_3$OH 40% CH$_3$CN (0.05% DEA), 3 mL/min flow rate, 220 nm detector, column temperature: 35° C., back pressure: 100 Bar, tR: 1.108 min; [α]D (25° C.): −0.672° (c=0.138 g/100 mL, CH3CN); 1H NMR (400 MHz, CDCl3) δ 7.76 (td, J=1.6, 8.0 Hz, 1H), 7.62 (t, J=7.2 Hz, 1H), 7.53 (d, J=7.6 Hz, 1H), 7.45 (td, J=7.6, 13.2 Hz, 1H), 7.37-7.31 (m, 1H), 7.27-7.18 (m, 1H), 5.51-5.33 (m, 1H), 5.25 (dd, J=3.6, 16.8 Hz, 1H), 5.10-4.58 (m, 1H), 4.48-4.35 (m, 2H), 4.19-4.01 (m, 3H), 3.99-3.74 (m, 2H), 3.63-3.56 (m, 1H), 3.43 (br d, J=12.8 Hz, 1H), 3.30-3.02 (m, 5H), 2.96-2.74 (m, 2H), 2.72-2.53 (m, 2H), 2.48 (d, J=2.0 Hz, 3H), 2.28 (ddt, J=2.0, 7.2, 9.6 Hz, 1H), 2.12-1.99 (m, 1H), 1.88-1.69 (m, 3H); 13C NMR (100 MHz, CDCl$_3$): δ 166.3, 166.1, 162.6, 158.0, 155.3, 148.4, 148.0, 137.2, 130.0, 129.6, 128.2, 126.4, 125.9, 125.6, 125.1, 124.9, 118.5, 116.7, 109.2, 101.4, 69.9, 63.8, 59.0, 58.6, 57.6, 50.3, 48.0, 41.7, 29.1, 26.1, 25.4, 22.9; HRMS (ESI+) calcd for 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, C32H35ClFN7O2H+ (M+H+) 604.2598, found 604.2602.

Comparative Example 4

Alternate Preparation 3 of 2-[(2S)-4-[7-(8-chloro-1-naphthyl)-2-[[(2S)-1-methylpyrrolidin-2-yl] methoxy]-6,8-dihydro-5H-pyrido[3,4-d]pyrimidin-4-yl]-1-(2-fluoroprop-2-enoyl)piperazin-2-yl] acetonitrile (amorphous)

Approximately 0.5 g of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile was dissolved in methanol (~16 ml) at ambient temperature. The solution was fed to the nozzle of a spray dryer and atomized into droplets rapidly dried into particles by a hot nitrogen gas stream. A BLD-35 spray dryer was used with a solution flow rate of ~25-35 g/min, pressure swirl Schlick 2.0 atomizer, 120 psig atomization pressure and outlet temperature of 45° C. Secondary drying of the resulting material was performed in a tray dryer at 30° C. for approximately 19 hours.

Example 1

Example 1A: Preparation of Crystalline Form A of 2-[(2S)-4-[7-(8-chloro-1-naphthyl)-2-[[(2S)-1-methylpyrrolidin-2-yl]methoxy]-6,8-dihydro-5H-pyrido [3,4-d]pyrimidin-4-yl]-1-(2-fluoroprop-2-enoyl)piperazin-2-yl]acetonitrile A 700 mg, f 1 mg amount of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile was weighed into a 20 ml vial and heptane (10 vol, 7 ml) was added at 80° C. After 24 h of maturation with temperature cycling between 25° C. and 80° C., an aliquot of the suspension was analyzed by XRPD and was determined to be partially crystalline. Solids that had formed on the vial sides were scraped back into the suspension and maturation continued for 24 hours of cycling 25° C./80° C. After the heptane had completely evaporated, a second volume of heptane (10 vol, 7 ml) was added and maturation continued for an additional period. After 96 hours of maturation, the sample was completely evaporated. The resulting solid material was analyzed by XRPD, which showed crystalline material. The sample was dried for 2 h in a vacuum oven. The X-ray powder diffraction pattern of a 2 hr dried sample of crystalline Form A is shown in FIG. 1A and observed diffraction peaks are listed in Table 1. Characteristic peaks are marked with an asterisk.

Figure 1B:
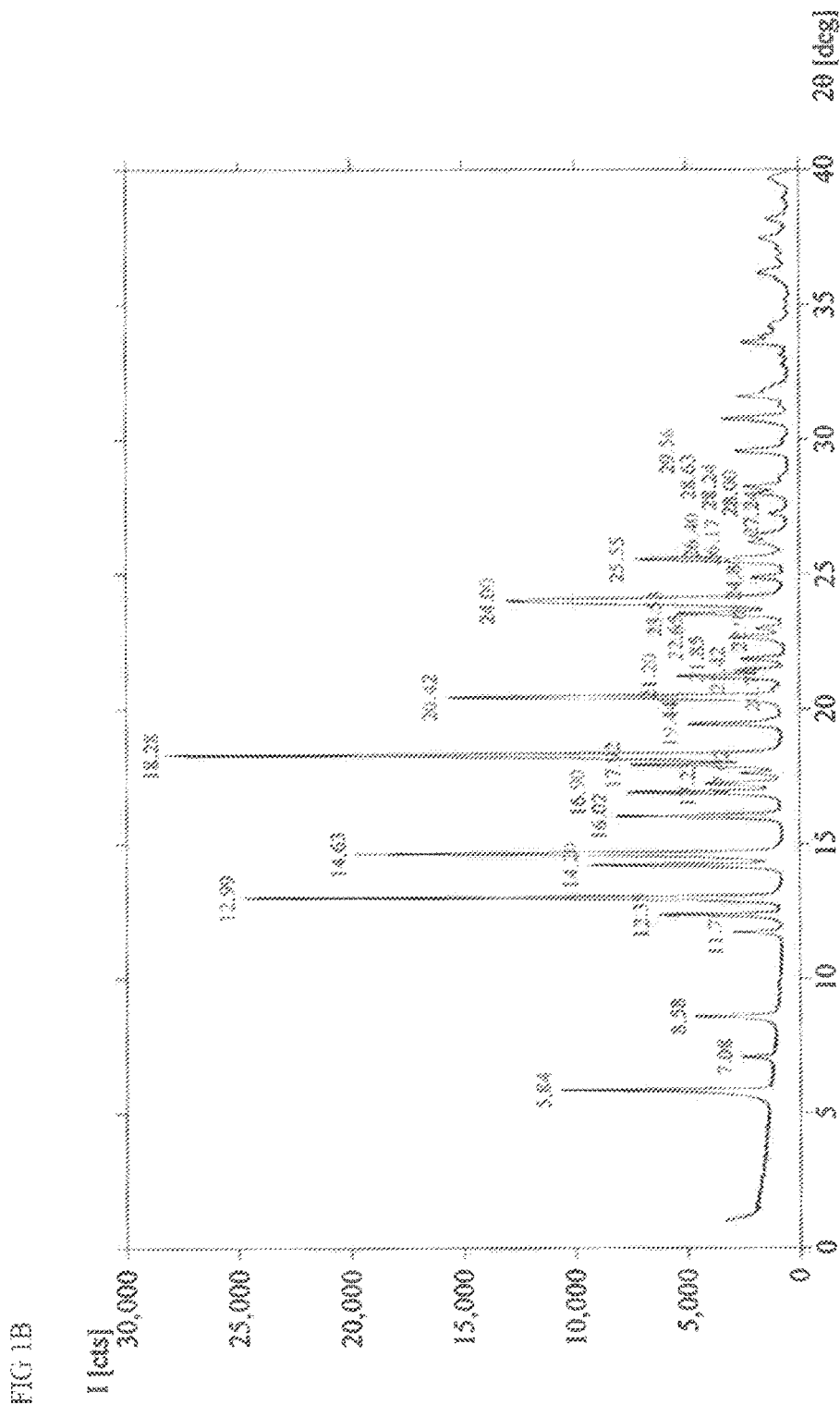

Example 1B: First Additional Preparation of Crystalline Form A of 2-[(2S)-4-[7-(8-chloro-1-naphthyl)-2-[[(2S)-1-methylpyrrolidin-2-yl]methoxy]-6, 8-dihydro-5H-pyrido[3,4-d]pyrimidin-4-yl]-1-(2-fluoroprop-2-enoyl)piperazin-2-yl]acetonitrile In a 20 L jacketed reactor, 2.1 kg amorphous of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile was dissolved in 14 L of a solvent mixture IPA:MTBE 4:1 v:v at 52° C. and aged for 10 min. The solution was cooled to 50° C. in 10 min and aged for 10 min. 42 g of 2-[(2S)-4-[7-(8-chloro-1-naphthyl)-2-[[(2S)-1-methylpyrrolidin-2-yl] methoxy]-6,8-dihydro-5H-pyrido[3,4-d]pyrimidin-4-yl]-1-(2-fluoroprop-2-enoyl)piperazin-2-yl]acetonitrile Form A seeds were added dry and aged for 1 h. The resulting suspension was cooled to 25° C. at 0.028° C./min with aging at 35° C. for 8 h, at 30° C. for 4 h, and at 25° C. for approximately 12 h, filtered with vacuum pull at room temperature for approximately 12 h then dried at approximately 40° C. under vacuum for approximately 72 h. The resulting solid material was analyzed by XRPD, which showed crystalline material. The X-ray powder diffraction pattern of a 2 hr dried sample of crystalline Form A is shown in FIG. 1B, and observed peaks and percent peak intensities obtained from the XRPD analysis are listed in Table 1.

Example 1C: Second Additional Preparation of Crystalline Form A of 2-[(2S)-4-[7-(8-chloro-1-naphthyl)-2-[[(2S)-1-methylpyrrolidin-2-yl] methoxy]-6,8-dihydro-5H-pyrido[3,4-d]pyrimidin-4-yl]-1-(2-fluoroprop-2-enoyl)piperazin-2-yl] acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d] pyrimidin-4-yl]-1-(2-fluoroprop-2-enoyl)piperazin-2-yl]acetonitrile (115.2 mg) was dissolved in IPA (2.2 ml) at 50° C. Approximately half of the solution was filtered through a 0.2 µm nylon filter and placed into a 1-dram vial. The 1-dram vial was then capped and placed into a shaker block at 6° C. Solids were observed after 7 days. The solvent was decanted and solids were left uncapped in the vial for drying. After 1 hour the vial was capped and solids were analyzed by X-ray powder diffraction. The solids were composed of Form A.

Table 1

Diffraction Peaks Obtained from XRPD Analysis of Crystalline Form A

TABLE 1

| Diffraction Peaks Obtained from XRPD Analysis of Crystalline Form A Crystalline Form A Angle/2θ |
| --- |
| 5.8 |
| 7.1 |
| 8.6* |
| 11.7 |
| 12.3 |
| 13.0 |
| 14.2 |
| 14.6* |
| 16.0 |
| 16.9* |
| 17.2 |
| 17.6 |
| 17.9 |
| 18.1 |
| 18.3* |
| 19.4 |
| 19.9 |
| 20.4 |
| 20.7 |
| 21.2 |
| 21.4 |
| 21.8 |
| 22.7 |
| 23.0 |
| 23.5 |
| 23.9 |
| 24.9 |
| 25.5 |
| 26.2 |
| 26.4 |
| 27.2 |
| 28.0 |
| 28.2 |
| 29.6 |

Example 2

Example 2A: Preparation of Crystalline Form B of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (20 mg±1 mg) was weighed into an HPLC vial. Isopropanol (200 µl) was added at 50° C. and the solution that formed was cooled to 5° C. at 0.5° C./min. Solids formed after cooling were analyzed by XRPD and were consistent with partially crystalline Form B.

Example 2B: First Additional Preparation of Crystalline Form B of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile A 700 mg, f 1 mg amount of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile was weighed into a HPLC vial and a solvent of 10% $H_2O$ in IPA (5 vol, 3.5 ml) was added at 50° C. The sample was cooled to 5° C. at 0.5° C./min. The sample formed a thin grey suspension when the temperature reached 30° C. and was seeded using a 38 day old crystal preparation to assist formation of Form B and cooling continued. At 5° C. the sample had formed a thick white suspension and XRPD analysis showed partially crystalline pattern. The sample was seeded again to further enhance crystal formation and left to stir at 5° C. for 48 h. The resulting suspension comprised crystalline Form B. Sample was dried for 2 h in a vacuum oven.

Example 2C: Second Additional Preparation of Crystalline Form B of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (90.00 g) was dissolved in isopropanol/water (75/25 v/v) (347 ml) at −70° C. in a 2 L reactor. The solution was cooled to 40° C. over 30 minutes. A seed slurry was prepared in a separate vial by stirring 1.0 g of Form B in isopropanol/water (75/25 v/v) (10 ml) for ~1 hour. After the solution in the 2 L reactor reached 40° C., the seed slurry was sonicated for ~1 minute and then added to the solution in the 2 L reactor. The slurry was held for 1 hour at 40° C. and then cooled to 5° C. over 10 hours. After holding at 5° C. for 2 days, solids were collected by vacuum filtration. The reactor was washed with isopropanol/water (60/40 v/v) (~400 ml) and then the wash was collected and filtered with the wet cake. The wet cake was then washed two times with isopropanol/water (60/40 v/v) (~300 ml). Solids were collected and vacuum dried at ambient temperature for 3 days. The solids were analyzed by X-ray powder diffraction and were composed of Form B.

Example 2D: Third Additional Preparation of Crystalline Form B of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (36.89 g) was dissolved in isopropanol/heptane (80/20 v/v) (370 ml) at 60° C. in a 500 ml reactor. The solution was cooled to 45° C. over 15 minutes. A seed slurry was prepared in a separate vial by combining 559.9 mg of Form B in isopropanol/heptane (80/20 v/v) (6.5 ml). The seed slurry was sonicated for ~2 minutes then stirred at ambient temperature for ~1 hour. After the solution in the 500 ml reactor reached 40° C., the seed slurry was sonicated for 2 minutes and then added to the solution in the 500 ml reactor. The slurry was held for 2 hours at 45° C., cooled to 30° C. over 4 hours, held for 4 hours at 30° C., cooled to 20° C. over 3 hours and finally held at 20° C. for 8 hours. Solids were collected by vacuum filtration. The wet cake was washed two times with isopropanol/heptane (80/20 v/v) (110 ml). Solids were collected and vacuum dried at 30-40° C. for 1 day. The solids were analyzed by X-ray powder diffraction and were composed of Form B. The X-ray powder diffraction pattern for crystalline Form B made according to Example 2D is shown in FIG. 5A, and observed peaks are listed in Table 2. Characteristic peaks are marked with an asterisk.

Example 2E: Fourth Additional Preparation of Crystalline Form B of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (1386 mg) was weighed into a 20 ml vial and 30% water:IPA (5 vol) pre-mixed solvent was added at 50° C. The sample was cooled to 25° C. at 0.5° C. per min and seeded with 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, Form B approx. 2 mg. The sample was then cooled to 5° C. at 0.5° C./min and stirred at 5° C. overnight. In the morning the sample had formed a thick slurry and was left to stir at 5° C. over the weekend. The sample was filtered by Buchner filtration and then dried in a vacuum oven at room temperature for approx. 4 hours. XRPD analysis showed 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form B. Yield: 1.1 g, 79%. Characteristic peaks of Form B made according to Example 2E are marked with an asterisk.

Example 2F: Fifth Additional Preparation of Crystalline Form B of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (15 g) was dissolved in isopropanol/heptane (80/20 v/v) (150 ml) at 60° C. in a 250 mL reactor. The solution was cooled to 45° C. at an approximate rate of approximately 10° C./h. A seed slurry was prepared by combining 225 mg of Form B in 1.5 mL isopropanol/heptane (80/20 v/v). After the solution in the 250 ml reactor reached 45° C., the seed slurry was added to the 250 ml reactor and the slurry was stirred for 1 hour at 45° C., then cooled to 35° C. at a rate of 2.5° C./h, held for 4 hours at 35° C., cooled to 25° C. at a rate of 2.5° C./h, held for 4 hours at 25° C., cooled to 5° C. at a rate of 2.5° C./h, held at 5° C. for at least 8 hours. Solids were collected by vacuum filtration and dried under N2 sweep 1~2 h and vacuum drying. The solids were analyzed by X-ray powder diffraction after drying and were composed of Form B. Form B was obtained with 94.0% yield.

Figure 28:
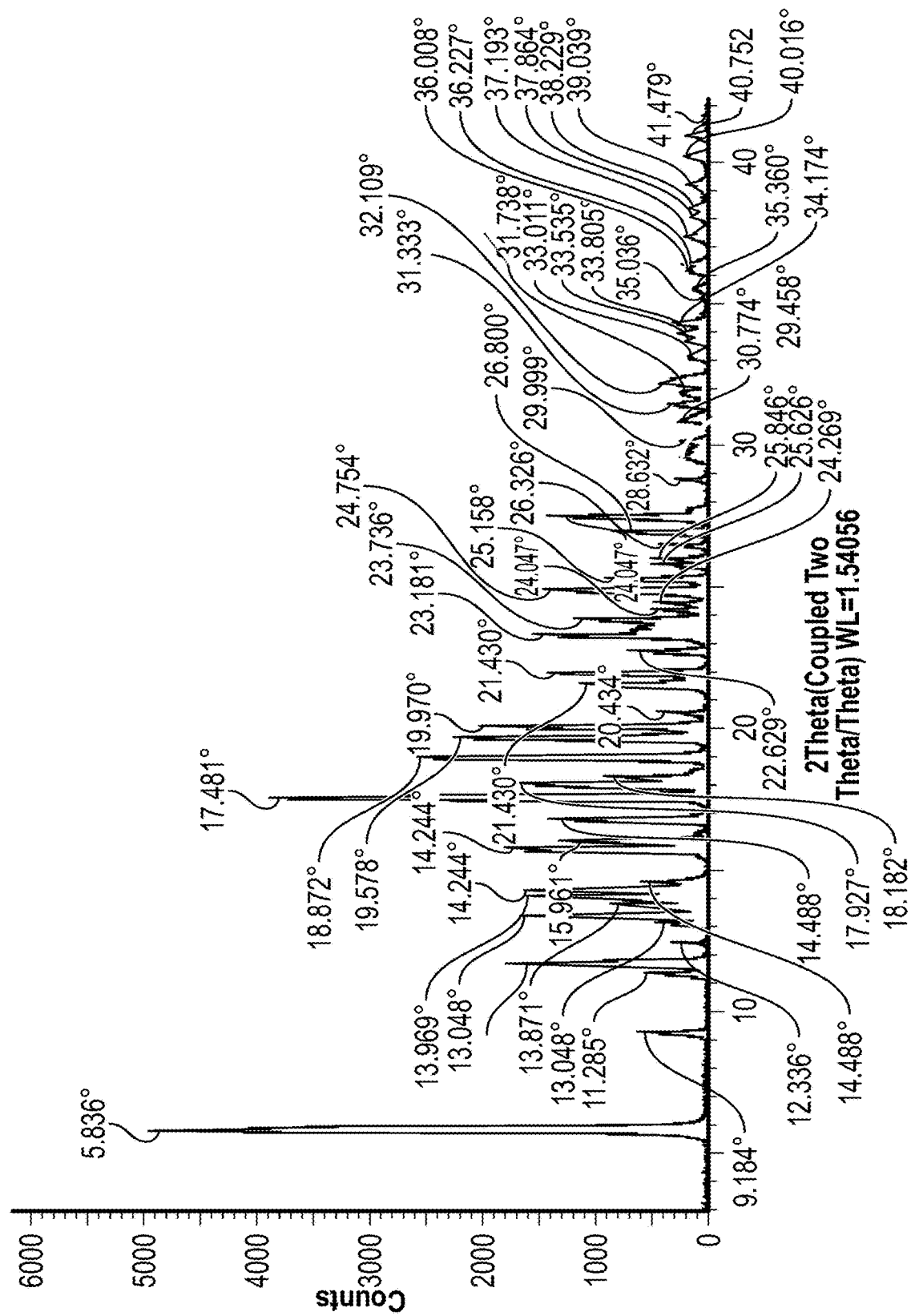
FIG. 28 displays an XRPD pattern of crystalline Form B prepared according to Example 2F.

FIG. 28 displays an XRPD pattern of crystalline Form B prepared according to Example 2F. The sample was examined using X-ray diffractometer (Bruker D8 Focus), scanned from 3° to 42° (2θ), at a step size 0.02° (2θ). The tube voltage and current were 40 kV and 40 mA, respectively. A subsample was placed onto a zero background XRPD-holder and slightly pressed to make the surface smooth for the analysis.

TABLE 2

| Diffraction Peaks Obtained from XRPD Analysis of Crystalline Form B Crystalline Form B Angle/2θ |
| --- |
| 5.8 |
| 9.1 |
| 11.2 |
| 11.6 |
| 12.3 |
| 13.0 |
| 13.3 |
| 13.6 |
| 13.9 |
| 14.2 |
| 14.5 |
| 15.3 |
| 15.6 |
| 15.9 |
| *16.7 |
| *17.5 |
| 17.9 |
| 18.1 |
| 18.4 |
| *18.8 |
| 19.5 |
| 19.9 |
| 20.4 |
| 21.4 |
| 21.8 |
| 22.6 |
| 23.1 |
| 23.4 |
| 23.5 |
| 23.7 |
| 24.0 |
| 24.3 |
| 24.7 |
| 25.1 |
| 25.6 |
| 25.8 |
| 26.3 |
| 26.7 |
| 27.3 |
| 27.6 |
| 28.6 |
| 29.4 |
| 29.7 |
| 30.0 |

Example 3

Preparation of Crystalline Form C of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (75.5 mg) was stirred in isopropanol/water (75/25 v/v) (1 ml) at ambient temperature for 14 days. Solids were collected by filtering the slurry through a syringe filter. Solids were analyzed by X-ray powder diffraction and were composed of Form C. The X-ray powder diffraction pattern for crystalline Form C is shown in FIG. 9, and observed peaks obtained from the XRPD analysis are listed in Table 3. Characteristic peaks are marked with an asterisk. As explained in Example 22 and FIG. 27, this is a hydrated form.

was added to the resulting mixture of powdered and glassy solids. The mixture was then stirred at ambient temperature for 1 day. Solids were collected by vacuum filtration and were analyzed by X-ray powder diffraction. The solids were composed of Form D. The X-ray powder diffraction pattern for crystalline Form D is shown in FIG. 13, and observed peaks obtained from the XRPD analysis are listed in Table 4. Characteristic peaks marked with an asterisk. Physical characterization data and experimentation indicate that Form D is a hydrate.

TABLE 3

Diffraction Peaks Obtained
from XRPD Analysis
of Crystalline Form C
Crystalline Form C
Angle/2θ

| |
|---|
| 5.7 |
| 9.0 |
| 11.0 |
| 11.3 |
| 12.3 |
| 13.3 |
| 13.9 |
| 14.2 |
| 15.1 |
| 15.5 |
| 15.8 |
| *16.4 |
| 17.1 |
| 17.3 |
| 17.8 |
| 18.0 |
| 18.4 |
| 18.6 |
| 19.3 |
| *19.7 |
| 21.1 |
| 21.5 |
| 21.8 |
| 22.1 |
| 22.8 |
| 23.1 |
| 23.2 |
| 23.6 |
| 23.7 |
| 24.4 |
| 24.7 |
| 25.2 |
| 26.3 |
| 26.7 |
| 27.2 |
| 28.1 |
| 29.0 |
| 29.4 |
| 29.8 |

TABLE 4

Diffraction Peaks Obtained
from XRPD Analysis
of Crystalline Form D
Crystalline Form D
Angle/2θ

| |
|---|
| *4.4 |
| 8.9 |
| 10.0 |
| 11.2 |
| 12.3 |
| 12.7 |
| 13.4 |
| 13.6 |
| 13.8 |
| 14.3 |
| 15.2 |
| 16.1 |
| 16.3 |
| 16.9 |
| 17.7 |
| 18.0 |
| 18.6 |
| 19.2 |
| 20.1 |
| 20.9 |
| 21.2 |
| 21.8 |
| 22.6 |
| 23.0 |
| 23.5 |
| 24.2 |
| 24.7 |
| 25.2 |
| 26.1 |
| 26.3 |
| 27.2 |
| 27.6 |
| 27.9 |
| 28.3 |
| 29.0 |
| 29.2 |

Example 4

Preparation of Crystalline Form D of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (332.8 mg) was dissolved in isopropanol (~100 ml) at ambient temperature. Approximately ⅓ of the solution was collected into a 100 ml round bottom flask, and then the solution was rotary evaporated at ~40° C. Water (~10 ml)

Example 5

Preparation of Crystalline Form E of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form D was placed in an uncapped vial which was then placed inside a larger jar containing phosphorus pentoxide. The larger jar was capped and solids were analyzed by X-ray powder diffraction after 2 to 4 days. The solids were composed of Form E. The X-ray powder diffraction pattern for crystalline Form E is shown in FIG. 15, and observed peaks and percent peak intensities obtained from the XRPD analysis are listed in Table 5. Characteristic peaks marked with an asterisk.

TABLE 5

Diffraction Peaks Obtained
from XRPD Analysis
of Crystalline Form E

| Crystalline Form E Angle/2θ |
| --- |
| *5.2 |
| 9.2 |
| *10.2 |
| 11.2 |
| 11.8 |
| 13.5 |
| 14.3 |
| 14.3 |
| 15.4 |
| 16.4 |
| 16.9 |
| 17.7 |
| 18.0 |
| 19.4 |
| 20.3 |
| 20.5 |
| 21.0 |
| 21.3 |
| 21.9 |
| 22.4 |
| 22.7 |
| 23.1 |
| 23.8 |
| 24.2 |
| 25.7 |
| 26.8 |
| 27.2 |
| 27.4 |
| 27.9 |
| 28.6 |
| 29.9 |

Example 6

Differential Scanning Calorimetry (DSC) Analysis of Crystalline Form A

DSC analysis of a sample of crystalline Form A made according to Example 1A was conducted using a TA Instruments Q2000 equipped with a 50-position auto-sampler per the manufacturer's instructions. A weighed amount of crystalline Form A was placed in a pin-holed aluminum pan, and heated using an underlying heating rate of 2° C./min and temperature modulation parameters of ±0.636° C. (amplitude) every 60 seconds (period) (FIG. 2) or heated at 10° C./min from 25° C. to 300° C. (FIG. 3). A purge of dry nitrogen at 50 ml/min was maintained over the sample. The instrument control software used was Advantage for Q Series and Thermal Advantage and the data were analyzed using Universal Analysis. The DSC thermogram profile of crystalline Form A made according to Example 1A is shown in FIG. 2. As shown in FIG. 2, crystalline Form A has endothermic peak onset at about 107° C. with a heat of fusion of 46 J/g.

The DSC thermogram profile of crystalline Form A made according to Example 1B, generated using a procedure similar to that which is described above, is shown in FIG. 11. As shown in FIG. 11, crystalline Form A has endothermic peak onset at about 119° C. with a heat of fusion of 58 J/g.

Example 7

Thermo-Gravimetric Analysis (TGA) of Crystalline Form A

TGA analysis was conducted using a TA Instruments Q500 TGA, equipped with a 16-position auto-sampler. A weighed sample was loaded onto a pre-tared aluminium DSC pan and heated at 10° C./min from ambient temperature to 350° C. A nitrogen purge at 60 ml/min was maintained over the sample. The instrument control software employed for the analysis was Advantage for Q Series and Thermal Advantage and the data were analyzed using Universal Analysis.

The TGA thermogram profile of crystalline Form A is shown in FIG. 3. A shown in FIG. 3, having negligible weight loss below the onset of degradation at 200° C. as measured by TGA.

Example 8

Dynamic Vapor Sorption (DVS) Analysis of Crystalline Form A

Sorption isotherms of crystalline Form A were obtained using a SMS GVS Intrinsic moisture sorption analyzer, controlled by GVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change (mass relaxation) of the sample as a function of % RH was constantly monitored by a microbalance (accuracy ±0.005 mg).

Briefly, a 33 day dried sample of crystalline Form A was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. A double cycle (4 scans) was carried out. Data analysis was carried out within Microsoft Excel using the DVS Analysis Suite.

DVS isotherm profile of crystalline Form A is shown in FIG. 4. As shown in FIG. 4, Form A is characterized by having an observed weight gain from about 0.1% at 40% RH to 0.6% at 90% RH, fully lost upon desorption to 0% RH.

Example 9

DSC Analysis of Crystalline Form B

DSC analysis of a 50 sample of crystalline Form B was conducted using a TA Instruments Q2000 equipped with a 50-position auto-sampler per the manufacturer's instructions. Briefly, 1.661 mg of a sample of crystalline Form B was placed in a pin-holed aluminium pan, and heated using an underlying heating rate of 2° C./min and temperature modulation parameters of 0.636° C. (amplitude) every 60 seconds (period) from 25° C. to 330° C. A purge of dry nitrogen at 50 ml/min was maintained over the sample. The instrument control software used was Advantage for Q Series and Thermal Advantage and the data were analyzed using Universal Analysis.

The DSC thermogram profile of a sample of crystalline Form B is shown in FIG. 6. As shown in FIG. 6, crystalline Form B is characterized by having an endothermic peak onset at about 109° C. with a heat of fusion of 49 J/g.

Figure 12:
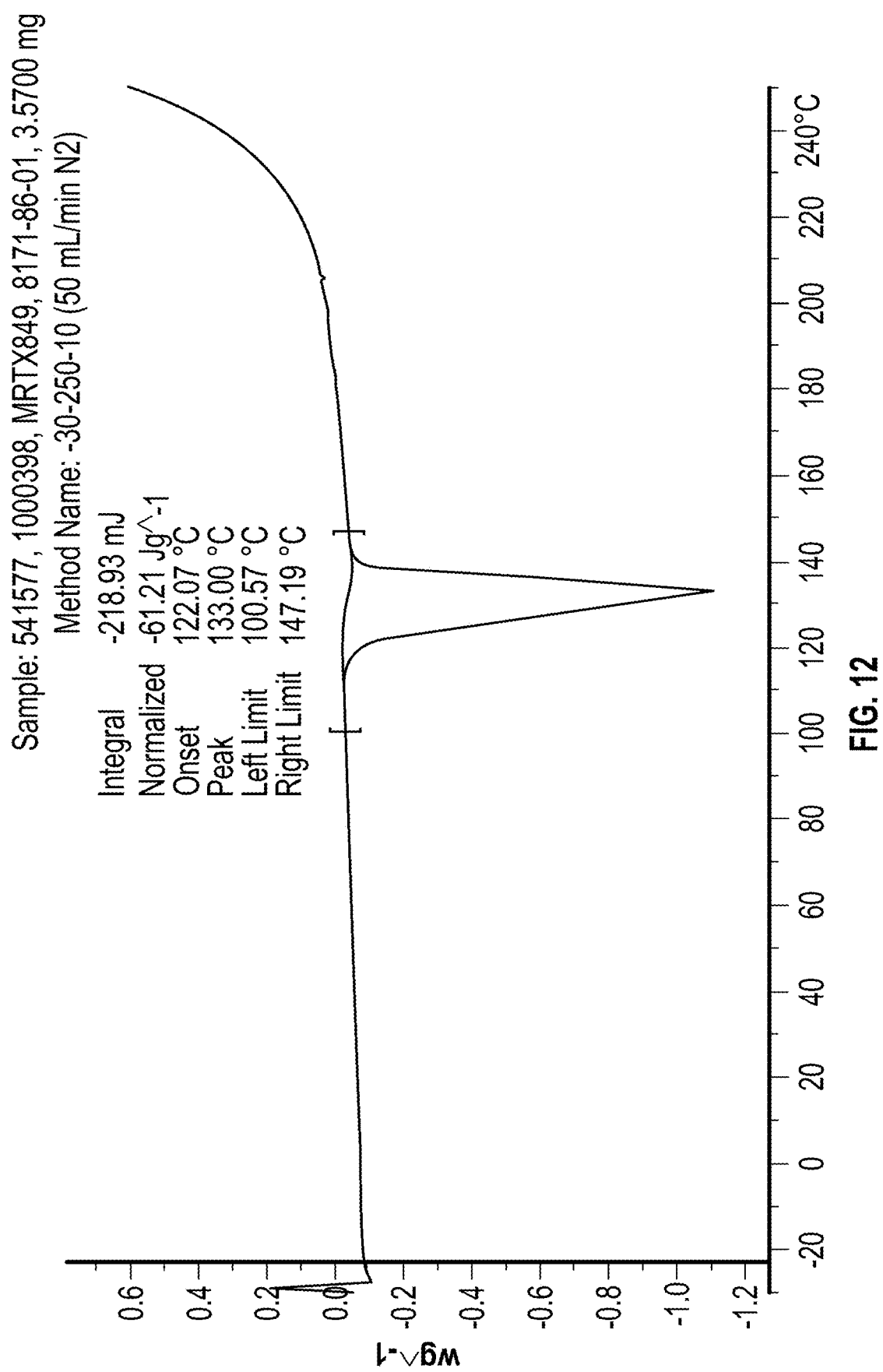
FIG. 12 illustrates a DSC profile of crystalline Form B prepared according to Example 2C.

A second DSC thermogram profile of a sample of crystalline Form B is shown in FIG. 12. As shown in FIG. 12, crystalline Form B is characterized by having an endothermic peak onset at about 122° C. with a heat of fusion of 61 J/g.

Figure 22:
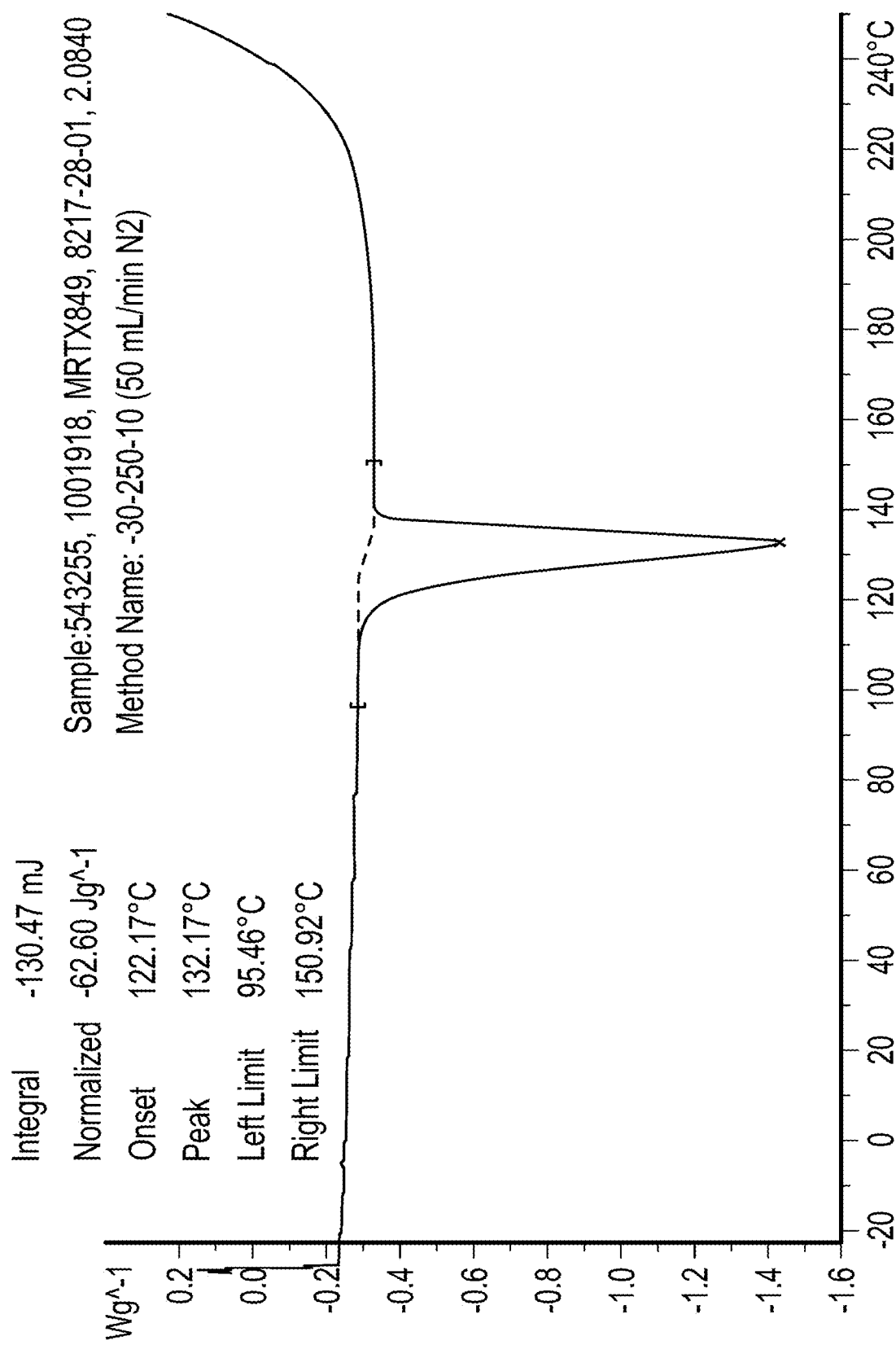
FIG. 22 illustrates a DSC profile of crystalline Form B prepared according to Example 2D.

A third DSC thermogram profile of a sample of crystalline Form B is shown in FIG. 22. As shown in FIG. 22, crystalline Form B is characterized by having an endothermic peak onset at about 112° C. with a heat of fusion of 62 J/g.

Example 10

TGA of Crystalline Form B

TGA analysis was conducted using a TA Instruments Q500 TGA, equipped with a 16-position auto-sampler. Briefly, a sample of crystalline Form B was loaded onto a pre-tared aluminium DSC pan and heated at 10° C./min from ambient temperature to 350° C. A nitrogen purge at 60 ml/min was maintained over the sample. The instrument control software employed for the analysis was Advantage for Q Series and Thermal Advantage and the data were analyzed using Universal Analysis.

The TGA thermogram profile of crystalline Form B is shown in FIG. 7. A shown in FIG. 7, crystalline Form B is characterized by having a negligible weight loss of mass up to about 111° C. until the onset of degradation at about 250° C.+

Example 11

DVS Analysis of Crystalline Form B

Sorption isotherms of crystalline Form B were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Briefly, a sample of crystalline Form B was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. A double cycle (4 scans) was carried out. Data analysis was carried out within Microsoft Excel using the DVS Analysis Suite.

DVS isotherm profile of crystalline Form B is shown in FIG. 8. As shown in FIG. 8, crystalline Form B is characterized by having from about 0.6% at 60% RH to 2.9% at 70% RH, further increasing to 2.5% at 90% RH. Following a weight loss to 2.2% from 90% RH to 70% RH, a rapid weight loss is observed from 70 to 50% RH with a weight change from 2.2% to 0.4%. Constant gentle decrease in weight to 0% from 50 to 0% RH is observed. Cycles repeat showing little hysteresis.

Example 12

DSC Analysis of Crystalline Form C

Differential scanning calorimetry was performed using a Mettler-Toledo DSC3+ differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, and the weight was accurately recorded. The pan lid was pierced then inserted into the DSC cell. A weighed aluminum pan configured as the sample pan was placed on the reference side of the cell. The pan lid was pierced prior to sample analysis. Data was collected from 25° C. to 350° C. at 10° C./min.

The DSC thermogram profile of a sample of crystalline Form C is shown in FIG. 10. As shown in FIG. 10, crystalline Form C is characterized by having a small endothermic peak onset about 58° C. and a strong endothermic peak onset at about 118° C.

Example 13

TGA of Crystalline Form C

TG analysis was performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was hermetically sealed, the lid pierced, then inserted into the TG furnace. A weighed aluminum pan configured as the sample pan was placed on the reference platform. The furnace was heated under nitrogen. Data was collected from 25° C. to 350° C. at 10° C./min.

The TGA thermogram profile of crystalline Form C is shown in FIG. 10. A shown in FIG. 10, crystalline Form C is characterized by having a stepwise loss of mass of 1.2% from about 45° C. to about 86° C. until the onset of degradation at about 260° C.

Example 14

DVS Analysis of Crystalline Form C

Sorption isotherms of crystalline Form C are obtained using a SMS DVS Intrinsic moisture sorption analyzer, controlled by DVS Intrinsic Control software. The sample temperature is maintained at 25° C. by the instrument controls. The humidity is controlled by mixing streams of dry and wet nitrogen, with a total flow rate of 200 ml/min. The relative humidity is measured by a calibrated Rotronic probe (dynamic range of 1.0-100% RH), located near the sample. The weight change, (mass relaxation) of the sample as a function of % RH is constantly monitored by a microbalance (accuracy ±0.005 mg).

Briefly, a sample of crystalline Form C is placed in a tared mesh stainless steel basket under ambient conditions. The sample is loaded and unloaded at 40% RH and 25° C. (typical room conditions). A moisture sorption isotherm is performed as outlined below (2 scans per complete cycle). The standard isotherm is performed at 25° C. at 10% RH intervals over a 0-90% RH range. A double cycle (4 scans)

is carried out. Data analysis is carried out within Microsoft Excel using the DVS Analysis Suite.

Example 15

DSC Analysis of Crystalline Form D

Differential scanning calorimetry was performed using a Mettler-Toledo DSC3+ differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, and the weight was accurately recorded. The pan lid was pierced then inserted into the DSC cell. A weighed aluminum pan configured as the sample pan was placed on the reference side of the cell. The pan lid was pierced prior to sample analysis. Data was collected from 25° C. to 350° C. at 10° C./min.

The DSC thermogram profile of a sample of crystalline Form D is shown in FIG. 14. As shown in FIG. 14, crystalline Form D is characterized by having a broad endothermic peak with a maximum at about 84° C. and another endothermic peak with a peak with a maximum at about 110° C.

Example 16

TGA of Crystalline Form D

TG analysis was performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was hermetically sealed, the lid pierced, then inserted into the TG furnace. A weighed aluminum pan configured as the sample pan was placed on the reference platform. The furnace was heated under nitrogen. Data was collected from 25° C. to 350° C. at 10° C./min.

The TGA thermogram profile of crystalline Form D is shown in FIG. 14. A shown in FIG. 14, crystalline Form D is characterized by having a stepwise loss of mass of 4.3% from about 45° C. to about 116° C. until the onset of degradation at about 260° C.

Example 17

DVS Analysis of Crystalline Form D

Sorption isotherms of crystalline Form D are obtained using a SMS DVS Intrinsic moisture sorption analyzer, controlled by DVS Intrinsic Control software. The sample temperature is maintained at 25° C. by the instrument controls. The humidity is controlled by mixing streams of dry and wet nitrogen, with a total flow rate of 200 ml/min. The relative humidity is measured by a calibrated Rotronic probe (dynamic range of 1.0-100% RH), located near the sample. The weight change, (mass relaxation) of the sample as a function of % RH is constantly monitored by a microbalance (accuracy ±0.005 mg).

Briefly, a 50 day dried sample of crystalline Form D is placed in a tared mesh stainless steel basket under ambient conditions. The sample is loaded and unloaded at 40% RH and 25° C. (typical room conditions). A moisture sorption isotherm is performed as outlined below (2 scans per complete cycle). The standard isotherm is performed at 25° C. at 10% RH intervals over a 0-90% RH range. A double cycle (4 scans) is carried out. Data analysis is carried out within Microsoft Excel using the DVS Analysis Suite.

Example 18

DSC Analysis of Crystalline Form E

Differential scanning calorimetry was performed using a Mettler-Toledo DSC3+ differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, and the weight was accurately recorded. The pan lid was pierced then inserted into the DSC cell. A weighed aluminum pan configured as the sample pan was placed on the reference side of the cell. The pan lid was pierced prior to sample analysis. Data was collected from 25° C. to 350° C. at 10° C./min.

The DSC thermogram profile of a sample of crystalline Form E is shown in FIG. 16. As shown in FIG. 16, crystalline Form E by having an endothermic peak onset at about 99° C. and a heat of fusion of 47 J/g.

Example 19

TGA of Crystalline Form E

TG analysis was performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was hermetically sealed, the lid pierced, then inserted into the TG furnace. A weighed aluminum pan configured as the sample pan was placed on the reference platform. The furnace was heated under nitrogen. Data was collected from 25° C. to 350° C. at 10° C./min.

The TGA thermogram profile of crystalline Form E is shown in FIG. 17. A shown in FIG. 17, there was a negligible loss of mass up to about 94° C. and through the onset of degradation at about 240° C.

Example 20

DVS Analysis of Crystalline Form E

Vapor sorption data were collected on a Surface Measurement System DVS Intrinsic instrument. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours.

DVS isotherm profile of crystalline Form E is shown in FIG. 18. As shown in FIG. 18, by having a gradual weight gain of 1.2% between 5% to 96% RH. During desorption, the weight gained was lost with some hysteresis.

Example 21

Single Crystals of Form A and Form B

Figure 23:
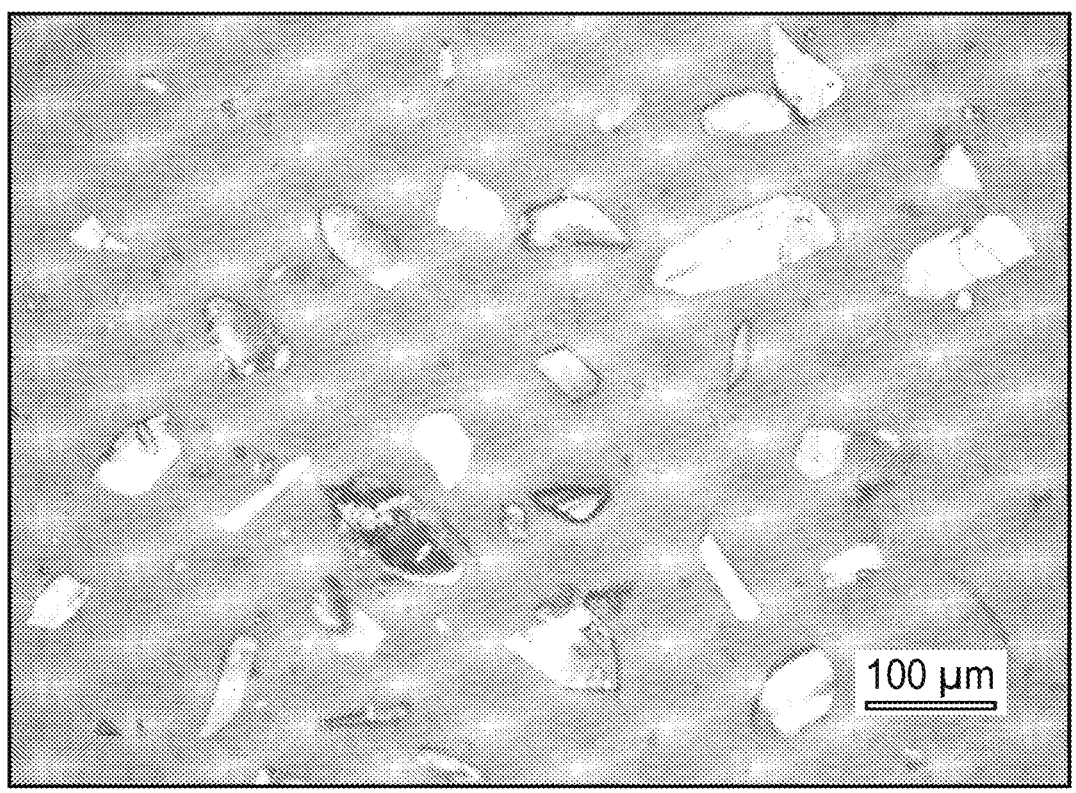
FIG. 23 is a PLM image of crystals of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile grown from isopropanol-heptane at 40° C. A plate-like crystal was used for structure determination of Form B, and a small needle-like crystal was used for structure determination of Form A.

Crystallization of the amorphous starting material (98% purity, as labelled) in isopropanol-heptane at 40° C. afforded crystals suitable for single-crystals X-ray analysis. The crystals displayed two distinguishable morphologies, plate and needle (FIG. 23). The crystal structure solved from a small needle was found to be a neat form of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile. The absolute configuration of the molecule was confirmed to be (S, S). The structure of a plate crystal was also solved and appeared to be neat as well based on difference electron density maps. Both structures were solved under ambient conditions. The structures were designated as Form A and Form B as shown in Table 6 below:

2-enoyl)piperazin-2-yl]acetonitrile. The final anisotropic full-matrix least-squares refinement on F2 with 389 variables converged at R1=7.75%, for the observed data and wR2=27.68% for all data. The goodness-of-fit was 0.970. The largest peak in the final difference electron density synthesis was 0.209 e-/Å3 and the largest hole was −0.214 e-/Å3 with an RMS deviation of 0.050 e-/Å3. On the basis of the final model, the calculated density was 1.295 g/cm3 and F(000), 636 e-.

Crystallographic Results of Form B: Bruker D8 QUEST Single-crystal X-ray Diffractometer, equipped with high brightness IµS 3.0 microfocus (50 kV×1 mA) for Cu radiation ($\lambda$=1.54178 Å) and with PHOTON II Charge-Integrat-

TABLE 6

| Crystal Form | T(K) | a (Å) | b(Å) | c(Å) | $\alpha(°)$ | $\beta(°)$ | $\gamma(°)$ | V(Å$^3$) | SP | Z' |
|---|---|---|---|---|---|---|---|---|---|---|
| Form A | Ambient | 12.534(4) | 8.129(2) | 15.321(5) | 90 | 97.11(2) | 90 | 1549.0(8) | P2$_1$ | 1 |
| Form B | Ambient | 8.1446(2) | 12.4829(4) | 30.4933(11) | 90 | 90 | 90 | 3101.44(17) | P2$_1$2$_1$2$_1$ | 1 |

Figure 24:
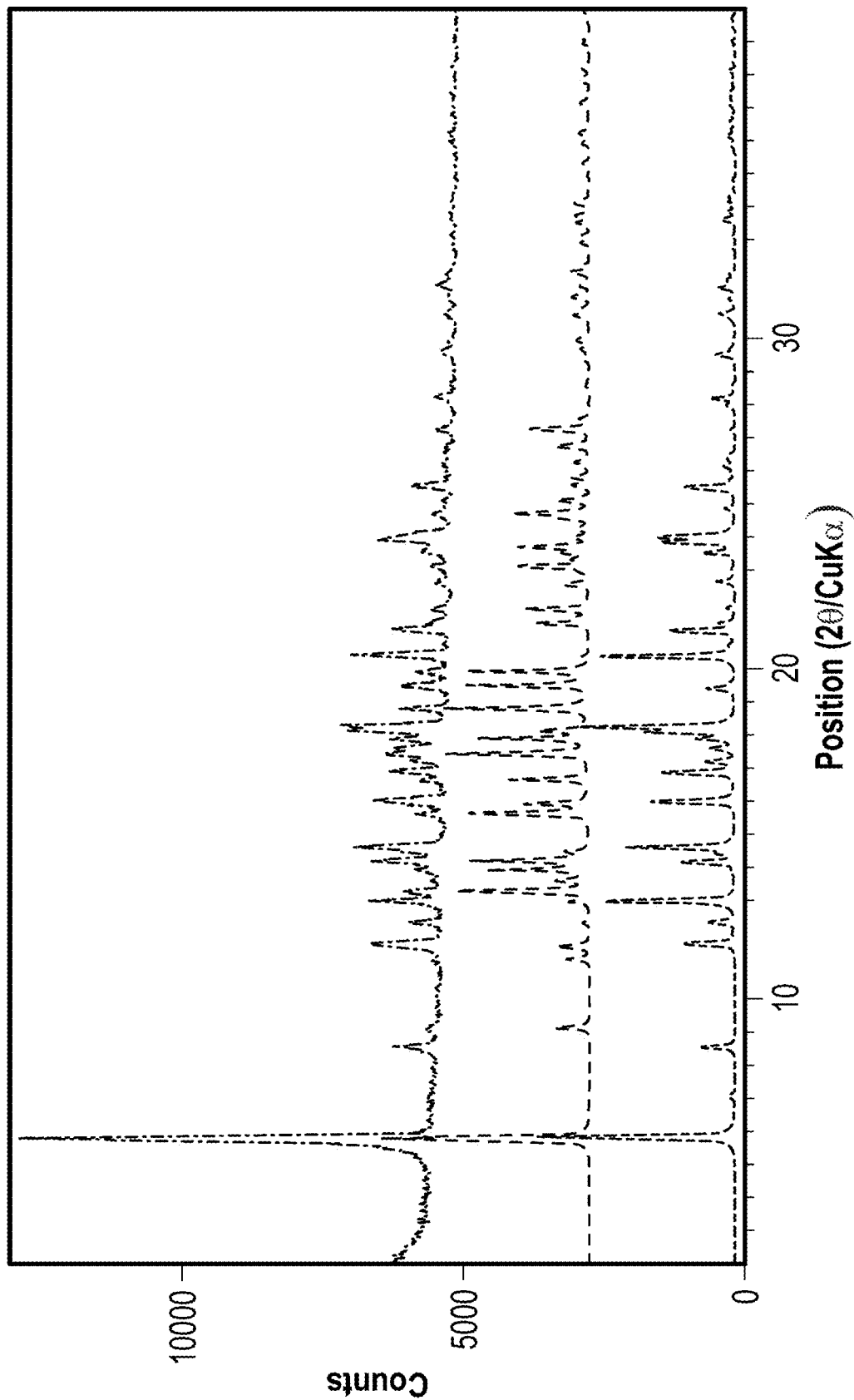
FIG. 24 is an overlay of simulated XRPD patterns of Form A (bottom), Form B simulated (b), and bulk of the starting material (c), showing the bulk was a mixture of Form A and Form B2.
Figure 25:
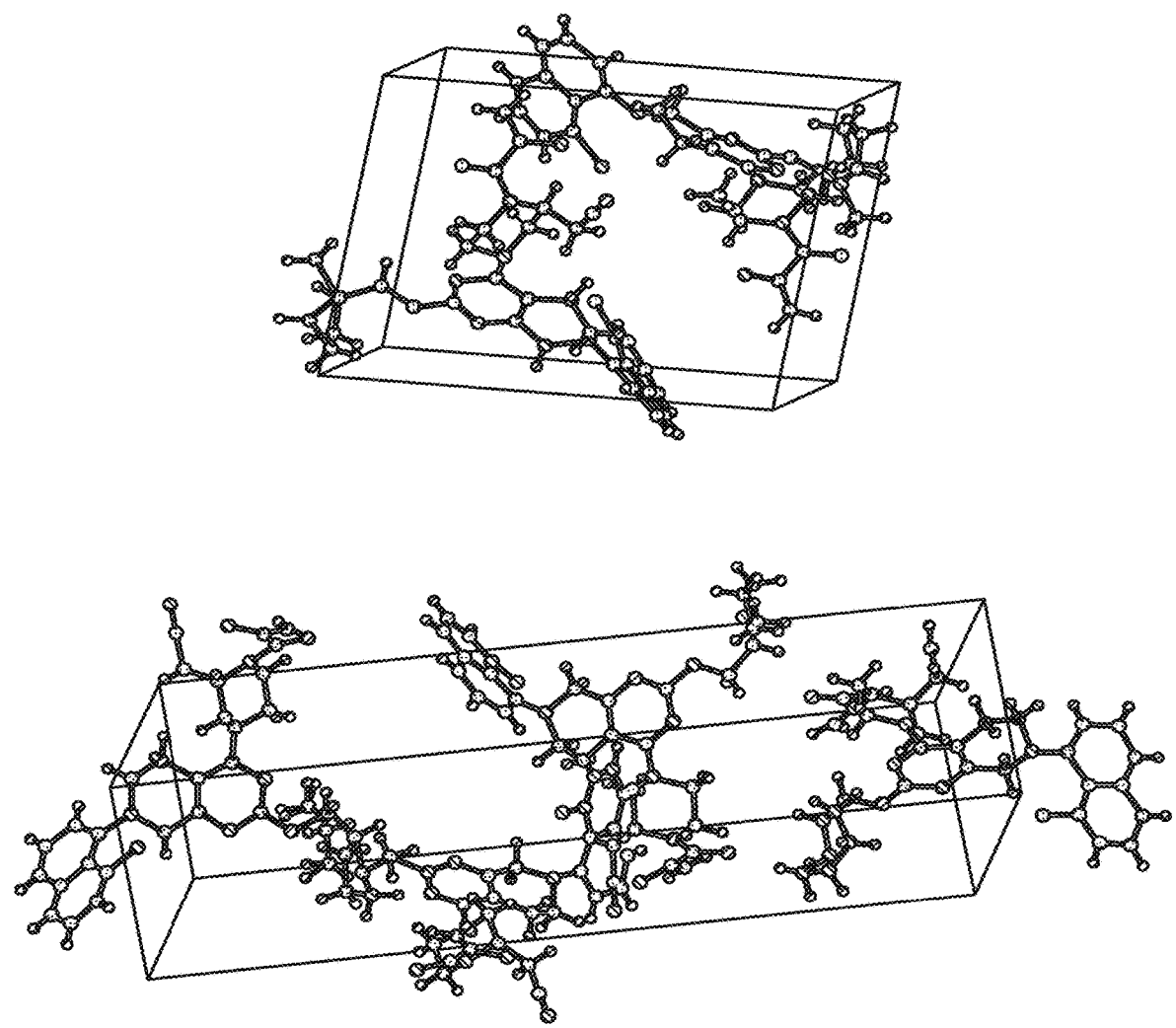
FIG. 25 depicts the unit cell shape and structure of content in the crystal structure of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form A containing two molecules (top), and in Form B containing four molecules (bottom).

With simulated patterns generated from the crystal structures, the crystalline bulk crystal (needle and plate, FIG. 23) was found to be a mixture of Form A and Form B (FIG. 24). Crystallographic data showed 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile displayed essentially identical solid-state conformation in Form A and Form B although crystal packing in the two structures differed (FIG. 25).

Crystallographic Results of Form A: Bruker D8 QUEST Single-crystal X-ray Diffractometer, equipped with high brightness IµS 3.0 microfocus (50 kV×1 mA) for Cu radiation ($\lambda$=1.54178 Å) and with PHOTON II Charge-Integrating Pixel Array Detector of superior speed, sensitivity, and accuracy, was used for screening/evaluation of crystals and for diffraction data collection. Bruker APEX3 software suite including SHELXTL was used for diffraction experiments including data collection and integration, and for solving, refining, displaying and publishing of structural results. A clear colorless needle-like specimen of approximate dimensions 0.005 mm×0.010 mm×0.060 mm was used for the X-ray crystallographic analysis. The X-ray intensity data were measured ($\lambda$=1.54178 Å) under ambient conditions. A total of 1458 frames were collected. The total exposure time was 11.58 hours. The frames were integrated with the Bruker SAINT software package using a narrow-frame algorithm. The integration of the data using a monoclinic unit cell yielded a total of 18743 reflections to a maximum θ angle of 63.01° (0.87 Å resolution), of which 4014 were independent (average redundancy 4.669, completeness=89.2%, Rint=15.90%, Rsig=19.44%) and 1527 (38.04%) were greater than 2σ(F2). The final cell constants of a=12.534(4) Å, b=8.129(2) Å, c=15.321(5) Å, β=97.11(2)°, volume=1549.0(8) Å3, are based upon the refinement of the XYZ-centroids of 2346 reflections above 20 σ(I) with 5.813°<2θ<122.7°. Data were corrected for absorption effects using the Multi-Scan method (SADABS). The ratio of minimum to maximum apparent transmission was 0.859. The calculated minimum and maximum transmission coefficients (based on crystal size) are 0.9160 and 0.9930. The structure was solved and refined using the Bruker SHELXTL Software Package, using the space group P 1 21 1, with Z=2 for the formula unit, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroproping Pixel Array Detector of superior speed, sensitivity, and accuracy, was used for screening/evaluation of crystals and for diffraction data collection. Bruker APEX3 software suite including SHELXTL was used for diffraction experiments including data collection and integration, and for solving, refining, displaying and publishing of structural results. A clear colorless thin plate-like specimen of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, approximate dimensions 0.010 mm×0.080 mm×0.080 mm, was used for the X-ray crystallographic analysis. The X-ray intensity data were measured ($\lambda$=1.54178 Å) under ambient conditions. A total of 1302 frames were collected. The total exposure time was 9.97 hours. The frames were integrated with the Bruker SAINT software package using a narrow-frame algorithm. The integration of the data using an orthorhombic unit cell yielded a total of 42682 reflections to a maximum θ angle of 69.720 (0.82 Å resolution), of which 4612 were independent (average redundancy 9.255, completeness=83.0%, Rint=9.55%, Rsig=6.39%) and 2745 (59.52%) were greater than 2σ(F2). The final cell constants of a=8.1446(2) Å, b=12.4879(4) Å, c=30.4933(11) Å, volume=3101.44(17) Å3, are based upon the refinement of the XYZ-centroids of 9150 reflections above 20 σ(I) with 5.796°<2θ<137.8°. Data were corrected for absorption effects using the Multi-Scan method (SADABS). The ratio of minimum to maximum apparent transmission was 0.854. The calculated minimum and maximum transmission coefficients (based on crystal size) are 0.8910 and 0.9850. The structure was solved and refined using the Bruker SHELXTL Software Package, using the space group P 21 21 21, with Z=4 for the formula unit, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile. The final anisotropic full-matrix least-squares refinement on F2 with 389 variables converged at R1=8.53%, for the observed data and wR2=21.83% for all data. The goodness-of-fit was 1.182. The largest peak in the final difference electron density synthesis was 0.195 e-/Å3 and the largest hole was −0.251 e-/Å3 with an RMS deviation of 0.052 e-/Å3. On the basis of the final model, the calculated density was 1.294 g/cm3 and F(000), 1272 e-.

Example 22

Single Crystals of Form B and Form C

Figure 26:
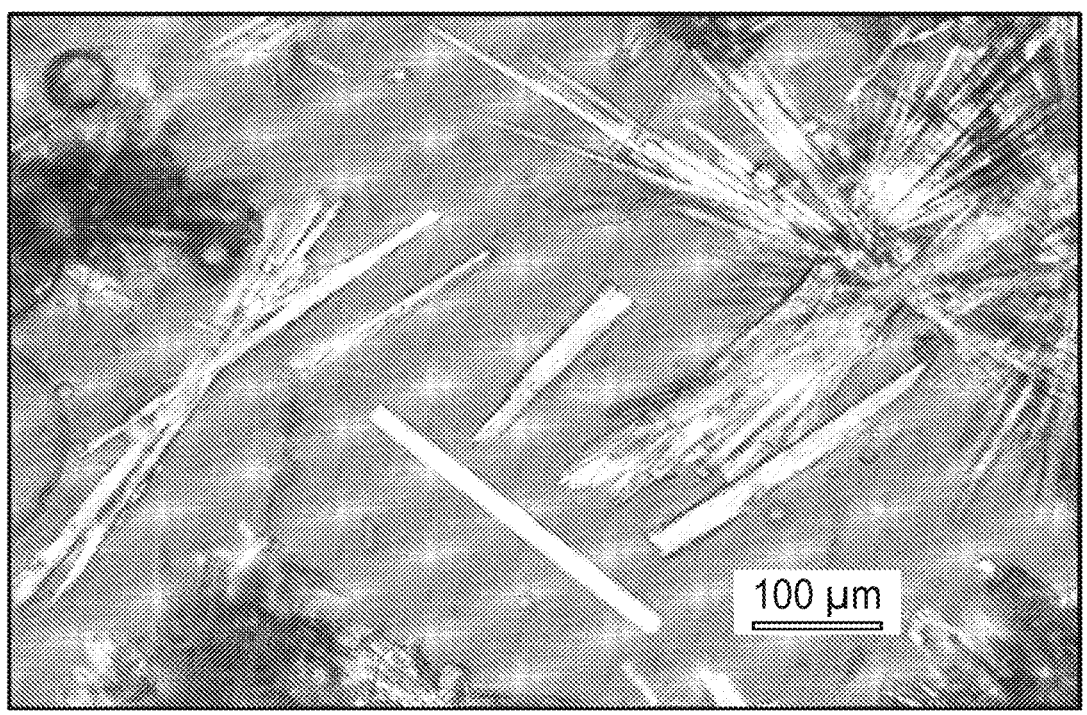
FIG. 26 is a PLM image of crystals of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile grown from isopropanol-water. The structure was determined to be Form C.

Recrystallization of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile from isopropanol-water at RT afforded needle/blade-like crystals (FIG. 26) suitable for single-crystals X-ray analysis. A needle crystal was freshly isolated from mother liquor and immediately cooled at 223K on the single-crystal X-ray diffractometer equipped with a LT device. The crystal structure solved from the data was a monohydrate of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, and its simulated pattern matched Form C. A second dataset was then collected on the same needle crystal at 293K. The structure solved was completely dehydrated and matched previously solved structure of Form B.

Figure 27:
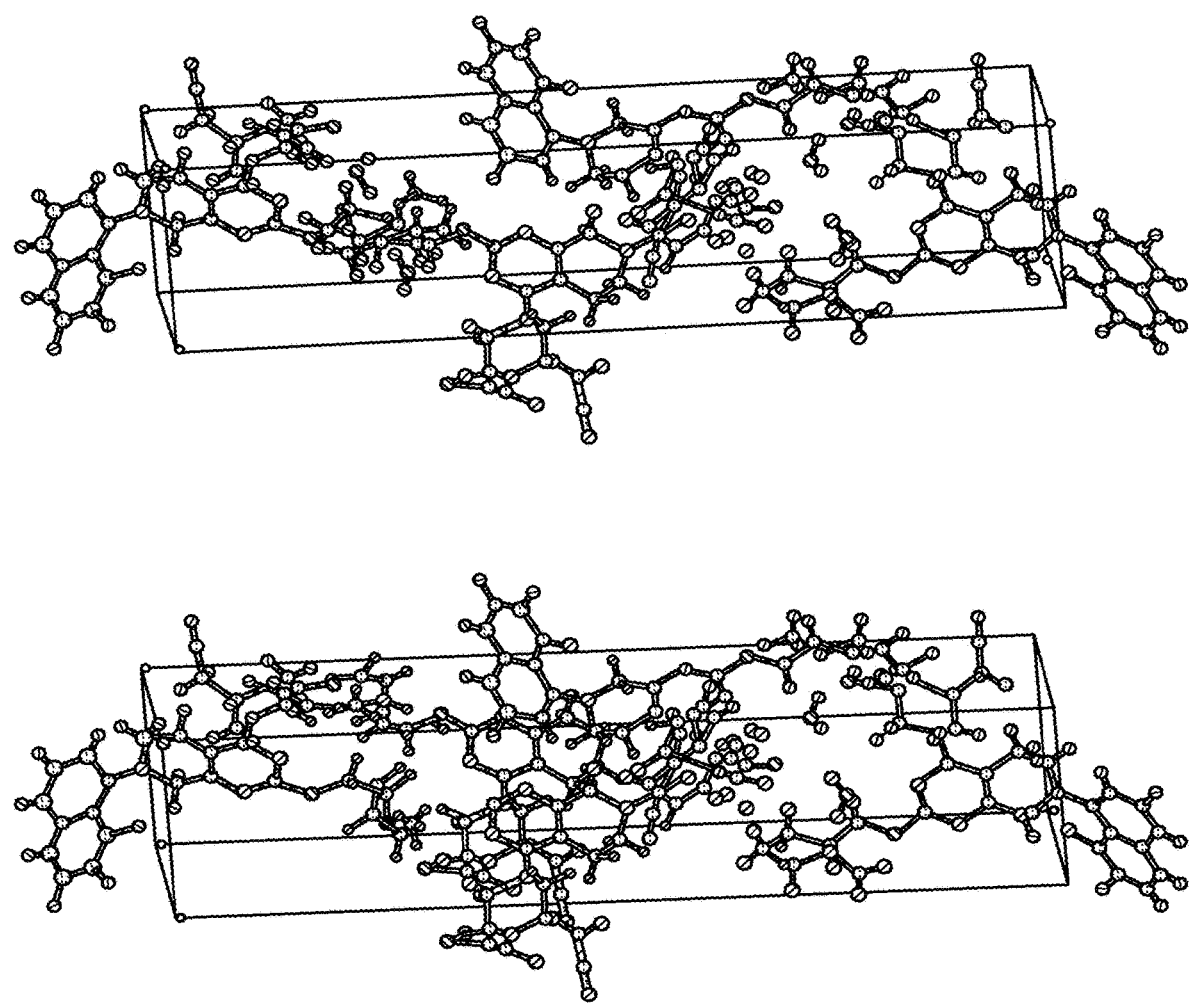
FIG. 27 depicts the unit cell shape and structure of content in the crystal structure of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile Form C (top), and Form B (bottom).

Form C and Form B are isomorphous (FIG. 27). The water molecule in the monohydrate formed two hydrogen bonds, as H-bond donor, with the carbonyl oxygen and pyrrolidine nitrogen of −849 molecule. Departure of water from crystal lattice was accompanied by conformational change of −849 molecule, mainly a ~134° rotation of N-methylpyrrolidine group, as indicated by the torsion angle O—C—C—N, 68.550 in monohydrate and −65.31° in dehydrated structure.

Crystallographic Results of Form C (monohydrate): Bruker D8 QUEST Single-crystal X-ray Diffractometer, equipped with high brightness IμS 3.0 microfocus (50 kV×1 mA) for Cu radiation ($\lambda$=1.54178 Å) and with PHOTON II Charge-Integrating Pixel Array Detector of superior speed, sensitivity, and accuracy, was used for screening/evaluation of crystals and for diffraction data collection. Bruker APEX3 software suite including SHELXTL was used for diffraction experiments including data collection and integration, and for solving, refining, displaying and publishing of structural results. A Cryostream 800 PLUS low temperature device was used to slow down desolvation thus reduce damage of crystallinity. With the crystal in a cold nitrogen gas stream also reduce thermal motion of atoms and increases crystal's scattering power leading to better quality structures. A clear colorless needle-like specimen of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, approximate dimensions 0.060 mm×0.080 mm×0.120 mm, was used for the X-ray crystallographic analysis. The X-ray intensity data were measured ($\lambda$=1.54178 Å) at 223K. A total of 2926 frames were collected. The total exposure time was 16.26 hours. The frames were integrated with the Bruker SAINT software package using a narrow-frame algorithm. The integration of the data using an orthorhombic unit cell yielded a total of 54983 reflections to a maximum $\theta$ angle of 69.800 (0.82 Å resolution), of which 5912 were independent (average redundancy 9.300, completeness=99.4%, Rint=7.26%, Rsig=4.01%) and 4606 (77.91%) were greater than 2σ(F2). The final cell constants of a=8.0887(3) Å, b=12.6101(5) Å, c=30.9568(11) Å, volume=3157.6(2) Å3, are based upon the refinement of the XYZ-centroids of 9922 reflections above 20 σ(I) with 5.709°<2θ<135.1°. Data were corrected for absorption effects using the Multi-Scan method (SADABS). The ratio of minimum to maximum apparent transmission was 0.871. The calculated minimum and maximum transmission coefficients (based on crystal size) are 0.8410 and 0.9160. The structure was solved and refined using the Bruker SHELXTL Software Package, using the space group P 21 21 21, with Z=4 for the formula unit, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile. The final anisotropic full-matrix least-squares refinement on F2 with 403 variables converged at R1=5.73%, for the observed data and wR2=17.09% for all data. The goodness-of-fit was 1.065. The largest peak in the final difference electron density synthesis was 0.344 e-/Å3 and the largest hole was −0.267 e-/Å3 with an RMS deviation of 0.062 e-/Å3. On the basis of the final model, the calculated density was 1.309 g/cm3 and F(000), 1312 e-.

Crystallographic Results of Form B (dehydrated from monohydrate): Bruker D8 QUEST Single-crystal X-ray Diffractometer, equipped with high brightness IμS 3.0 microfocus (50 kV×1 mA) for Cu radiation ($\lambda$=1.54178 Å) and with PHOTON II Charge-Integrating Pixel Array Detector of superior speed, sensitivity, and accuracy, was used for screening/evaluation of crystals and for diffraction data collection. Bruker APEX3 software suite including SHELXTL was used for diffraction experiments including data collection and integration, and for solving, refining, displaying and publishing of structural results. A clear colorless needle-like specimen of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, approximate dimensions 0.060 mm×0.080 mm×0.120 mm, was used for the X-ray crystallographic analysis. The X-ray intensity data were measured ($\lambda$=1.54178 Å) with the crystal kept at 293K using a Cryostream 800 PLUS temperature control device. A total of 360 frames were collected. The total exposure time was 1.00 hours. The frames were integrated with the Bruker SAINT software package using a narrow-frame algorithm. The integration of the data using an orthorhombic unit cell yielded a total of 6472 reflections to a maximum $\theta$ angle of 50.59° (1.00 Å resolution), of which 2627 were independent (average redundancy 2.464, completeness=82.3%, Rint=4.24%, Rsig=6.65%) and 1863 (70.92%) were greater than 2σ(F2). The final cell constants of a=8.1450(6) Å, b=12.4844(9) Å, c=30.446(2) Å, volume=3095.9(4) Å3, are based upon the refinement of the XYZ-centroids of 1720 reflections above 20 σ(I) with 5.805°<2θ<86.51°. Data were corrected for absorption effects using the Multi-Scan method (SADABS). The ratio of minimum to maximum apparent transmission was 0.899. The calculated minimum and maximum transmission coefficients (based on crystal size) are 0.8420 and 0.9160. The structure was solved and refined using the Bruker SHELXTL Software Package, using the space group P 21 21 21, with Z=4 for the formula unit, 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile. The final anisotropic full-matrix least-squares refinement on F2 with 389 variables converged at R1=4.72%, for the observed data and wR2=12.55% for all data. The goodness-of-fit was 1.069. The largest peak in the final difference electron density synthesis was 0.168 e-/Å3 and the largest hole was −0.197 e-/Å3 with an RMS deviation of 0.044 e-/Å3. On the basis of the final model, the calculated density was 1.296 g/cm3 and F(000), 1272 e-.

Comparative Example 5

Stability of Form B Versus Amorphous

Figure 21:
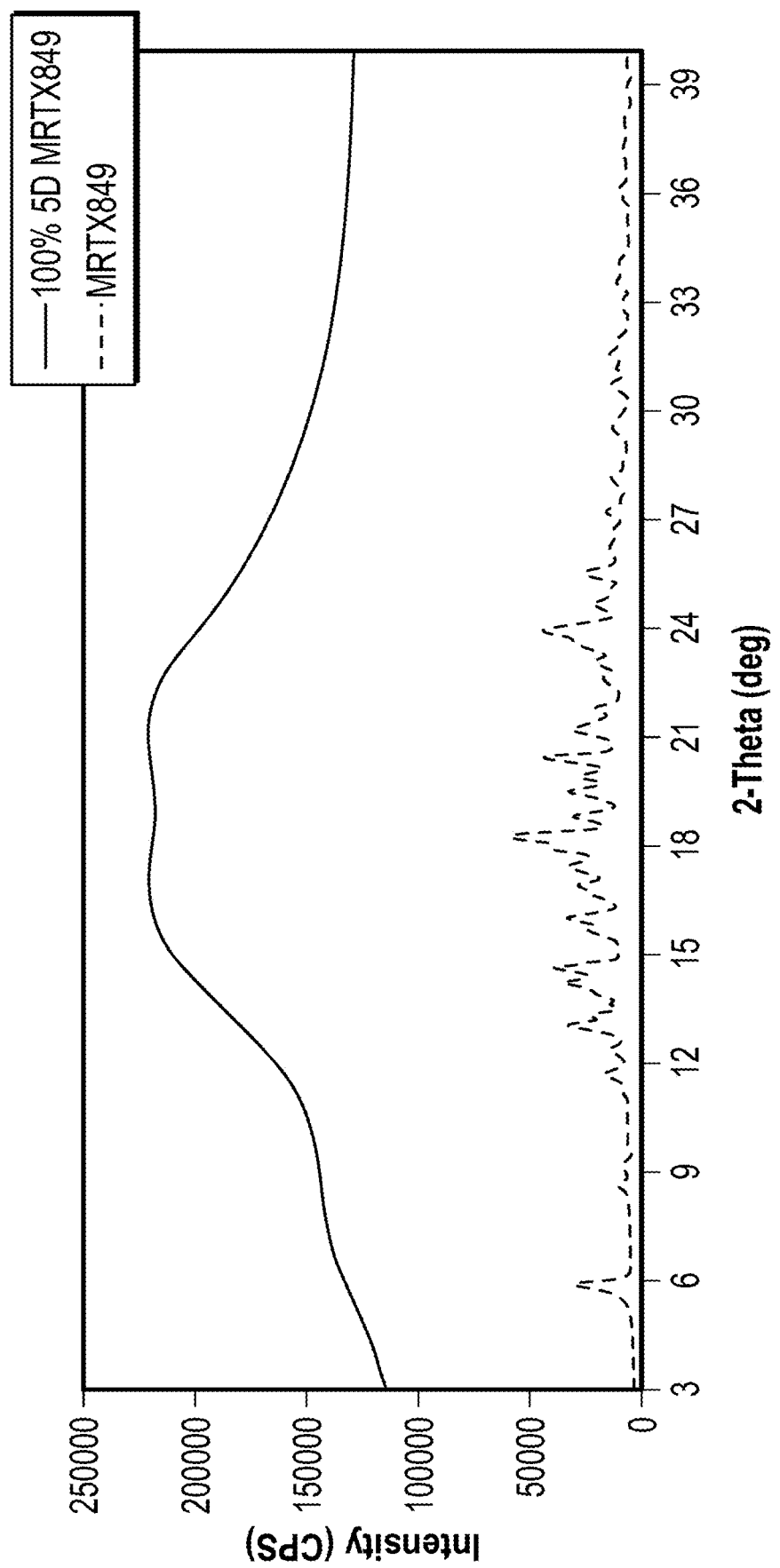
FIG. 21 illustrates a XRPD pattern of a mixture of crystalline Form A and Form B, compared to a XRPD pattern of amorphous free base 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, prepared according to Comparative Example 4.

The Form B polymorph was shown to be chemically and/or physically more stable than amorphous form of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile described in Comparative Example 4. XRPD of the material of Comparative Example 4 was consistent with amorphous material. FIG. 21 shows the XRPD pattern of the spray dried material of Comparative Example 4 compared to the starting material constituted of a mixture of crystalline Forms A and B.

A comparative assessment of the chemical stability of amorphous 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile (MRTX849) with crystalline (mixture of Form A and Form B) was performed HPLC evaluation of material exposed to various accelerated stress conditions. Results are consistent with the amorphous material exhibiting a higher level of degradation compared to crystalline material (Table 7).

TABLE 7

Tabulated for 1 month MRTX-849 Stability Samples of MRTX849 crystalline compared to amorphous material

| API standard | Total impurities (%) 0.71 | |
|---|---|---|
| | MRTX849 crystalline | MRTX849 amorphous |
| 25° C./60% RH, 1 month | — | 2.21 |
| 40° C./75% RH, 1 month | 0.77 | 3.28 |
| 40° C./75% RH, 1 month, open | — | 2.98 | briefly as follows: samples were stored at 25° C./60% RH. 40° C./75% RH and 60° C. in loosely capped, foil-wrapped small glass vials. Data was obtained for up to two weeks for samples stored at 60° C. and up to two months for samples stored at 25° C./60% RH and 40° C./75% RH. In addition, data was generated from photostability study performed on all three lots as a part of the protocol.

For drug substance forms A and B no change in appearance was observed after two weeks of storage at 60° C. and two months of storage at 25° C./60% RH, and 40° C./75% RH. Color for amorphous material lot changed from tan to brown/light brown at 60° C. condition and after two months at 40° C./75% RH.

Changes in impurity profiles were observed after two weeks of storage at 60° C. for all three lots tested. The increase in total impurities from T(0) was marginal for forms A and B: from 1.1% to 1.4% and from 0.3% to 0.4% respectively. In comparison, change in total impurities for amorphous material was more significant, from 1.4% to 9.9%. Similar impurity profile trends were observed after two months storage at 40° C./75% RH. No significant changes from T(0) were observed for Forms A and B, from 1.1% to 1.2% and from 0.3% to 0.4% of total impurities, respectively. The increase for amorphous material was from 1.4% at T(0) to 5.7% after two months at 40° C./75% RH. No significant changes in impurity profiles for all three lots were noted following two months storage at 25° C./60% RH condition.

In conclusion, crystalline forms A and B of MRTX849 Drug Substance appeared to be comparatively more stable than amorphous material for all storage conditions tested including exposure to ½ ICH conditions as a part of photostability study.

Table 8 illustrates appearance, purity and impurities stability results for crystalline forms (Form A and Form B) and amorphous MRTX849 Drug Substance.

TABLE 8

Thermal Stability: Form A, Form B, Amorphous

| Time Point Condition | Test | Initial T(0) | 1 Week 60° C. | 2 Weeks 40° C./ 75% RH | 2 Weeks 60° C. | 1 Month 25° C./ 60% RH | 1 Month 40° C./ 75% RH | 2 Months 25° C./ 60% RH | 2 Months 40° C./ 75% RH |
|---|---|---|---|---|---|---|---|---|---|
| Form A Unmilled | Appearance | Off-white Solid | Off-white Solid | Off-white Solid | Off-white Solid | Off-white Solid | Off-white Solid | Off-white Solid | Off-white Solid |
| | Total impurities | 1.14 | 1.27 | 1.07 | 1.43 | 0.98 | 1.04 | 1.06 | 1.16 |
| Form B Unmilled | Appearance | Creamy White Solid | Creamy White Solid | Creamy White Solid | Creamy White Solid | Creamy White Solid | Creamy White Solid | Creamy White Solid | Creamy White Solid |
| | Total impurities | 0.25 | 0.31 | 0.37 | 0.40 | 0.23 | 0.35 | 0.25 | 0.44 |
| Amorphous | Appearance | Tan Solid | Brown Solid | Tan Solid | Brown Solid | Tan Solid | Tan Solid | Tan Solid | Light Brown Solid |
| | Total impurities | 1.41 | 5.93 | 1.95 | 9.89 | 1.42 | 2.36 | 1.86 | 5.73 |

Comparative Example 6

Stability of Forms A and B Versus Amorphous

A comparative stability study was performed for crystalline forms (Form A and Form B) and amorphous MRTX849 Drug Substance (DS) material. The study of amorphous, Form A (unmilled) and Form B (unmilled) materials was completed in accordance with study protocol which is When compared to controls, changes in impurity profiles were observed in all samples exposed to 2 ICH (International Council for Harmonization of Technical Requirements for Pharmaceuticals for Human Use) conditions as a part of photostability study. As previously observed with stability samples, increase in total impurities for Forms A and B was less significant compared to amorphous material. For forms A and B, total impurities increased from 1.1% to 3.3% and from 0.3% to 1.6% respectively. The increase for amorphous lot was from 1.6 to 8.8%.

Table 9 illustrates photostability (½ ICH conditions): Vis Stress at 600 klux-hrs, UV Stress at 100 W-hr/m².

TABLE 9

Photostability, Form A, Form B Amorphous

|  | Amorphous T(0) | Amorphous Control | Amorphous 0.5 × ICH | Form A T(0) | Form A Control | Form A 0.5 × ICH | Form B T(0) | Form B Control | Form B 0.5 × ICH |
|---|---|---|---|---|---|---|---|---|---|
| Total Impurities (≥0.05%) | 1.41 | 1.58 | 8.75 | 1.14 | 1.09 | 3.26 | 0.25 | 0.26 | 1.59 |
| Purity | 98.59 | 98.42 | 91.25 | 98.86 | 98.91 | 96.74 | 99.75 | 99.74 | 98.41 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. Crystalline Form A of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile, having an X-ray powder diffraction pattern comprising at least one peak at °2θ selected from 8.6±0.2, 14.6±0.2, 16.9±0.2 and 18.3±0.2.

2. The crystalline form according to claim 1, having an X-ray powder diffraction pattern comprising two or more peaks at °2θ selected from 8.6±0.2, 14.6±0.2, 16.9±0.2 and 18.3±0.2.

3. The crystalline form according to claim 1, having an X-ray powder diffraction pattern comprising peaks at °2θ at 8.6±0.2, 14.6±0.2, 16.9±0.2 and 18.3±0.2.

4. The crystalline form according to claim 2, having an X-ray powder diffraction pattern comprising peaks at °2θ at 5.8±0.2, 8.6±0.2, 12.3±0.2, 13.0±0.2, 14.2±0.2, 14.6±0.2, 16.0±0.2, 16.9±0.2, 18.1±0.2, 18.3±0.2, 20.4±0.2, 21.2±0.2, 23.9±0.2 and 25.5±0.2.

5. The crystalline form according to claim 1, having an XRPD pattern as shown in FIG. 1A or FIG. 1B.

6. The crystalline form according to claim 1, having a DSC thermogram as shown in FIG. 2.

7. The crystalline form of claim 1, having a thermogravimetric analysis ("TGA") profile as shown in FIG. 3.

8. The crystalline form of claim 1, having dynamic vapor sorption ("DVS") isotherm as shown in FIG. 4.

9. A pharmaceutical composition comprising the crystalline form of claim 1 and at least one pharmaceutically acceptable excipient and/or diluent.

10. Crystalline Form B of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile having an X-ray powder diffraction pattern comprising at least one peak at °2θ selected from 16.7±0.2, 17.5±0.2 and 18.8±0.2.

11. The crystalline form according to claim 10, having an X-ray powder diffraction pattern comprising peaks at °2θ at 16.7±0.2, 17.5±0.2 and 18.8±0.2.

12. The crystalline form according to claim 10, having an X-ray powder diffraction pattern comprising two or more peaks at °2θ selected from 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

13. The crystalline form according to claim 10, having an X-ray powder diffraction pattern comprising peaks at °2θ at 5.8±0.2, 13.3±0.2, 13.9±0.2, 14.2±0.2, 15.6±0.2, 15.9±0.2, 16.7±0.2, 17.5±0.2, 17.9±0.2, 18.1±0.2, 18.8±0.2, 19.5±0.2, 19.9±0.2, 21.4±0.2, 21.8±0.2, 23.1±0.2, 23.7±0.2 and 24.7±0.2.

14. The crystalline form according to claim 10, having an XRPD pattern as shown in FIG. 5A or FIG. 5B.

15. The crystalline form according to claim 10, having a DSC thermogram as shown in FIG. 6 or FIG. 12.

16. The crystalline form of claim 10, having a TGA profile as shown in FIG. 7.

17. The crystalline form of claim 10, having a DVS isotherm as shown in FIG. 8.

18. A pharmaceutical composition comprising the crystalline form of claim 10 and at least one pharmaceutically acceptable excipient and/or diluent.

19. Crystalline Form C of 2-[(2S)-4-[7-(8-chloro-1-naphthyl)-2-[[(2S)-1-methylpyrrolidin-2-yl]methoxy]-6,8-dihydro-5H-pyrido[3,4-d]pyrimidin-4-yl]-1-(2-fluoroprop-2-enoyl)piperazin-2-yl]acetonitrile having an X-ray powder diffraction pattern comprising at least one peak at °2θ selected from 16.4±0.2 and 19.7±0.2.

20. The crystalline form of claim 19, having an X-ray powder diffraction pattern comprising peaks at °2θ at 16.4±0.2 and 19.7±0.2.

21. The crystalline form according to claim 19, having an X-ray powder diffraction pattern comprising two or more peaks at °2θ selected from 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

22. The crystalline form according to claim 19, having an X-ray powder diffraction pattern comprising peaks at °2θ at 5.7±0.2, 13.3±0.2, 13.9±0.2, 14.2±0.2, 15.5±0.2, 16.4±0.2, 17.8±0.2, 18.0±0.2, 19.7±0.2, 23.2±0.2, 23.7±0.2, 24.4±0.2 and 26.7±0.2.

23. The crystalline form according to claim 19, having an XRPD pattern as shown in FIG. 9.

24. The crystalline form according to claim 19, having a DSC thermogram as shown in FIG. 10.

25. The crystalline form according to claim 19, having a TGA profile as shown in FIG. 10.

26. The crystalline form according to claim 19, wherein the crystalline form is a hydrate.

27. The crystalline form according to claim 1, wherein the crystalline form comprises less than 1.0% by weight of residual organic solvents.

28. The crystalline form according to claim 10, wherein the crystalline form comprises less than 1.0% by weight of residual organic solvents.

29. The crystalline form according to claim 19, wherein the crystalline form comprises less than 1.0% by weight of residual organic solvents.

30. A pharmaceutical composition comprising the crystalline form of claim 19 and at least one pharmaceutically acceptable excipient and/or diluent.

\* \* \* \* \*